(12) United States Patent
Lim

(10) Patent No.: US 9,429,582 B2
(45) Date of Patent: Aug. 30, 2016

(54) TYROSINE-PHOSPHORYLATED WBP2, A NOVEL CANCER TARGET AND BIOMARKER

(75) Inventor: Yoon Pin Lim, Singapore (SG)

(73) Assignee: National University of Singapore, Singapore (SG)

( * ) Notice: Subject to any disclaimer, the term of this patent is extended or adjusted under 35 U.S.C. 154(b) by 20 days.

(21) Appl. No.: 13/819,940

(22) PCT Filed: Aug. 25, 2011

(86) PCT No.: PCT/SG2011/000293
§ 371 (c)(1),
(2), (4) Date: Feb. 28, 2013

(87) PCT Pub. No.: WO2012/030302
PCT Pub. Date: Mar. 8, 2012

(65) Prior Publication Data
US 2013/0273056 A1 Oct. 17, 2013

(30) Foreign Application Priority Data

Aug. 30, 2010 (SG) .............. 201006302-2

(51) Int. Cl.
| | | |
|---|---|---|
| G01N 33/564 | (2006.01) |
| G01N 33/68 | (2006.01) |
| A61K 45/06 | (2006.01) |
| C07K 14/47 | (2006.01) |
| G01N 33/574 | (2006.01) |
| A61K 31/18 | (2006.01) |
| A61K 31/566 | (2006.01) |
| A61K 31/7052 | (2006.01) |
| A61K 39/395 | (2006.01) |
| C07K 16/18 | (2006.01) |

(52) U.S. Cl.
CPC .......... *G01N 33/6893* (2013.01); *A61K 31/18* (2013.01); *A61K 31/566* (2013.01); *A61K 31/7052* (2013.01); *A61K 39/3955* (2013.01); *A61K 45/06* (2013.01); *C07K 14/4702* (2013.01); *C07K 14/4748* (2013.01); *C07K 16/18* (2013.01); *G01N 33/57496* (2013.01); *G01N 2440/14* (2013.01)

(58) Field of Classification Search
None
See application file for complete search history.

(56) References Cited

U.S. PATENT DOCUMENTS

| 2003/0077577 A1 | 4/2003 | Pirozzi et al. |
| 2010/0003255 A1 | 1/2010 | Croner et al. |
| 2010/0159477 A1* | 6/2010 | Hornbeck et al. ............. 435/7.4 |

FOREIGN PATENT DOCUMENTS

WO   WO2008009000   *   1/2008

OTHER PUBLICATIONS

Dhananjayan et al (Mole Endo 20:2343-54, 2006).*
CN2011180051871.0, Mar. 20, 2015, Chinese Office Action.
Ren et al., Preparation and application of phosphorylated LKB1 (THr336) Polyclonal Antibody. Chin J Biologicals. Nov. 2008;21(11):995-1005.
Zhang et al., Selection of oligonucleotide aptamers and applications in biological analytical chemistry. Biotechnology. 2009;19(5):90-4.
Lara et al., A phase II trial of the Src-kinase inhibitor AZD0530 in patients with advanced castration-resistant prostate cancer: a California Cancer Consortium study. Anticancer Drugs. Mar. 2009;20(3):179-84. doi: 10.1097/CAD.0b013e328325a867.
Chen et al., Differential expression of novel tyrosine kinase substrates during breast cancer development. Mol Cell Proteomics. Dec. 2007;6(12):2072-87. Epub Sep. 12, 2007.
Dhananjayan et al., WW domain binding protein-2, an E6-associated protein interacting protein, acts as a coactivator of estrogen and progesterone receptors. Mol Endocrinol. Oct. 2006;20(10):2343-54. Epub Jun. 13, 2006.
Howell et al., Fulvestrant, formerly ICI 182,780, is as effective as anastrozole in postmenopausal women with advanced breast cancer progressing after prior endocrine treatment. J Clin Oncol. Aug. 15, 2002;20(16):3396-403.
Lim et al., Tyrosine phosphorylation of transcriptional coactivator WW-domain binding protein 2 regulates estrogen receptor α function in breast cancer via the Wnt pathway. FASEB J. Sep. 2011;25(9):3004-18. Epub Jun. 3, 2011.
Lim et al., WBP2: A novel phosph-oncoprotein in estrogen receptor-positive breast cancer. Proceedings of the American Association for Cancer Research Annual Meeting. Apr. 2010;51:1208.

(Continued)

*Primary Examiner* — Lei Yao
(74) *Attorney, Agent, or Firm* — Wolf, Greenfield & Sacks, P.C.

(57) ABSTRACT

WW-binding protein 2 (WBP2) has been demonstrated in different studies to be a tyrosine kinase substrate, to activate ERα/PR transcription and to play a role in breast cancer. However, the role of WBP2 tyrosine phosphorylation in regulating ER function and breast cancer biology is unknown. Here, we established WBP2 as a tyrosine phosphorylation target of estrogen signaling via EGFR crosstalk. Using dominant negative, constitutively active mutants, RNAi and pharmacological studies, we demonstrated that phosphorylation of WBP2 at Tyr192 and Tyr231 could be regulated by c-Src and c-Yes kinases. We further showed that abrogating WBP2 phosphorylation impaired >60% of ERα reporter activity putatively by blocking nuclear entry of WBP2 and its interaction with ERα. Compared to vector control, overexpression of WBP2 and its phospho-mimic mutant in MCF7 resulted in larger tumors in mice, induced loss of cell-cell adhesion, enhanced cell proliferation, anchorage-independent growth, migration and invasion in both estrogen-dependent and-independent manner, events of which could be substantially abolished by overexpression of phosphorylation-defective mutant. Wnt/β-catenin inhibitor FH535 blocked phospho-WBP2-mediated cancer cell growth more pronouncedly than tamoxifen and fulvestrant, in part by reducing the expression of ERα.

5 Claims, 39 Drawing Sheets

(56) References Cited

OTHER PUBLICATIONS

Zaveri et al., A novel peroxisome proliferator-activated receptor delta antagonist, SR13904, has anti-proliferative activity in human cancer cells. Cancer Biol Ther. Jul. 2009;8(13):1252-61. Epub Jul. 7, 2009.
Chinese Office Action for Application No. 201180051871.0 mailed Nov. 12, 2015.
Vogelmann et al., TGFbeta-induced downregulation of E-cadherin-based cell-cell adhesion depends on PI3-kinase and PTEN. J Cell Sci. Oct. 15, 2005;118(Pt 20):4901-12.
SG 102015083075, Jan. 25, 2016, Search Report and Written Opinion.
SG 10201508307S, Jun. 16, 2016, Written Opinion.
Kawakatsu et al., A new monoclonal antibody which selectively recognizes the active form of Src tyrosine kinase. J Biol Chem. Mar. 8, 1996;271(10):5680-5.

\* cited by examiner

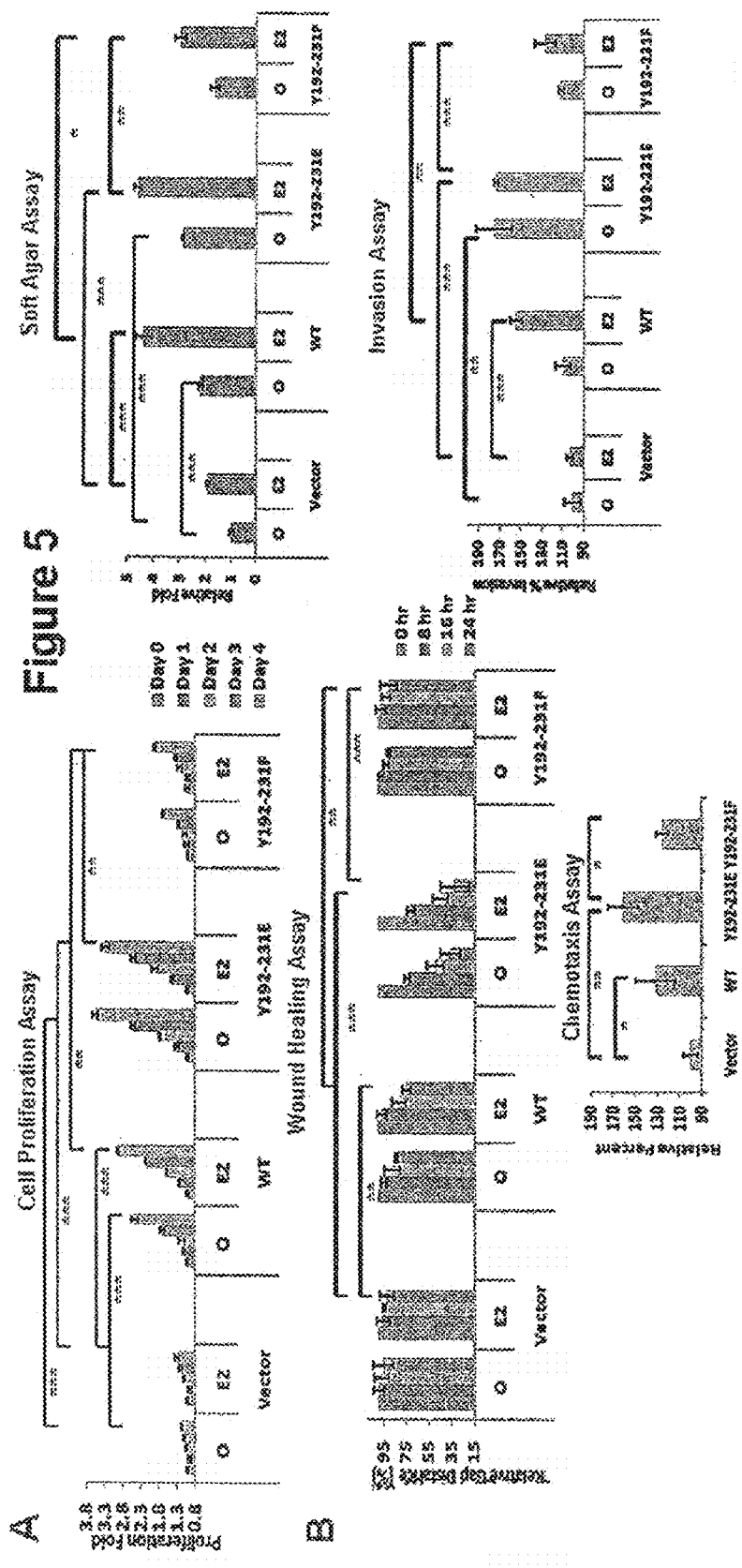

```
          10         20         30         40         50         60
MALNKNHSEG GGVIVNNTES ILMSYDHVEL TENDMKNVPE AFKGTKKGTV YLTPYRVIFL 70         80         90        100        110        120
SKGKDAMQSF MMPFYLMKDC EIKQPVFGAN YIKGTVKAEA GGGWEGSASY KLTFTAGGAI 130        140        150        160        170        180
EFGQRMLQVA SQASRGEVPS GAYGYSYMPS GAYVYPPPVA NGMYPC PPGY  PYPPPPPEFY 190        200        210        220        230        240
PGPPMMDGAM GY VQPE PPPY  PGPMEPPVSG PDVPSTPAAE AKAAEAAASA  YY NPGNPHNV 250        260
YMPTSQPPPP  PYY PPEDKKT Q
```

Figure 7

Lane 1: undifferentiated HM-1 (overconfluent)
Lane 2: undifferentiated HM-1 (80-90% confluent)
Lane 2: Differentiated HM-1 (following LIF withdrawal and Retinoic acid

WBP2-Y192-231E

WT

WBP2-Y192-231F

Figure 16
Figure 17
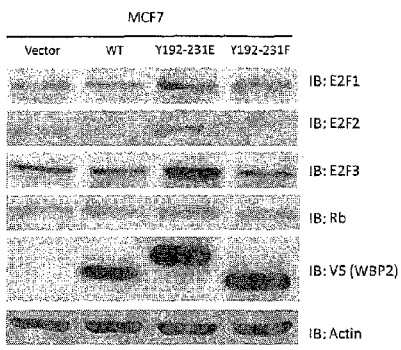
A  siRNAs against WBP2 and E2F1/3
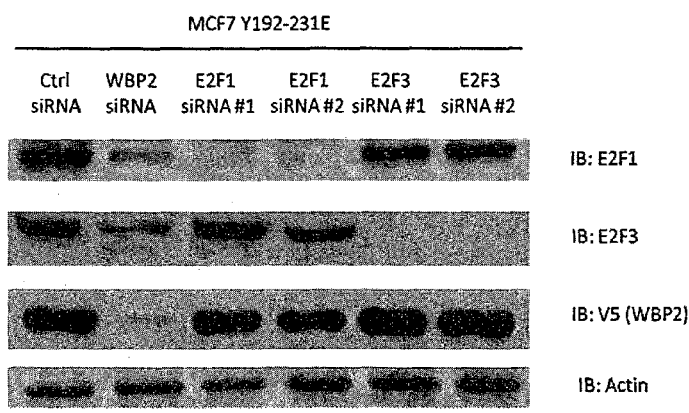
B
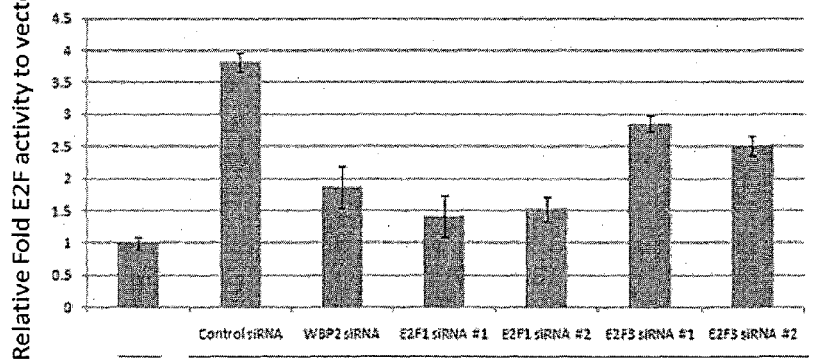

TYROSINE-PHOSPHORYLATED WBP2, A NOVEL CANCER TARGET AND BIOMARKER

CROSS-REFERENCE TO RELATED APPLICATION

This application is a national stage filing under 35 U.S.C. §371 of international application PCT/SG2011/000293, filed Aug. 25, 2011, which was published under PCT Article 21(2) in English, and claims the benefit of Singapore Patent Application No. 201006302-2filed on 30 Aug. 2010, the entire contents of which are incorporated by reference.

FIELD OF INVENTION

The invention relates generally to methods and kits for determining predisposition, or diagnosis and/or treatment of cancer.

BACKGROUND

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Potentiation of gene transcription by nuclear hormone receptors involves its interplay with co-activators and the basal transcriptional machinery through protein-protein interactions (1, 2). Co-activator can act as transcriptional adaptor or modify chromatin through histone acetyl transferases (HAT) or nucleosome remodeling complexes. Furthermore, coactivators regulate mRNA transport, translation and posttranslational modification of the synthesized proteins. Some of the known nuclear hormone receptor coactivators include p160 family members of co-activators, SRC-1, SRC-2[TIF-2/GRIP-1/NCoA-2], SRC-3 [pCIP/ACTR/AIB-1/RAC-3/TRAM-1], NRIF-3, E6-AP and WBP2. Due to their pleiotropic roles, it is not surprising that transcription co-activators are emerging as a group of proteins increasingly implicated in cancer development (3-5).

Transcription co-activators are often subject to posttranslational modification, e.g. phosphorylation. Phosphorylation of specific members of SRC/p160 family of proteins enhanced their nuclear localization (6), inhibited their interactions with non-nuclear receptor activators (7) or stimulated their intrinsic coactivator activity (8). Phosphorylation of AIB1 and PGC-1 regulated both their half-life and activity (9, 10). Furthermore, phosphorylation of NRIF3 via Pak1 promoted ERα transactivation through increased ERα-NRIF3 interaction (5).

WW-domain binding protein (WBP2) is a transcription coactivator demonstrated to selectively and specifically enhance ERα and PR transactivation via hormone-dependent ERα/PR-WBP2 interaction and recruitment of WBP2 to hormone-responsive elements (11). WBP2 contains an intrinsic activation domain. One of its three polyproline (PPXY) motifs-PY3 is essential for its coactivating function in ERα/PR transactivation. Its coactivator activity could be further enhanced by YAP (Yes kinase-associated protein), which also regulated several transcription factors, e.g. p73 (12), Runx2 (13), TEAD/TEF (14) and ErbB4 (15).

Our previous study has identified WBP2 as a novel tyrosine kinase substrate that displayed differential phosphorylation across the MCF10AT model of breast cancer progression (16). Exogenously expressed WBP2 was subsequently validated to be an authentic target of EGFR. We hypothesized that EGFRmediated tyrosine phosphorylation of WBP2 plays a role in regulating ERα function and breast cancer biology. We therefore attempted to delineate the signaling pathways for the EGFR-mediated tyrosine phosphorylation of WBP2 and to study the impact of WBP2 phosphorylation on its coactivator activity. The role of WBP2 and its tyrosine phosphorylation on the ER-positive breast cancer biology and the underlying mechanisms were also investigated.

SUMMARY

Accordingly one aspect of the invention includes a method of detecting cancer in a patient comprising the steps of:
a) Measuring an amount of a polypeptide of SEQ ID No. 1 with a phosphorylated tyrosine at Y192 in a first sample isolated from the patient; and
b) Comparing the amount of polypeptide of SEQ ID No. 1 with a phosphorylated tyrosine at Y192 in the sample to an amount of polypeptide of SEQ ID No. 1 with a phosphorylated tyrosine at Y192 in a second sample isolated from normal, non-cancerous cells,
wherein an amplified amount of polypeptide of SEQ ID No. 1 with a phosphorylated tyrosine at Y192 in the first sample relative to the amount of polypeptide of SEQ ID No. 1 with a phosphorylated tyrosine at Y192 in the second sample indicates cancer is present in the first sample.

Preferably the amount of the polypeptide of SEQ ID No. 1 with a phosphorylated tyrosine at Y192 in the first and second sample also detects phosphorylation of tyrosine at Y231 of the polypeptide of SEQ ID No. 1 wherein an amplified amount of polypeptide of SEQ ID No. 1 with a phosphorylated tyrosine at Y192 and Y231 in the first sample relative to the amount of polypeptide of SEQ ID No. 1 with a phosphorylated tyrosine at Y192 and Y231 in the second sample indicates cancer is present in the first sample.

Preferably the cancer is caused by, initiated or dependent on EGFR, c-Src, c-Yes, ER, Wnt, WBP2 or E2F expression or activity.

Preferably the amount of the polypeptide of SEQ ID No. 1 with a phosphorylated tyrosine is measured with an isolated phosphorylation site-specific antibody that specifically binds to a WW-domain binding protein of SEQ ID. NO. 1 only when the polypeptide is phosphorylated at the tyrosine Y192, or tyrosine Y231, or the tyrosine Y192 and the tyrosine Y231 wherein the antibody does not bind the polypeptide of SEQ ID No. 1 when it is not phosphorylated at said tyrosine.

Preferably the method further comprising the steps of:
a) bringing the polypeptide of SEQ ID No. 1 into contact with a polynucleotide probe or primer comprising a polynucleotide sequence capable of hybridising selectively to the polypeptide of SEQ ID No. 1 only when the polypeptide is phosphorylated at the tyrosine Y192, or tyrosine Y231, or the tyrosine Y192 under suitable hybridising conditions; and
b) detecting any duplex formed between the probe or primer and the polypeptide of SEQ ID No. 1 phosphorylated at said tyrosine.

6. The method of any one of claims 1 to 3 whereby the amount of the polypeptide of SEQ ID No. 1 with a phosphorylated tyrosine is measured with an isolated phosphorylation site-specific aptamers that specifically binds to a WW-domain binding protein of SEQ ID. NO. 1 only when the polypeptide is phosphorylated at the tyrosine Y192 or Y231 or the tyrosine Y192 and the tyrosine Y231 wherein the aptamers does not bind the polypeptide of SEQ ID No. 1 when it is not phosphorylated at said tyrosine.

Another aspect of the invention includes an agent to interfere with phosphorylation of tyrosine Y192 and/or Y231 in the polypeptide of SEQ ID NO. 1.

Preferably the agent comprises an isolated phosphorylation site-specific antibody that specifically binds to a WW-domain binding protein of SEQ ID. NO. 1 only when the polypeptide is phosphorylated at the tyrosine Y192, Y231 or the tyrosine Y192 and the tyrosine Y231 wherein the antibody does not bind the polypeptide of SEQ ID No. 1 when it is not phosphorylated at said tyrosine.

Preferably said antibody is an immunoglobulin comprising an immunoglobulin heavy chain.

Preferably said antibody is an immunoglobulin comprising an immunoglobulin light chain.

Preferably the immunoglobulin is an IgG1 kappa immunoglobulin.

Preferably the immunoglobulin comprises a human IgG1 constant region within a heavy chain of the immunoglobulin and a human constant region within a light chain of the immunoglobulin.

In one embodiment the immunoglobulin comprises fully or partially human framework regions within the heavy chain and within the light chain.

In one embodiment the immunoglobulin comprises murine framework regions within the heavy chain and within the light chain.

Preferably the antibody is able to be produced in a cell line.

Preferably the agent comprises an isolated phosphorylation site-specific aptamers that specifically binds to a WW-domain binding protein of SEQ ID. NO. 1 only when the polypeptide is phosphorylated at the tyrosine Y192 or the tyrosine Y192 and the tyrosine Y231 wherein the aptamers does not bind the polypeptide of SEQ ID No. 1 when it is not phosphorylated at said tyrosine.

In one embodiment the agent comprises a small interfering RNA such as SEQ ID NO. 2.

Another aspect of the invention includes an agent of the invention for use in the treatment of cancer.

Preferably the agent of the invention is for use in the treatment of breast cancer and lung cancer.

Preferably the agent of the invention further comprising the compound of FH535 of formula 1.

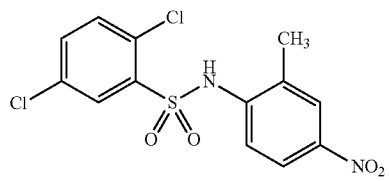 [SMILES: Cc1cc([N+](=O)[O-])ccc1NS(=O)(=O)c1cc(Cl)ccc1Cl]

Another aspect of the invention includes a composition comprising the agent of the invention and the compound of FH535 of formula 1.

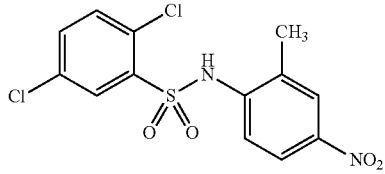 [SMILES: Cc1cc([N+](=O)[O-])ccc1NS(=O)(=O)c1cc(Cl)ccc1Cl]

Another aspect of the invention includes a method of treating a patient afflicted with cancer, comprising the steps of:
(a) administering to the patient an agent to interfere with phosphorylation of tyrosine Y192 and/or Y231 in the polypeptide of SEQ ID NO. 1,

BRIEF DESCRIPTION OF THE DRAWINGS

Preferred embodiments of the invention will be described with reference to the following drawings of which.

A: HeLa were co-transfected with EGFR and V5-tagged WT or individual Y→F mutant of WBP2. 24 hr post-transfection, cells were serum-starved and stimulated with 50 ng/ml EGF for 5 min with/without 1 hr pre-treatment with 10 µM Iressa or 1 µM AZD0530. Whole cell lysates were used for IP/IB analysis with antibodies indicated. B: HeLa were co-transfected with EGFR and V5-tagged WT or individual Y→F mutant of WBP2 in the absence or presence of Src-DN overexpression. C: HeLa were co-transfected with (a) WBP2; (b) WBP2 and EGFR; (c) WBP2 and wild-type (WT) Src; (d) WBP2 and constitutively active (CA) Src; (e) WBP2, EGFR and WT-Src; (f) WBP2, EGFR ad CA-Src; (g) Y192-231F, EGFR and WT-Src. For experiments B and C, 24 hr post-transfection, cells were serum-starved overnight and stimulated with 50 ng/ml EGF for 5 min. Whole cell lysates were used for IP/IB analysis with antibodies indicated. D: HeLa were co-transfected with EGFR and V5-tagged WT or individual Y→F mutant of WBP2. 24 hrpost-transfection, cells were serum-starved and stimulated with 50 ng/ml EGF for 5 min with/without 1 hr pre-treatment with 10 μM Iressa or 1 μM AZD0530. Whole cell lysates were used for IP/IB analysis with antibodies indicated. E: HeLa were co-transfected with EGFR and V5-tagged WT or individual Y→F mutant of WBP2 in the absence or presence of Src-DN-K295M overexpression. F: HeLa were cotransfected with (a) WBP2; (b) WBP2 and EGFR; (c) WBP2 and wild-type (WT) Src; (d) WBP2 and constitutively-active (CA) Src-Y529F; (e) WBP2, EGFR and WT-Src; (f) WBP2, EGFR ad CA-Src; (g) Y192-231F, EGFR and WT-Src. For experiments B and C, 24 hr post-transfection, cells were serum-starved overnight and stimulated with 50 ng/ml EGF for 5 min. Whole cell lysates were used for IP/IB analysis with antibodies indicated. G: MCF7 were co-transfected with V5-tagged WBP2 and either negative control siRNA, c-Yes siRNA or c-Src siRNA. For both experiments, 24 hr post-transfection, cells were serum-starved overnight and stimulated with 50 ng/ml EGF for 5 min. Whole cell lysates were used for IP/IB analysis with antibodies indicated.

Figure 3:
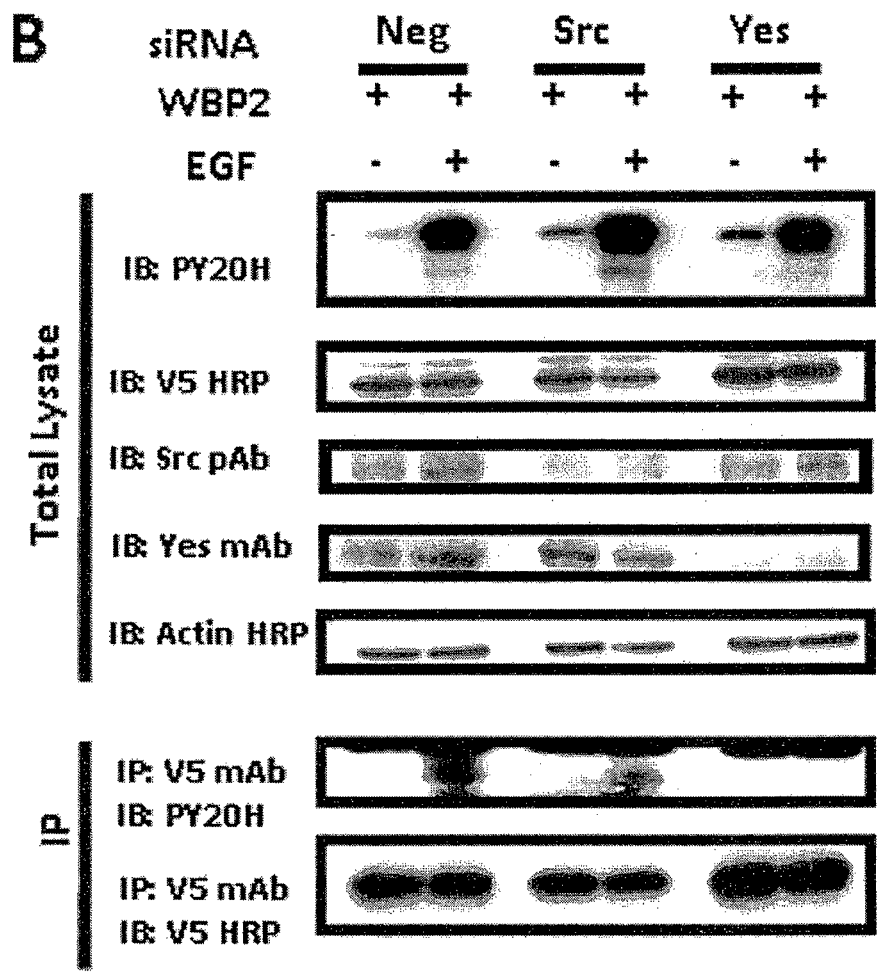

FIG. 3: Regulation of WBP2 Tyrosine Phosphorylation by c-Yes

A: HeLa were co-transfected with (a) WBP2; (b) WBP2/Y192-231F and EGFR; (c) WBP2/Y192-231F and wild-type (WT) Yes; (d) WBP2/Y192-231F, EGFR and WT-Yes; (e) WBP2/Y192-231F and constitutively active (CA) Yes-Y357F; (f) WBP2/Y192-231F, EGFR ad CA-Yes. B: HeLa were co-transfected with V5-tagged WBP2 and either negative control siRNA, c-Src siRNA or c-Yes siRNA. For both experiments, 24 hr posttransfection, cells were serum-starved overnight and stimulated with 50 ng/ml EGF for 5 min. Whole cell lysates were used for IP/IB analysis with antibodies indicated. A: HeLa were co-transfected with (a) WBP2; (b) WBP2/Y192-231F and EGFR; (c) WBP2/Y192-231F and wild-type (WT) Yes; (d) WBP2/Y192-231F, EGFR and WT-Yes; (e) WBP2/Y192-231F and constitutively active (CA) Yes-Y537F; (f) WBP2/Y192-231F, EGFR ad CA-Yes. B: HeLa were co-transfected with V5-tagged WBP2 and either negative control siRNA, c-Yes siRNA or c-Src siRNA. For both experiments, 24 hr posttransfection, cells were serum-starved overnight and stimulated with 50 ng/ml EGF for 5 min. Whole cell lysates were used for IP/IB analysis with antibodies indicated.

Figure 4:
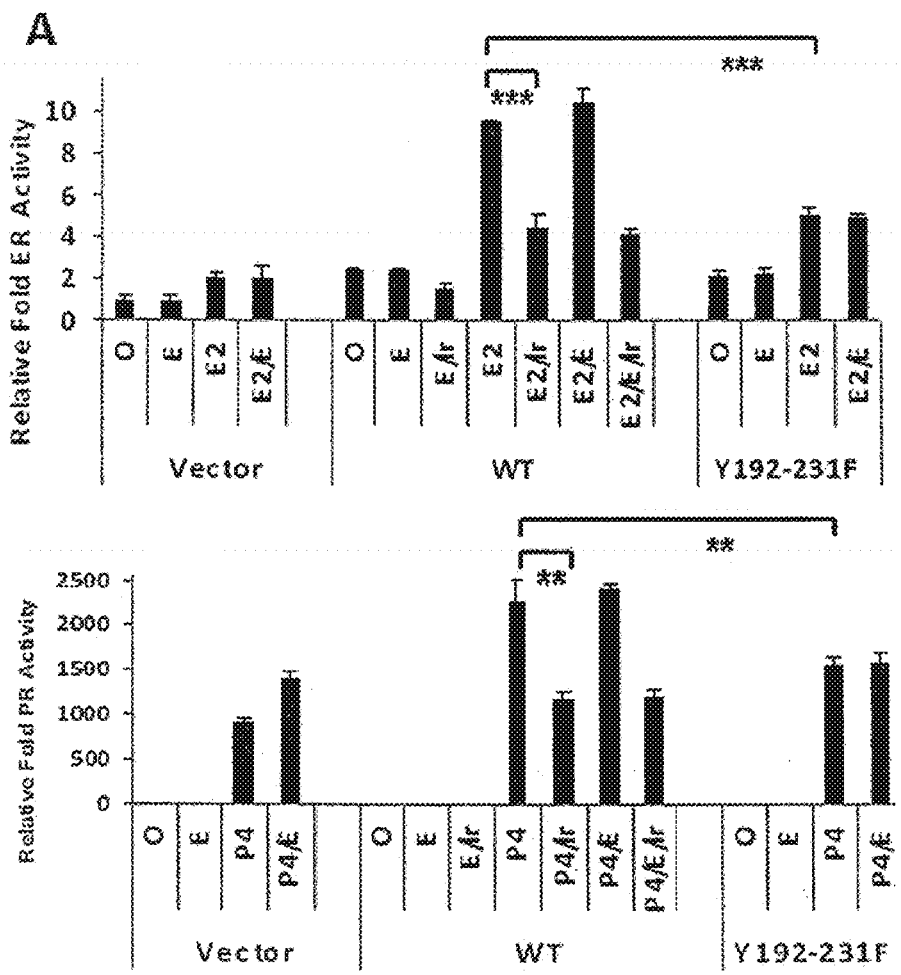
Figure 4:
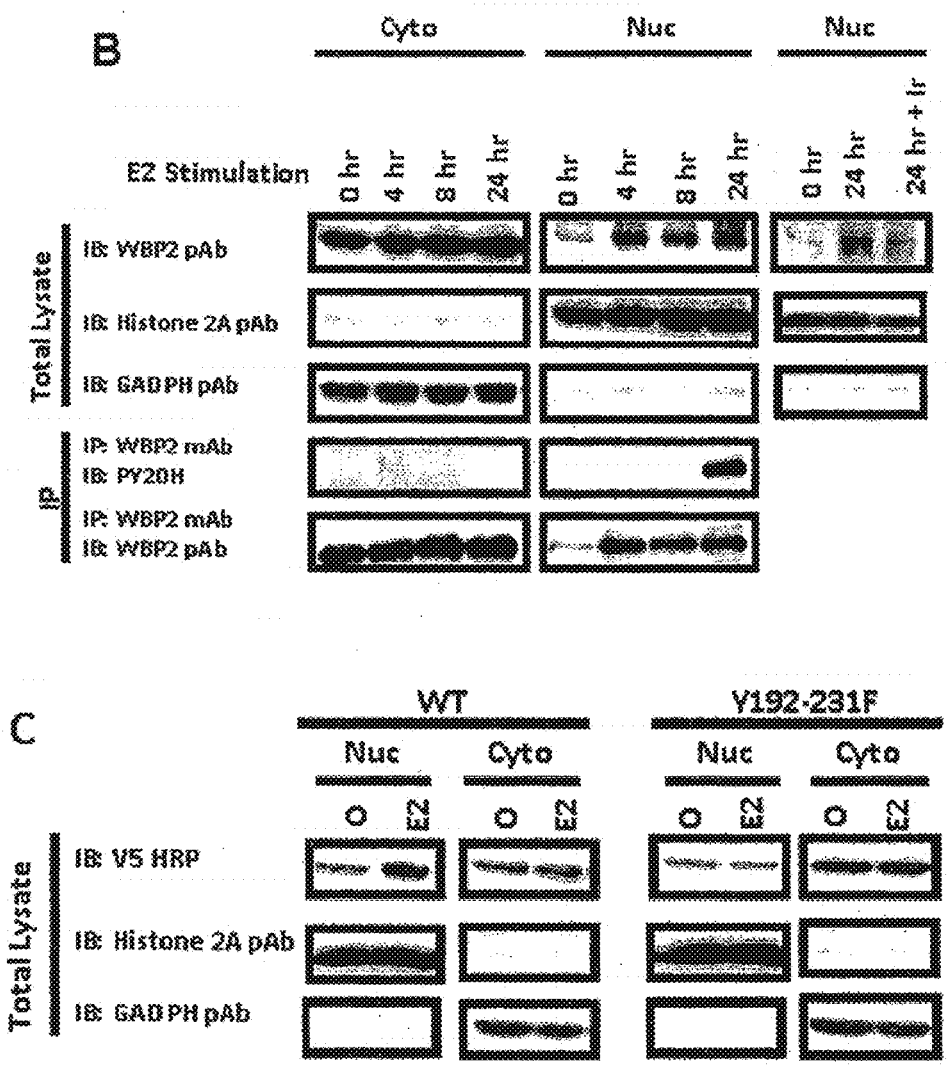
Figure 4:
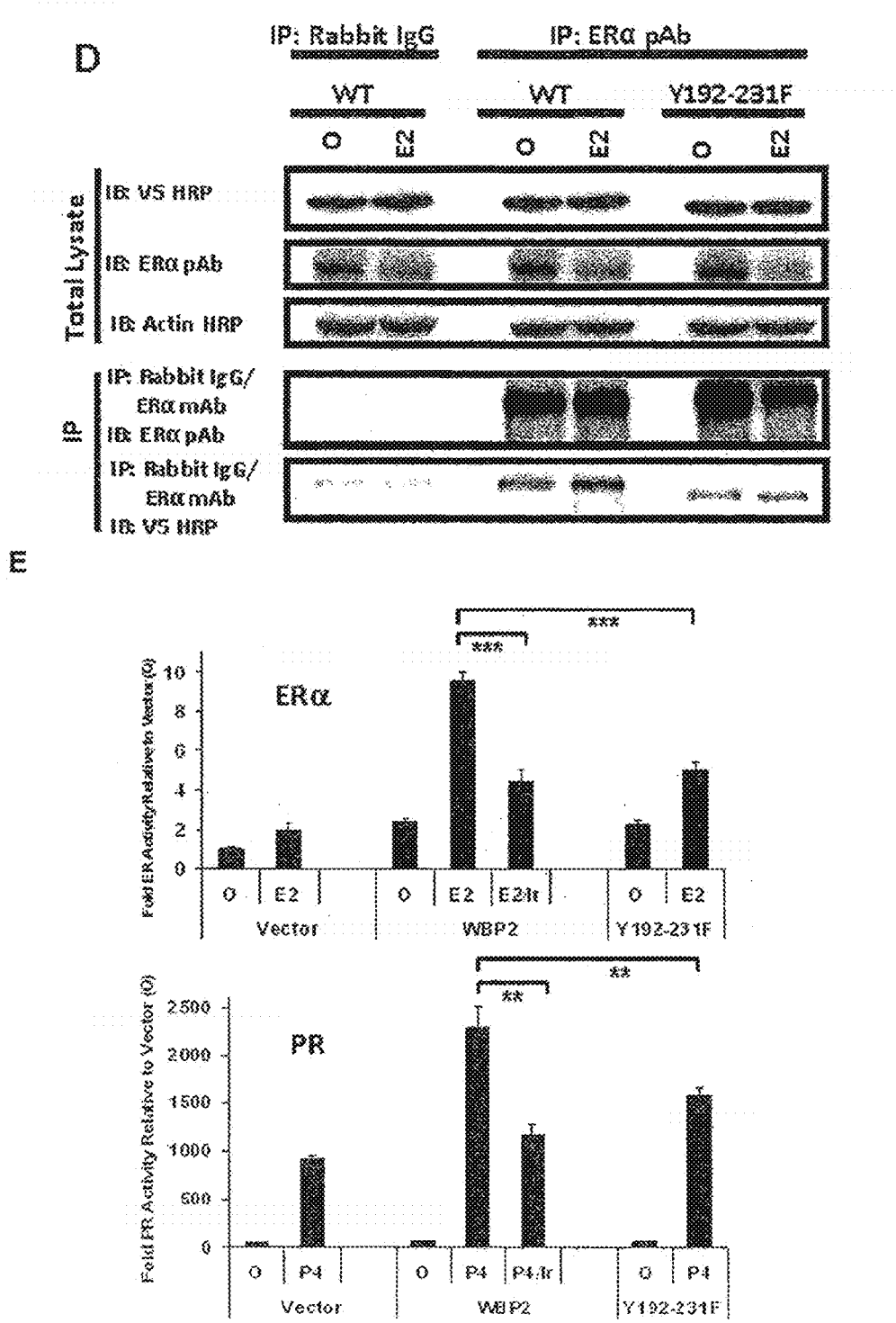
Figure 4:
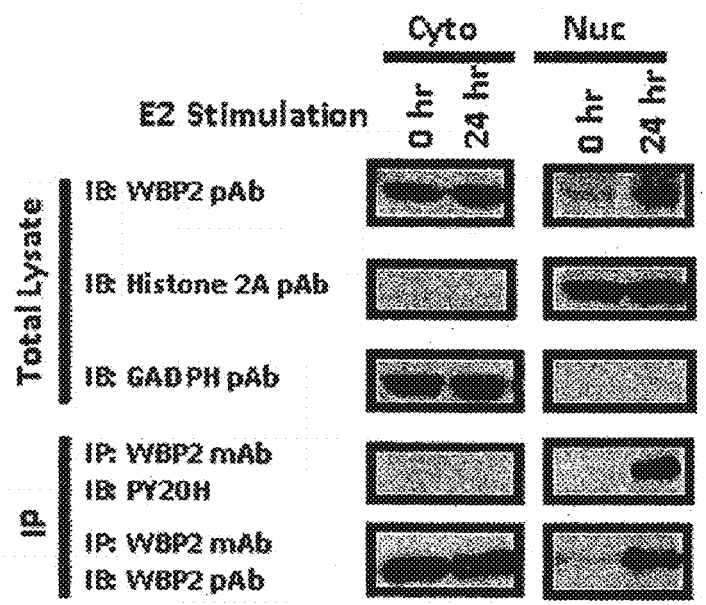
Figure 4:
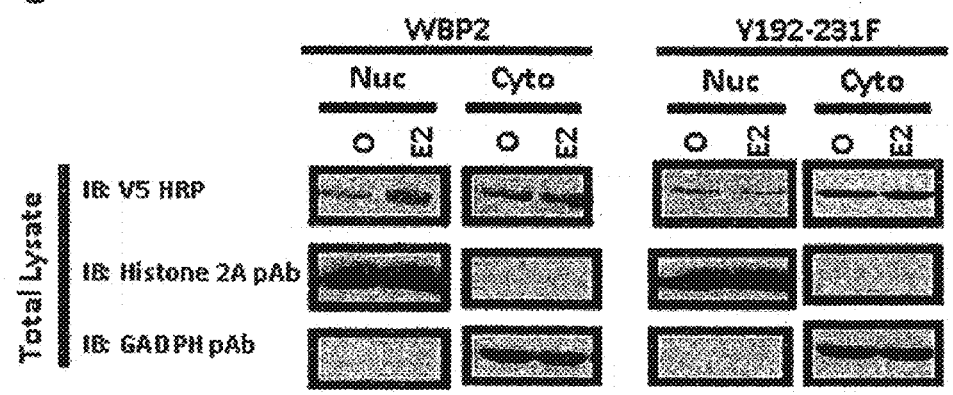
Figure 4:
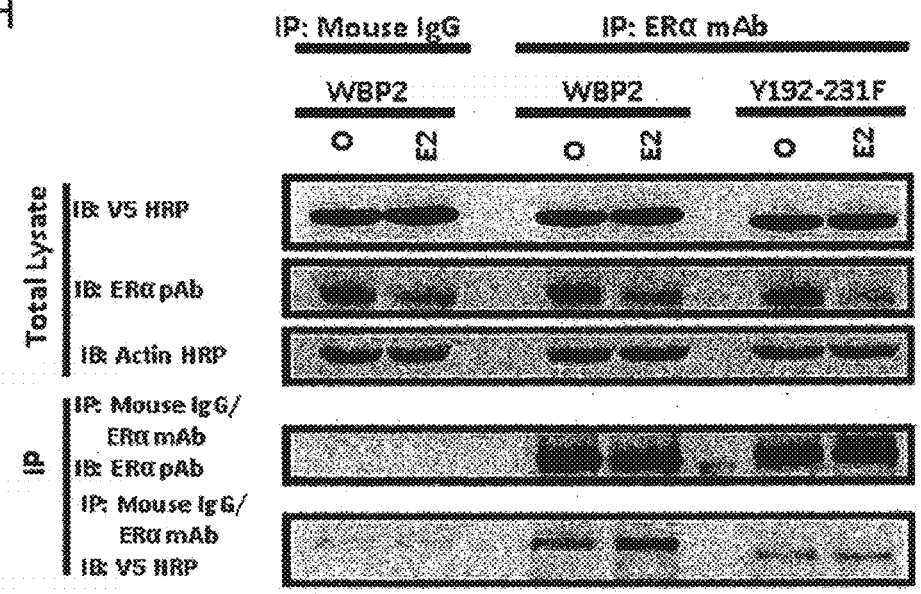
Figure 4:
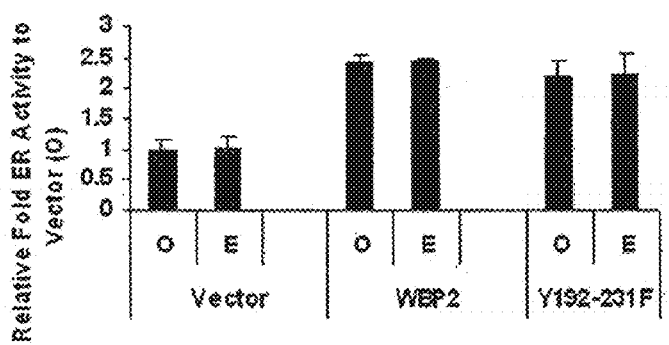
Figure 4:
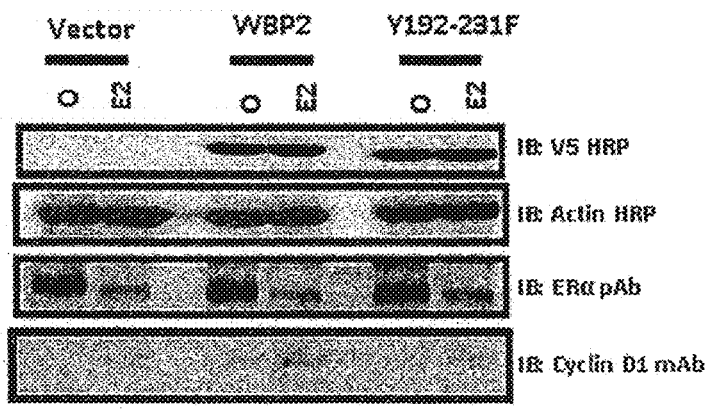
Figure 4:
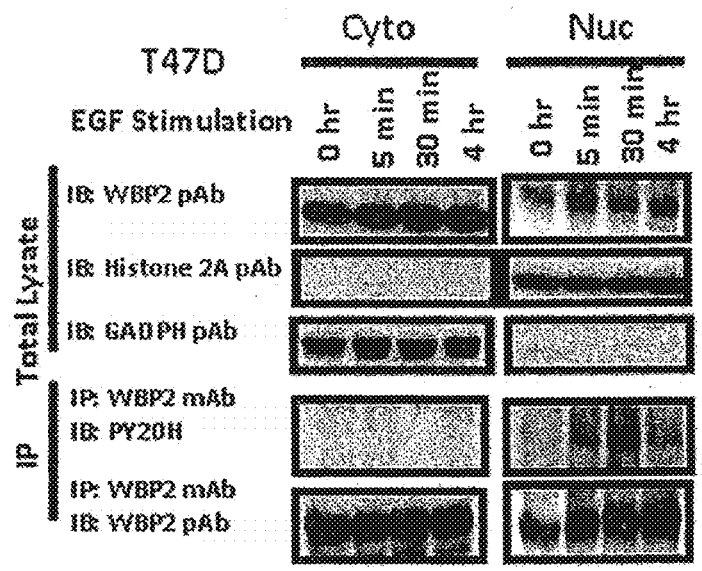
Figure 4:
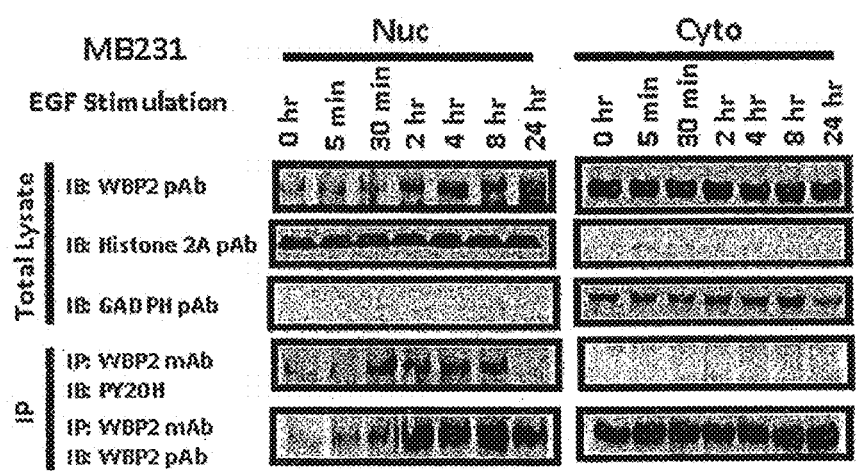
Figure 4:
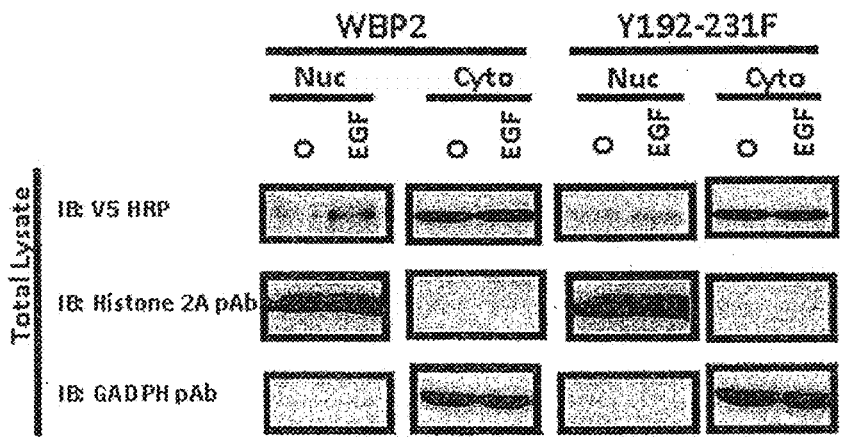

FIG. 4: Tyrosine Phosphorylation of WBP2 Potentiates its Coactivation Function in ERα Activity Via Regulation of its Nuclear Entry and Interaction with ERα

A: Hormone-stripped MCF7 or T47D were co-transfected with vector, WBP2-WT or WBP2-Y192-231F mutant and ERE/PRE-Luciferase reporter constructs. Cells were either left alone or stimulated with (a) 50 ng/ml EGF for 5 min, (b) 10 nM E2/100 nM P4 for 24 hr, (c) E2/P4 and EGF in the absence or presence of 1 hr pretreatment with 100 μM Iressa(Ir). ERα/PR-transactivated luciferase activities in various conditions were then assayed. $P<0.01$, *$P<0.001$, Student's t-test (2-tailed). B: T47D were hormone-stripped and stimulated with 10 nM E2 for the indicated time (0-24 hr) in the absence and presence of 1 hr pretreatment with 10 μM Iressa(k). C: WT-WBP2 or Y192-231F mutant-transfected T47D were hormone stripped followed by 24 hr stimulation with 10 nM E2. For both experiments B and C, cells were then harvested for subcellular fractionation into nuclear and cytoplasmic fractions, which were used for IB/IP analysis with antibodies indicated. Histone 2A and GADPH were used as nuclear and cytoplasmic marker respectively. D: Hormone-stripped MCF7 were transfected with WT-WBP2 or Y192-231F mutant. Twenty four-hour post-transfection, cells were stimulated with 10 nM E2 for 24 hr. Whole cell lysates were used for IB/IP (control IgG or WBP2 antibody) analysis with antibodies indicated. E: Hormone-stripped MCF7 or T47D were co-transfected with vector, WBP2-WT or WBP2-Y192-231F mutant and ERE/PRE-Luciferase reporter constructs. Cells were either left alone or stimulated with 10 nM E2/100 nM P4 for 24 hr in the absence or presence of 1 hr pretreatment with 10 μM Iressa(Ir). ERE (Top panel)/PR (Bottom panel)-transactivated luciferase activities in various conditions were then assayed analyzed in relative to vehicle-treated vector control. $P<0.01$, *$P<0.001$, Student's t-test (2-tailed). F: T47D were hormone-stripped and stimulated with 10 nM E2 for the indicated time (0-24 hr). G: WT-WBP2 or Y192-231F mutant-transfected T47D was hormone-stripped followed by 24 hr stimulation with 10 nM E2. For both experiments B and C, cells were then harvested for subcellular fractionation into nuclear and cytoplasmic fractions, which were used for IB/IP analysis with antibodies indicated. Histone 2A and GADPH were used as nuclear and cytoplasmic marker respectively. H: Hormone-stripped MCF7 were transfected with WT-WBP2 or Y192-231F mutant. Twenty four-hour post-transfection, cells were stimulated with 10 nM E2 for 24 hr. Whole cell lysates were used for IB/IP (control IgG or WBP2 antibody) analysis with antibodies indicated. I: Hormone-stripped MCF7 were co-transfected with vector, WBP2-WT or WBP2-Y192-231F mutant and ERE-Luciferase reporter constructs. Cells were either left alone or stimulated with 50 ng/ml EGF for 5 min. ERα-transactivated luciferase activities in various conditions were then assayed analyzed in relative to vehicle-treated vector control. J: E2-responsive target gene-cyclin D1 protein expression was regulated by tyrosine phosphorylation of WBP2. Hormone stripped vector, WBP2-WT or WBP2-Y192-231F mutant-expressing MCF7 were stimulated with 10 nM of E2. Whole cell lysates were used for IB analysis with antibodies indicated. K: Tyrosine-phosphorylated WBP2 in the nucleus upon EGF stimulation in T47D. T47D were serum starved overnight and stimulated with 50 ng/ml of EGF for 0-4 hr. Cells were then harvested for subcellular fractionation into nuclear and cytoplasmic fractions, which were used for IB/IP analysis with antibodies indicated. Histone 2A and GADPH were used as the nuclear and cytoplasmic marker respectively. L: Tyrosine-phosphorylated WBP2 in the nucleus upon EGF stimulation in MDA-MB231. MDA-MB231 was serum starved overnight and stimulated with 50 ng/ml of EGF for the indicated time (0-24 hr). Cells were then harvested for subcellular fractionation into nuclear and cytoplasmic fractions, which were used for IB/IP analysis with antibodies indicated. Histone 2A and GADPH were used as the nuclear and cytoplasmic marker respectively. M: EGF-stimulated nuclear entry of WBP2 was affected by its defective tyrosine phosphorylation. WT-WBP2 or Y192-231F mutant transfected T47D were (a) serum starved followed by 5 min stimulation with 50 ng/ml of EGF. Cells were then subject to subcellular fractionation into nuclear and cytoplasmic fractions, which were then used for IB/IP analysis with indicated antibodies. Histone 2A and GADPH were used as the nuclear and cytoplasmic marker respectively.

Figure 5:
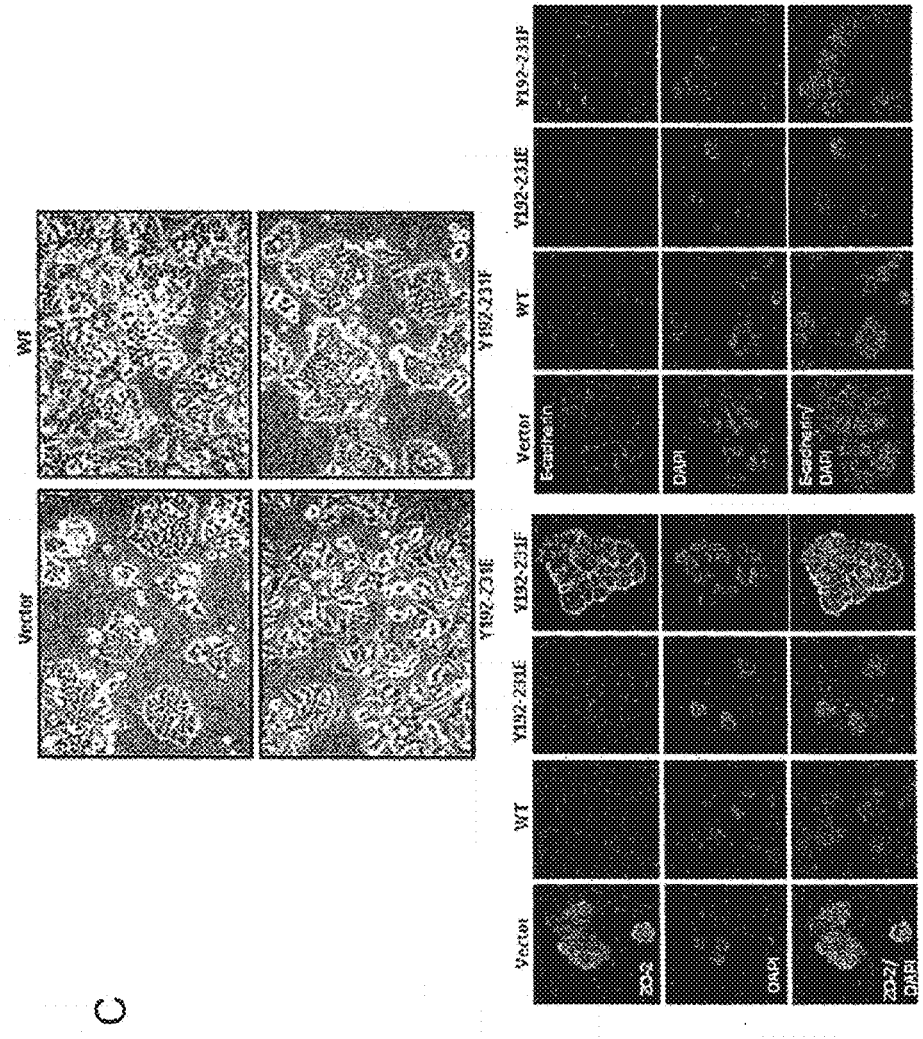
Figure 5:
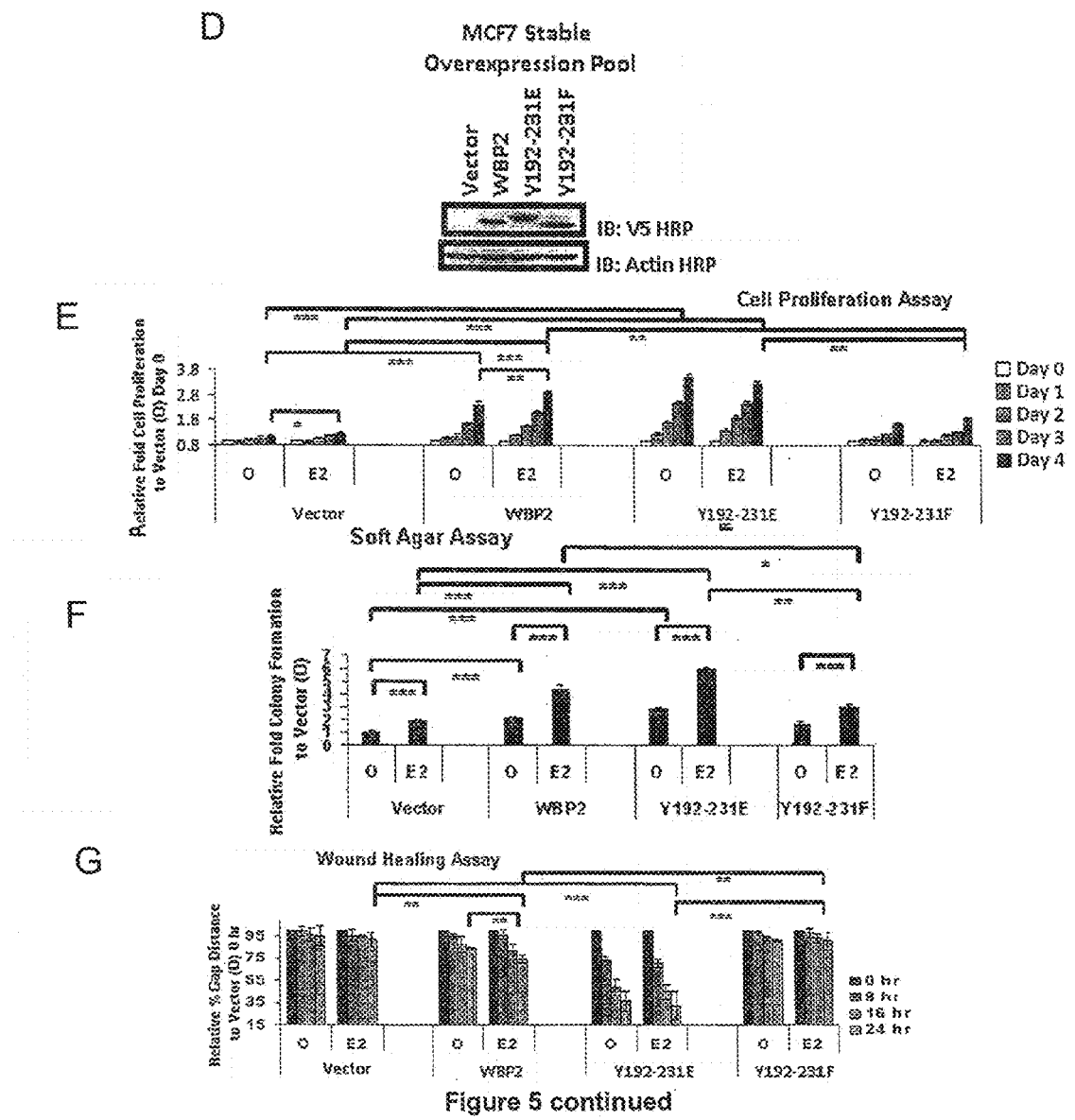
Figure 5:
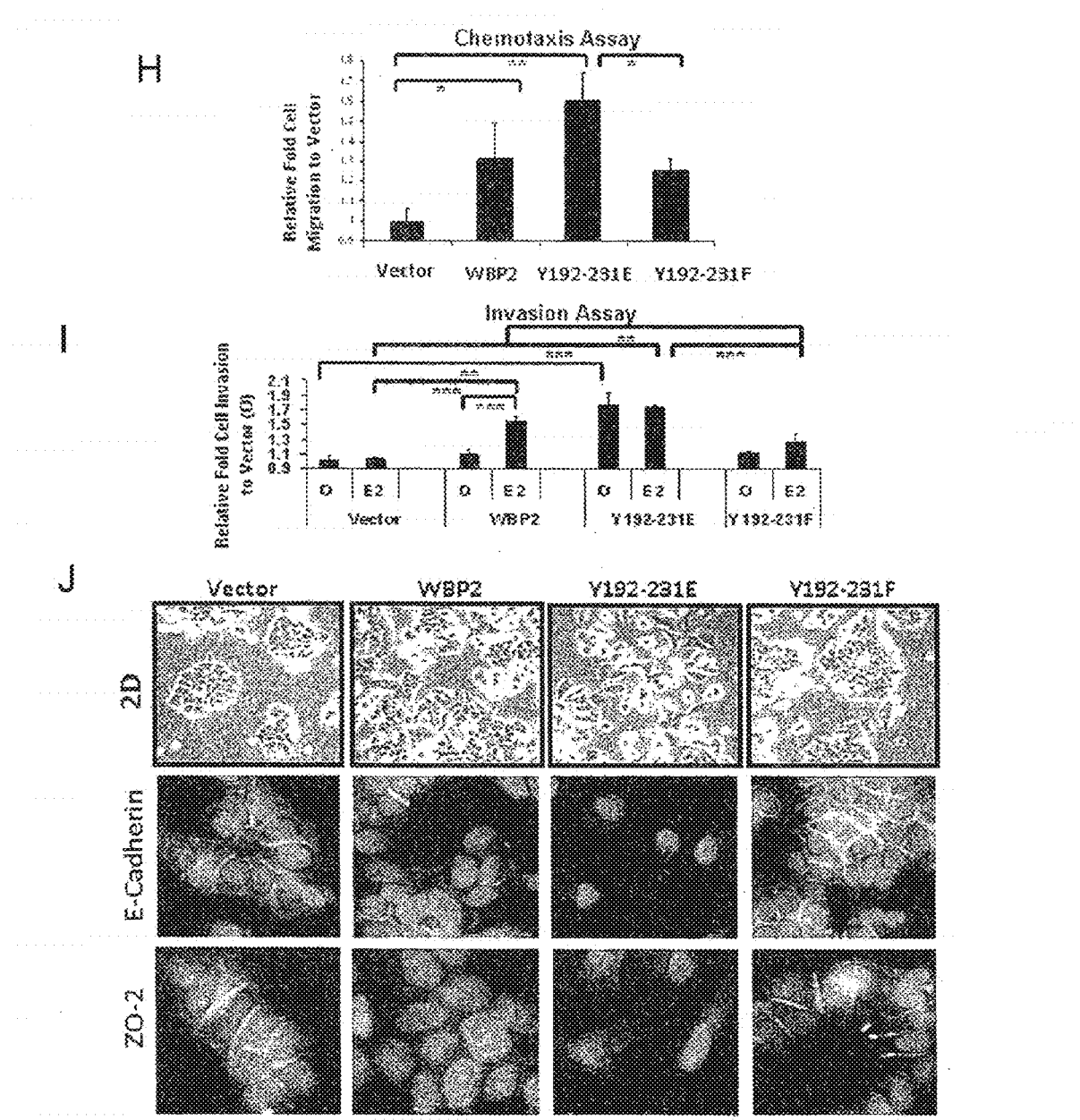
Figure 5:
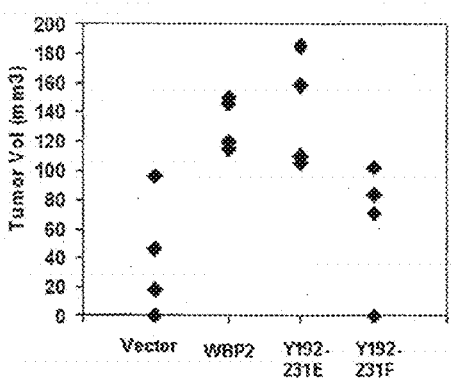
Figure 5:
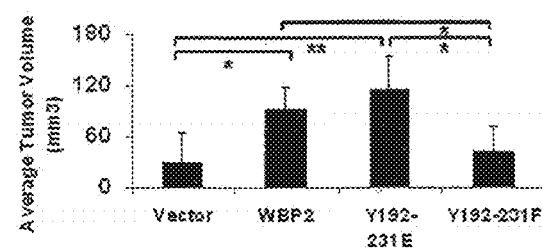
Figure 5:
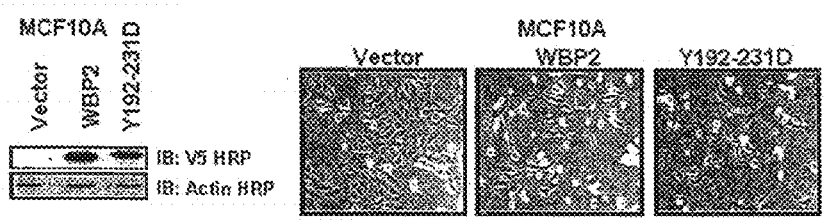
Figure 5:
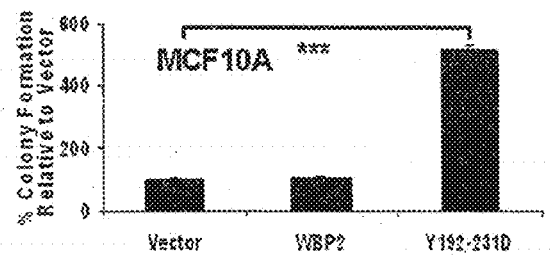

FIG. 5: Roles of WBP2 Phosphorylation in E2-Mediated Breast Cancer Biology

MCF7 were transfected with vector, WBP2-WT, WBP2-Y192-231E or WBP2-Y192-231F and subject to cell proliferation (A), anchorage independent growth (A), wound healing (B) chemotaxis (B) and invasion (B) assays in the presence or absence of 10 nM E2 for the indicate time points. *P<0.05, P<0.01, *P<0.001, Student's t-test (2-tailed). C: Vector, WBP2-WT, WBP2-Y192-231E and WBP2-Y192-231F mutant-expressing MCF7 were examined morphologically in 2D culture and immunofluorescence conducted on EMT markers—ZO-2 and E-Cadherin. D: Immunoblot showing exogenous expression WT, Y192-231E mutant and Y192-231F mutant of WBP2 in stable drug-selected pools of MCF7. MCF7 was transfected with pCEP4, WBP2-WT, WBP2-Y192-231E mutant and WBP2-Y192-231F mutant and selected with hygromycin for 3 weeks and resistant clones were pooled and expanded. These four WBP2 stable transfectants of MCF7 were subject to cell proliferation (E), anchorage independent growth (F), wound healing (G) chemotaxis (H) and invasion (I) assays in the presence or absence of 10 nM E2 for the indicate time points. All data were compared in relative to vehicle-treated vector control at Day 0 or 0 hr. J: They were also examined morphologically in 2D culture (Top Panel) and immunofluorescence conducted on EMT markers—J-Cadherin (Middle Panel) and ZO-2 (Bottom Panel). K: The four WBP2 stable transfectants of MCF7 were subject to xenograft studies in nude mice and tumor formation was assessed and measured on Day 22. Left and right panels respectively show the distribution of tumor volume and average tumor volume of each mouse injected with different stable transfectants; L: Immunoblot showing exogenous expression WT and Y192-231D mutant of WBP2 in stable drug-selected pools of MCF10A (Left Panel). They were examined morphologically in 2D culture (Middle Panel) and subject to anchorage-independent soft agar growth (Right Panel). *P<0.05, P<0.01, *P<0.001, Student's t-test (2-tailed).

Figure 6:
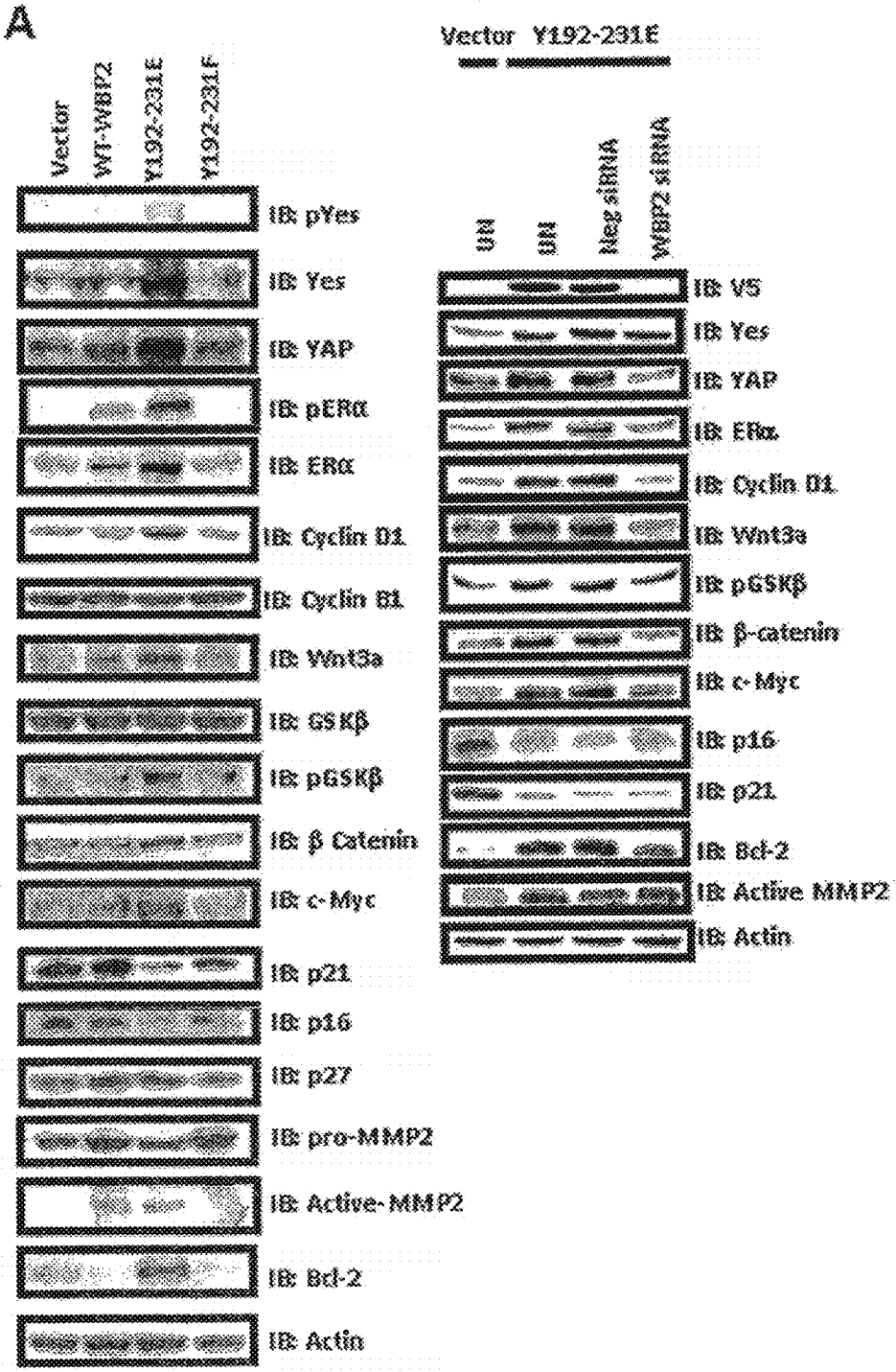
Figure 6:
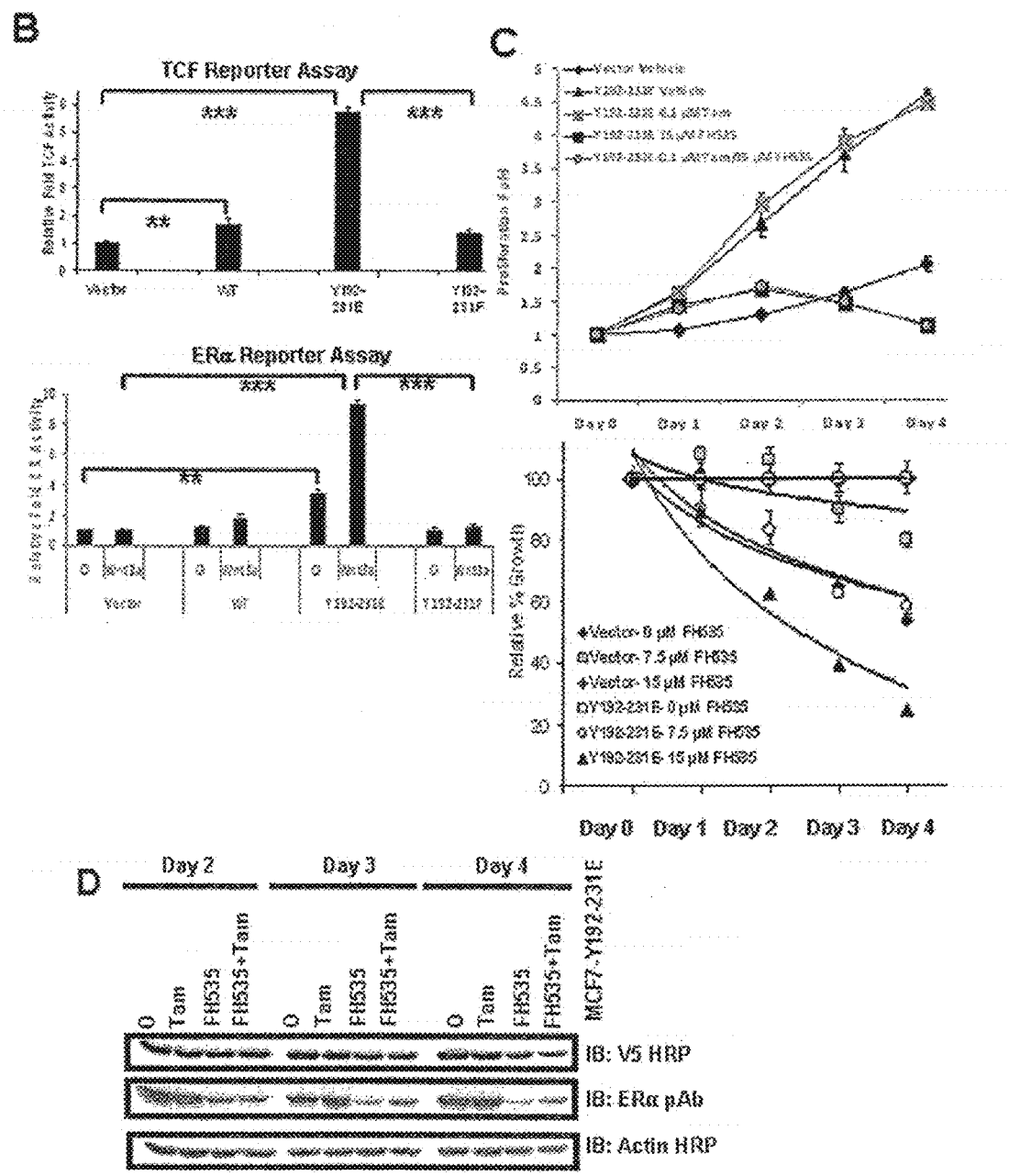

FIG. 6: Potential Mechanisms of Phospho-WBP2-mediated Breast Cancer Biology

A: Whole cell lysates from vector, WBP2-WT, WBP2-Y192-231E mutant and WBP2-Y192-231F mutant expressing MCF7 or Y192-231E mutant expressing MCF7 with WBP2 knockdown were used for IB analysis with antibodies indicated. B: Vector, WBP2-WT, WBP2-Y192-231E mutant or WBP2-Y192-231F mutant-expressing MCF7 were co-transfected with TOPFlash (top panel) or ERE-Luciferase (bottom panel) reporter construct. For cells co-transfected ERE-luciferase, they were either left alone or stimulated with 50 ng/ml Wnt3a ligand for 16 hrs. TCF/ERα luciferase activities in various conditions were then assayed. P<0.01, *P<0.001, Student's t-test (2-tailed). C: Vector or WBP2-Y192-231E mutant-expressing MCF7 were treated with indicated concentrations of Tamoxifen(Tam) and/or FH535. Cell numbers were measured. D: Whole cell lysates from WBP2-Y192-231E mutant-expressing MCF7 treated with 2 µM Tam and/or 15 µM FH5353 were harvested at day 2-4 post-treatment and used for IB analysis with antibodies indicated.

FIG. 7

Sequence of WBP2 (SEQ ID NO: 1) - Y192 and Y231 are highlighted in small boxes. The larger boxes indicate PY motif 1, 2 and 3.

FIG. 8

Construction of prototypes of WBP2-sequence derived peptides. Initially, peptides comprise all PY motifs and tyrosine sites. If these peptides have anti-WBP 2 and anti-breast cancer function, they will be refined (ie., shortened) to determine the Shortest possible peptide that still retain the desired activities. NLS—nuclear localization signal to shunt peptide into the nucleus.

FIG. 9

Xenograft Studies of the Effect of WBP2 and Phosphorylation on Tumor Growth, Five million MCF7 cells expressing vector control, WBP2, Y192-231E phosphomimic and Y192-231F phosphodefective mutants were injected into the flanks of Balb/c nude mice and tumor volume was measured after 3 weeks on Day 22 and Day 32. Top panel shows the distribution of tumor volume by each mouse injected with different stable transfectants at both Day 22 and 32. Bottom panels (left and right) show the average tumor volume generated from mice injected with different stable transfectants. Asterisks indicate statistically significant difference relative to vector control based on Student;s t-test (2-tailed) analysis. (* refers to p<0.05 and ** refers to p<0.01)

FIG. 10

Overexpression of WBP2 and Y192-231D Phosphomimic mutant in MCF10A and Their Functional Studies, Top left: Immunoblot showing exogenous expression WT and Y192-231D mutant of WBP2 in stable drug-selected pools of MCF10A. Top right: Cells were examined morphologically in 2D culture. Cells were subject to cell proliferation assay (Bottom left), anchorage-independent soft agar growth assay (Bottom middle) and cell invasion assay (Bottom right). *p<0.05, p<0.01 and *p<0.001, Student;s t-test (2-tailed)

FIG. 11

Protein Expression and/or Activity Changes Associated with WBP2 Overexpression and Tyrosine Phosphorylation in MCF10A, Whole cell lysates from vector, WBP2-WT and WBP2-Y192-231D-expressing MCF10A were used for immunoblotting analysis with antibodies indicated.

FIG. 12

Expression of WBP2 in HM-1 Undifferentiated vs Differentiated Mouse Embryonic Stem Cells

FIG. 13

Abolishment of WBP2 Tyrosine Phosphorylation Disrupted WBP2-TAZ Interaction in vivo, 293 cells were co-transfected with Flag-TAZ and either vector, WBP2-WT, phosphomimic Y192-231E and phosphodefective Y192-231F mutant and stimulated in the presence or absence of 50 ng/ml EGF. WBP2 was immunoprecipitated using V5 antibody and the immunoprecipitates were then probed for co-immunoprecipitated Flag-TAZ.

FIG. 14

WBP2 Overexpression and Tyrosine Phosphorylation activated E2F Activity, Vector, WBP2-WT, WBP2-Y192-231E and WBP2-Y192-231F-expressing MCF7 were transfected with E2F reporter construct. 48 hr post-transfection, the luciferase activity was assayed and normalized against constitutive TK promoter renilla luciferase activity. Results were expressed as number of fold over vector.

FIG. 15

WBP2 overexpression and tyrosine phosphorylation activated cell cycle progression. MCF7 cells expressing WBP2-WT, WBP2-Y192-231E and WBP2-Y192-231F were pulsed with BrdU for 30 minutes. Cells were harvested after 48 hours. Incorporated BrdU were detected with anti-BrdU fluorescent antibody followed by flow cytometry (left). Bar chart (right) shows the percentages of BrdU positive cells.

FIG. 16

Upregulation of E2F proteins in MCF7 cells overexpressing WBP2 and its phoshomimic mutant. Whole cell lysates from vector, WBP2-WT, WBP2-Y192-231E and WBP2-Y192-231F-expressing MCF7 were used for immunoblotting analysis with antibodies indicated.

FIG. 17

Effect of knockdown of E2F1 and E2F3 on MCF7 cells overexpressing WBP2-Y192-231E. A. MCF7 cells expressing WBP2-Y192-231E were transfected with indicated siRNAs and knockdown efficiency was confirmed using western blotting. B. Cells were co-transfected with indicated siRNAs and E2F reporter plasmid and harvested for luciferase assay after 48 hours. Luciferase readings were normalized against constitutive TK promoter renilla luciferase readings. C. Cells were transfected with indicated siRNAs and BrdU incorporation assay was performed. Percentages of BrdU positive cells relative to control siRNA treated cells were plotted as bar charts. D. Cells were transfected with indicated siRNAs. MTS assay was performed on day 3. Percentages of cell proliferation relative to control siRNA treated cells were plotted as bar charts.

FIG. 18

Whole cell lysates from vector, WBP2-WT, WBP2-Y192-231E mutant and WBP2-Y192-231F mutant expressing MCF7 (A) or Y192-231E mutant expressing MCF7 with WBP2 knockdown (B) were used for IB analysis with antibodies indicated. Their expression levels were quantified in three independent experiments and the averages were presented relative to actin. Representative blots (order in lanes from left to right: vector, WBP2, Y192-231E, Y192F) were presented as insets to the bar graphs. P<0.01, *P<0.001, Student's t-test (2-tailed) relative to vector. Vector, WBP2-WT, WBP2-Y192-231E mutant or WBP2-Y192-231F mutant-expressing MCF7 were cotransfected with TOPFlash(C) or ERE-Luciferase(D) reporter construct. For cells co-transfected ERE luciferase, they were either left alone or stimulated with 50 ng/ml Wnt3a ligand for 16 hrs. TCF(C)/ER☐(D) luciferase activities in various conditions were then assayed and analyzed in relative to untreated vector control. P<0.01, *P<0.001, Student's t-test (2-tailed). E: Vector or WBP2-Y192-231E mutant-expressing MCF7 were treated with indicated concentrations of 2 ☐M tamoxifen (Tam) and/or 15 ☐M FH535 for 4 days. Cell numbers were measured daily and compared in relative to vehicle treated vector-expressing cells on Day 0. F: Vector or WBP2-Y192-231E mutant-expressing MCF7 were treated with indicated concentrations (0-50 ☐M) of FH535 for 2 days. Cell numbers were measured and compared in relative to vehicle-treated cells. Their 1050 were analyzed statistically with SPSS 13.0. G: Whole cell lysates from WBP2-Y192-231E mutant-expressing MCF7 treated with 2 µM Tam and/or 15 µM FH5353 were harvested at day 2-4 post-treatment and used for IB analysis with antibodies indicated. H: Vector or WBP2-Y192-231E mutant-expressing MCF7 were treated with indicated concentrations of 100 nM fulvestrant and/or 15 ☐M FH535 for 4 days. Cell numbers were measured on day 2 and day 4 and compared in relative to vehicle-treated control at each day (Top Panel). These treated cells were harvested for IB analysis with antibodies indicated (Bottom Panel).

FIG. 19

Whole cell lysates from vector, WBP2-WT, WBP2-Y192-231E mutant and WBP2-Y192-231F mutant-expressing MCF7 (A) or Y192-231E mutant expressing MCF7 with WBP2 knockdown (B) were used for IB analysis with antibodies indicated. Their expression levels were quantified in three independent experiments and the averages were presented relative to actin. Representative blots (order in lanes from left to right: vector, WBP2, Y192-231E, Y192F) were presented as insets to the bar graphs. P<0.01, *P<0.001, Student's t-test (2-tailed) relative to vector.

DETAILED DESCRIPTION

The present technology relates to the discovery of two tyrosine phosphorylation sites on WBP-2, which have been demonstrated to:
1. Regulate its ER, TCF/b-catenin and E2F co-activation functions
2. Modulate nuclear translocation of WBP2
3. Affect breast cancer biology (in terms of EMT, cell proliferation and invasion)

Detection of phosphorylation at site-specific locations Y192 or Y129 and Y231 of WBP2 (SEQ ID NO. 1) with aptamer or antibodies such as monoclonal antibodies or polyclonal antibodies or specific probes or primers can be used to diagnosis cancer or prognoses of suitable therapies for cancer. Further an agent that interferes with phosphorylation of tyrosine Y192 and/or Y231 in the polypeptide of SEQ ID NO. 1. may be used as a suitable treatment of cancer. In one embodiment the cancer is breast cancer. In another embodiment the cancer is lung cancer. The technology is suitable with other cancers that are dependent on EGFR, c-Src, c-Yes, ER, Wnt or E2F such as Liver cancer; head and neck cancer; colorectal cancer; bone cancer as well as others known to those skilled in the art.

```
SEQ ID NO. 1:
MALNKNHSEGGGVIVNNTESILMSYDHVELTFNDMKNVPEAFKGTKKGT

VYLTPYRVIFLSKGKDAMQSFMMPFYLMKDCEIKQPVFGANYIKGTVKA

EAGGGWEGSASYKLTFTAGGAIEFGQRMLQVASQASRGEVPSGAYGYSY

MPSGAYVYPPPVANGMYPCPPGYPYPPPPPEFYPGPPMMDGAMGY*VQP

PPPPYPGPMEPPVSGPDVPSTPAAEAKAAEAAASAY*YNPGNPHNVYMP

TSQPPPPPYYPPEDKKTQ
```

Interference of WBP2 tyrosine phosphorylation at Y192 or interference of WBP2 tyrosine phosphorylation at Y192 and Y231 with an agent can slow or stop cancer progression. Embodiments include the agent can slow or stop breast cancer or lung cancer progression. Preferred agents of interference may include: monoclonal antibodies, peptides, small molecules, siRNA designed to suppress the expression of WBP2 such as siWBP-2; aptamers and other reagents that interfere with Y192 phosphorylation of WBP2 or Y192 and Y231 phosphorylation on WBP2 for breast cancer treatment WBP2 as a drug target and biomarker for cancer We have identified WBP2 as a downstream target of EGF/EGFR and E2/ER signaling. We have also identified c-Yes and c-Src tyrosine kinases as putative upstream kinase of WBP2 and may therefore regulate WBP2 activity and function.

We have identified WBP2 to be phosphorylated at Y192 and Y231 and shown that WBP2 expression and phosphorylation conferred growth factor independence leading to increased growth, proliferation, migration and invasion of ER+ breast cancer cells. Silencing of WBP2 using siRNA and shRNA can abrogate biological functions of triple-negative breast cancer cells in vitro including proliferation, growth, migration and invasion.

We discovered that tyrosine phosphorylation at Y192 and Y231 regulates WBP2 function, localization and interaction with target proteins such as ER and possible other oncogenes/tumor suppressors.

We showed that WBP2 and its tyrosine phosphorylation activated ER, TCF/b-catenin and E2F transcriptional activities. We provided evidence that WBP2's role in the activation of transcriptional activities was due to but not necessarily limited to WBP2-mediated up-regulation of the expression and sometimes activation of multiple oncogenes including c-myc, wnt3a, b-catenin, c-yes, YAP, ER, BCL2 and other metastasis-associated proteins including the metallo-proteases. WBP2 also suppressed the expression of tumor suppressors and other growth modulators like p21 and p16.

We found over-expression of WBP2 in breast cancer cell lines and tissues compared to normal cells and tissues. From about 376 clinical samples, we discovered that ¾ or more non-cancer tissues (normal, hyperplasia and benign) had undetectable level of nuclear WBP2 whereas the majority of cancer tissues (ductal carcinoma in situ, invasive carcinoma and metastatic carcinoma) had moderate to high nuclear level of WBP2.

We have shown from study of in vitro breast cancer cell lines that the nuclear species of WBP2 were tyrosine phosphorylated at Y192/231 but the cytosolic WBP2 were largely non-phosphorylated.

WW-binding protein 2 (WBP2) has been demonstrated in different studies to be a tyrosine kinase substrate, to activate ERα/PR transcription and to play a role in breast cancer. However, the role of WBP2 tyrosine phosphorylation in regulating ER function and breast cancer biology is unknown. Here, we established WBP2 as a tyrosine phosphorylation target of estrogen signaling via EGFR crosstalk. Using dominant negative, constitutively active mutants, RNAi and pharmacological studies, we demonstrated that phosphorylation of WBP2 at Tyr192 and Tyr231 could be regulated by c-Src and c-Yes kinases. We further showed that abrogating WBP2 phosphorylation impaired >60% of ERα reporter activity putatively by blocking nuclear entry of WBP2 and its interaction with ERα. Compared to vector control, overexpression of WBP2 and its phospho-mimic mutant in MCF7 resulted in larger tumors in mice, induced loss of cell-cell adhesion, enhanced cell proliferation, anchorage-independent growth, migration and invasion in both estrogen-dependent and -independent manner, events of which could be substantially abolished by overexpression of phosphorylation-defective mutant. Hormone independence of cells expressing WBP2 phospho-mimic mutant was associated with heightened ERα and Wnt reporter activities. Wnt/β-catenin inhibitor FH535 blocked phospho-WBP2-mediated cancer cell growth more pronouncedly than tamoxifen and fulvestrant, in part by reducing the expression of ERα. Wnt pathway is likely to be a critical component in WBP2-mediated breast cancer biology.

Accordingly one aspect of the invention includes a method of detecting cancer in a patient comprising the steps of:
c) Measuring an amount of a polypeptide of SEQ ID No. 1 with a phosphorylated tyrosine at Y192 in a first sample isolated from the patient; and
d) Comparing the amount of polypeptide of SEQ ID No. 1 with a phosphorylated tyrosine at Y192 in the sample to an amount of polypeptide of SEQ ID No. 1 with a phosphorylated tyrosine at Y192 in a second sample isolated from normal, non-cancerous cells,
wherein an amplified amount of polypeptide of SEQ ID No. 1 with a phosphorylated tyrosine at Y192 in the first sample relative to the amount of polypeptide of SEQ ID No. 1 with a phosphorylated tyrosine at Y192 in the second sample indicates cancer is present in the first sample.

Preferably the amount of the polypeptide of SEQ ID No. 1 with a phosphorylated tyrosine at Y192 in the first and second sample also detects phosphorylation of tyrosine at Y231 of the polypeptide of SEQ ID No. 1 wherein an amplified amount of polypeptide of SEQ ID No. 1 with a phosphorylated tyrosine at Y192 and Y231 in the first sample relative to the amount of polypeptide of SEQ ID No. 1 with a phosphorylated tyrosine at Y192 and Y231 in the second sample indicates cancer is present in the first sample.

Preferably the cancer is breast cancer and lung cancer.

Preferably the amount of the polypeptide of SEQ ID No. 1 with a phosphorylated tyrosine is measured with an isolated phosphorylation site-specific antibody that specifically binds to a WW-domain binding protein of SEQ ID. NO. 1 only when the polypeptide is phosphorylated at the tyrosine Y192 or the tyrosine Y192 and the tyrosine Y231 wherein the antibody does not bind the polypeptide of SEQ ID No. 1 when it is not phosphorylated at said tyrosine.

Preferably the method further comprising the steps of:
c) bringing the polypeptide of SEQ ID No. 1 into contact with a polynucleotide probe or primer comprising a polynucleotide sequence capable of hybridising selectively to the polypeptide of SEQ ID No. 1 only when the polypeptide is phosphorylated at the tyrosine Y192 or the tyrosine Y192 and the tyrosine Y231 under suitable hybridising conditions; and
d) detecting any duplex formed between the probe or primer and the polypeptide of SEQ ID No. 1 phosphorylated at said tyrosine.

6. The method of any one of claims 1 to 3 whereby the amount of the polypeptide of SEQ ID No. 1 with a phosphorylated tyrosine is measured with an isolated phosphorylation site-specific aptamers that specifically binds to a WW-domain binding protein of SEQ ID. NO. 1 only when the polypeptide is phosphorylated at the tyrosine Y192 or Y231 or the tyrosine Y192 and the tyrosine Y231 wherein the aptamers does not bind the polypeptide of SEQ ID No. 1 when it is not phosphorylated at said tyrosine.

Another aspect of the invention includes an agent to interfere with phosphorylation of tyrosine Y192 and/or Y231 in the polypeptide of SEQ ID NO. 1.

Preferably the agent comprises an isolated phosphorylation site-specific antibody that specifically binds to a WW-domain binding protein of SEQ ID. NO. 1 only when the polypeptide is phosphorylated at the tyrosine Y192, Y231 or the tyrosine Y192 and the tyrosine Y231 wherein the antibody does not bind the polypeptide of SEQ ID No. 1 when it is not phosphorylated at said tyrosine.

Preferably said antibody is an immunoglobulin comprising an immunoglobulin heavy chain.

Preferably said antibody is an immunoglobulin comprising an immunoglobulin light chain.

Preferably the immunoglobulin is an IgG1 kappa immunoglobulin.

Preferably the immunoglobulin comprises a human IgG1 constant region within a heavy chain of the immunoglobulin and a human constant region within a light chain of the immunoglobulin.

In one embodiment the immunoglobulin comprises fully or partially human framework regions within the heavy chain and within the light chain.

In one embodiment the immunoglobulin comprises murine framework regions within the heavy chain and within the light chain.

Figure 8:
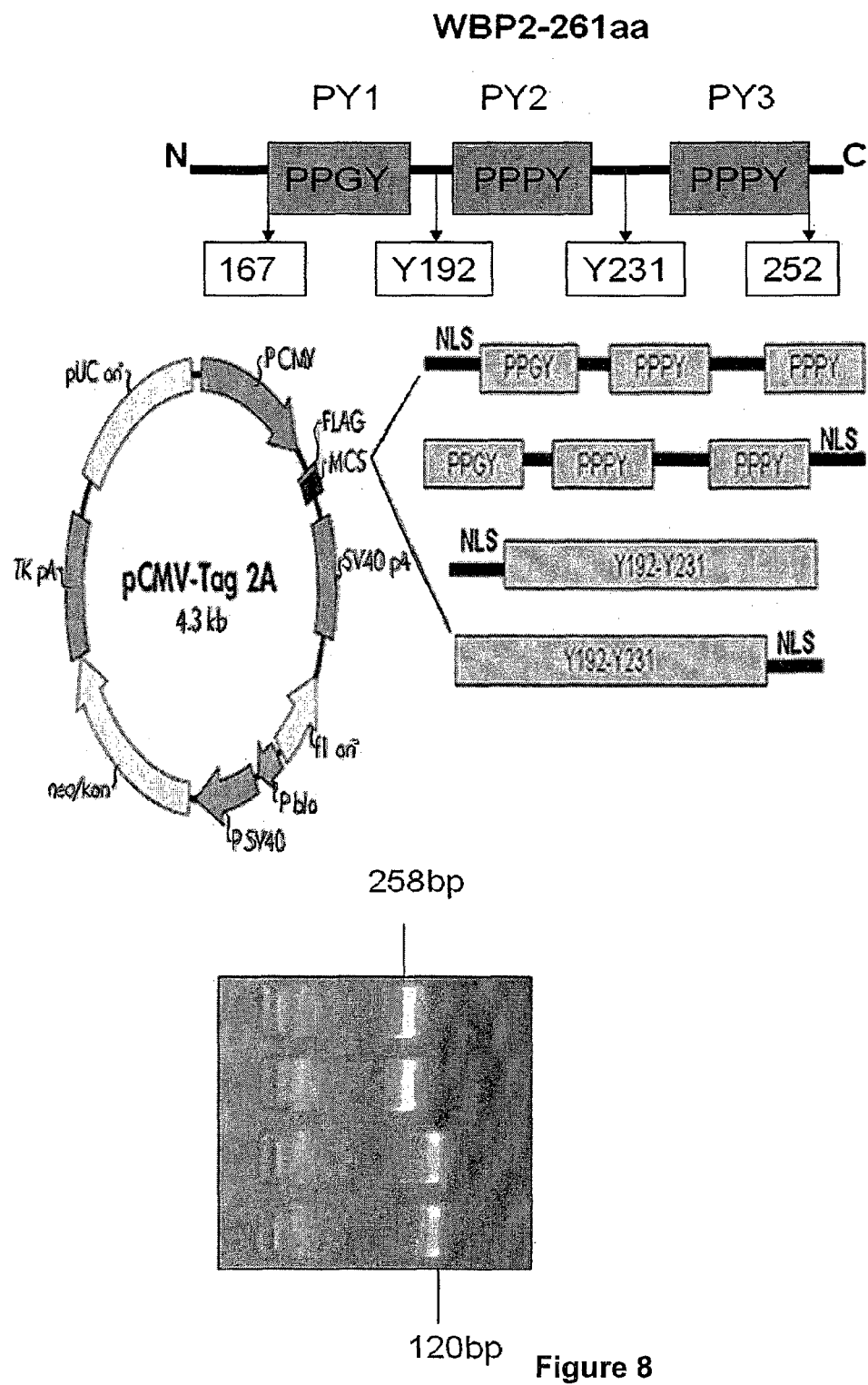

In one embodiment the agent may be a refined peptide based on a sequence flanking the phosphorylated tyrosine Y192 or, Y231 or Y192 and Y231 or PY1, PY2 and/or PY3. The method of refining the peptide is described in FIG. 8. Whereby construction of prototypes of WBP2-sequence derived peptides includes the phosphorylated tyrosine Y192 or, Y231 or Y192 and Y231 and the amino acids flanking either side of the phosphorylated tyrosine Y192 or, Y231 or Y192 and Y231. Initially, peptides comprise all PY motifs and tyrosine sites. If these peptides have anti-WBP 2 and anti-breast cancer function, they will be refined (ie., shortened) to determine the Shortest possible peptide that still retain the desired activities. The peptides further include a nuclear localization signal (NLS) to allow them to be capable or shunting the peptide into the nucleus. Any suitable NLS known to those in the art would be suitable in the examples used the NLS sequence was (PKKKRKV) specifically

```
Sense: 5'-CCCAAGAAGAAGCGAAAGGTC-3'

Antisence: 5'-GACCTTTCGCTTCTTCTTGGG-3'
```

Examples of the peptides include:

```
                                         SEQ ID NO. 3
[NLS]-PPGYPPPYPPPY

SEQ ID NO. 4
PPGYPPPYPPPY-[NLS]

SEQ ID NO. 5
[NLS]-YVQPPPPPYPGPMEPPVSGPDVPSTPAAEAKAAEAAASAY

SEQ ID NO. 6
YVQPPPPPYPGPMEPPVSGPDVPSTPAAEAKAAEAAASAY-[NLS]
```

Preferably the antibody is able to be produced in a cell line.

Preferably the agent comprises an isolated phosphorylation site-specific aptamers that specifically binds to a WW-domain binding protein of SEQ ID. NO. 1 only when the polypeptide is phosphorylated at the tyrosine Y192 or the tyrosine Y192 and the tyrosine Y231 wherein the aptamers does not bind the polypeptide of SEQ ID No. 1 when it is not phosphorylated at said tyrosine.

In one embodiment the agent comprises a small interfering RNA such as SEQ ID NO. 2. (5'-AGCAUCCGCUGU-CCGAACUCAAUGG-3')

Another aspect of the invention includes an agent of the invention for use in the treatment of cancer.

Preferably the agent of the invention is for use in the treatment of breast cancer and lung cancer.

Preferably the agent of the invention further comprising the compound of FH535 of formula 1.

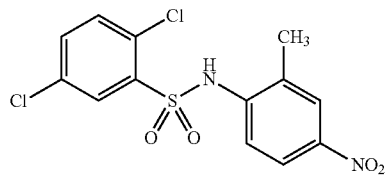 [SMILES: Cc1cc([N+](=O)[O-])ccc1NS(=O)(=O)c1cc(Cl)ccc1Cl]

Another aspect of the invention includes a composition comprising the agent of the invention and the compound of FH535 of formula 1.

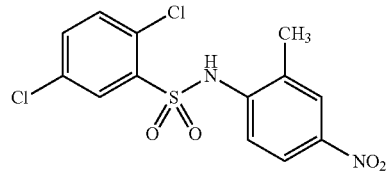 [SMILES: Cc1cc([N+](=O)[O-])ccc1NS(=O)(=O)c1cc(Cl)ccc1Cl]

Another aspect of the invention includes a method of treating a patient afflicted with cancer, comprising the steps of:

(a) administering to the patient an agent to interfere with phosphorylation of tyrosine Y192 and/or Y231 in the polypeptide of SEQ ID NO. 1.

We propose to measure nuclear WBP2 expression as a more accurate method for cancer diagnosis and prognosis. WBP2 is a transcriptional regulator and aberrant expression of nuclear WBP2 is likely to be a causative mechanism in breast cancer.

We disclose 2 phosphorylation site of WBP2—Y231 and Y192 and in addition showed that phosphorylation of these 2 tyrosine sites regulates breast cancer biology.

Nuclear expression level of WBP2 can be used as a diagnostic or prognostic biomarker for cancer, particularly Breast cancer. Detection kit for WBP2—be it nucleic acid, antibody, aptamer or other reagent-based could be used for early detection/screening of breast cancer, confirmation of histopathologically uncertain cases or suspicious cases following mammography. Total WBP2 or nuclear expression of WBP2 may also be used to predict response to drug.

Phosphorylation site-specific antibodies, aptamers or other reagents may be used to detect phosphorylated WBP2 as a diagnostic or prognostic feature in breast cancer and cancers from other origins. This is supported by our data which showed that WBP2 is a phosphorylation target of EGFR, Src and Yes. As these tyrosine kinases that have been reported to be aberrant in terms of expression or activity in many human cancers, it means that any cancers with any of these kinase activities heightened is likely to have increased WBP2 phosphorylation.

Modulation of WBP2 expression by any means including but not limited to RNAi and small molecules, can be exploited to block cancer growth, proliferation, migration, invasion or metastasis either singly or in combination with other targets. An example of an siRNA is SEQ ID NO. 2: 5'-AACGTGCCAGAAGCCTTCAAACCTGTCTC-3', An example of an effective composition was an agent that interfered with the phosphorylation of WBP2 tyrosine at Y192 and Y231 and compound of FH535 of formula 1

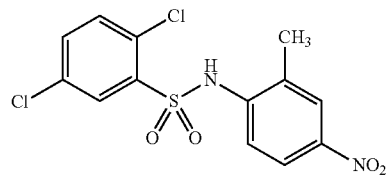 [SMILES: Cc1cc([N+](=O)[O-])ccc1NS(=O)(=O)c1cc(Cl)ccc1Cl]

A β-Catenin/Tcf Inhibitor, FH535, Molecular Formula: $C_{13}H_{10}Cl_2N_2O_4S$, Molecular Weight: 361.2 g/mol.

Interference of WBP2 tyrosine phosphorylation at Y192 and Y231 or WBP2 nuclear localization could be used to block breast cancer growth, proliferation, migration, invasion and/or metastasis either directly or by regulating the expression or function of other oncogenes and tumor suppressors. In addition to small molecules, we propose that protein sequences comprising the PY motifs and/or sequence flanking and including Y192 and Y231 could be exploited to block WBP2 phosphorylation and therefore be used for breast cancer treatment either singly or in combination with other therapeutic strategies. We further propose that sequences apart from PY motifs, Y192 and Y231 derived from WBP2 could be exploited for breast cancer treatment either singly or in combination with each other or with other therapeutic strategies.

Our data provides direct scientific evidence on the role of i) WBP2 through overexpression and knock down studies in at least 2 breast cancer cell lines and ii) the two tyrosine sites on breast cancer biology. For the latter, we showed that mutations of the 2 tyrosine sites reduced various aspects of breast cancer biology in breast cancer cells. Since tyrosine phosphorylation can block WBP2 function in cancer biology, these 2 sites are effective sites for targeted cancer therapy.

WBP2 expression could conceivably serve as a biomarker. However, as expression does not necessarily correlate with activity, a more important determinant of disease phenotype is needed.

Hence, there is no doubt that examining the phosphorylation status of WBP2 is likely to be a more relevant (therefore more superior) diagnostic feature than just its expression. Our data showed that WBP2 is a phosphorylation target of ER, EGFR, Src, Yes. These are all tyrosine kinases that have been reported to be aberrant in terms of expression or activity in many human cancers. What this means is that any cancers with any of these kinase activity heighted is likely to have increased WBP2 phosphorylation. Hence, the application of phosphorylation site-specific antibodies extends beyond breast cancer. In fact, our data shows that the nucleus species of WBP2 (ie., the functional form of WBP2) is tyrosine phosphorylated whereas the bulk of WBP2 (probably the non-functional form) resides in the cytosolic compartment. This means that the phosphorylation specific WBP2 antibodies would detect the nuclear/active form of WBP2 that are more relevant to cancer than the non-active ones picked up by non-phosphorylation specific WBP2 antibodies.

Expression level of WBP2 has also been detected to be lower in normal lung cells compared to a panel of lung cancer cell lines. In some lung cancer cell lines, WBP2 was found to be constitutively phosphorylated at tyrosine residues.

Although transcription co-activator WBP2 has been demonstrated to activate ER/PR function, its mode of regulation, impact on breast cancer biology and underlying mechanisms are unknown. We established WBP2 as a tyrosine phosphorylation target in estrogen signaling via EGFR crosstalk. c-Yes-mediated phosphorylation of WBP2 at Tyr192 and Tyr231 depended on EGFR activation whereas c-Src may act directly or upstream of EGFR. Abrogating WBP2 phosphorylation impaired its coactivator activity on ERα transactivation by blocking nuclear entry and interaction of WBP2 with ERα. Overexpression of wild-type and phospho-mimic mutant of WBP2 in MCF7 induced loss of cell-cell adhesion proteins, enhanced cell proliferation, anchorage-independent growth, migration and invasion in both estrogen-dependent and independent manner, events of which could be substantially abolished by overexpression of phosphorylation-defective mutant. Phospho-mimic WBP2 potently activated the Wnt pathway and enhanced Wnt-mediated activation of ERα function, potentially by up-regulating the expression of ERα, β-catenin and Wnt3a. Wnt signaling was subsequently demonstrated to be critical in WBP2-mediated breast cancer cell proliferation. Our findings provide molecular insights into the intricate interaction and signaling networks involving WBP2, ERα and Wnt. WBP2 joins the rank of nuclear hormone receptor coactivators that are increasing implicated in breast cancer.

Preferred Embodiments

WBP2—A Novel Phospho-Oncoprotein in Breast Cancer

WBP2 (WW-domain Binding Protein 2) was first implicated in breast cancer through our previous phosphoproteomics screen on the MCF10AT xenograft-derived isogenic cell line model of human breast cancer progression, where WBP2 was found to be differentially phosphorylated during breast cancer development. We have also shown it to be an authentic tyrosine phosphorylation target of EGFR signaling. In a follow up study, we found that WBP2 expression was low or undetectable in normal breast epithelial cells but overexpressed in breast cancer progression model as well as multiple breast cancer cells of various subtypes. Therefore, we aim to investigate the oncogenic role of WBP2 in the growth and progression of human breast cancer through its protein overexpression and tyrosine phosphorylation. We first mapped the EGF-dependent tyrosine phosphorylation sites on WBP2 and identified a member of the Src family of tyrosine kinases as the putative upstream kinase of WBP2. Next, we found that Estrogen (E2) stimulation could similarly induce tyrosine phosphorylation of WBP2 via a crosstalk between EGFR and ER pathways. Subcellular fractionation study revealed a phosphorylation-dependent nuclear entry of WBP2 upon E2 or EGF stimulation. Consistent with the reported role of WBP2 as a coactivator for nuclear hormone receptor (ERα/PR), abrogation of tyrosine phosphorylation on WBP2 significantly impaired the E2-induced ER transactivation through reduced E2/EGF-stimulated nuclear entry of WBP2 and in vivo E2-dependent WBP2-ER interaction. Stable overexpression of wild type and phospho-mimic mutant of WBP2 in ER-positive MCF7 breast cancer cell enhance its cell proliferation, anchorage-independent growth in soft agar, cell migration and cell invasion in the E2-independent and/or E2-dependent manner. These cellular processes could be inhibited, at least in part, by the phosphorylation-defective mutant of WBP2. Potential mechanisms of WBP2-mediated oncogenic transformation will be presented.

We also found that stable knock down of WBP2 in ER-negative breast cancer cells, MDA-MB-231 also profoundly inhibited breast cancer cellular processes such as growth, proliferation, migration and invasion.

Collectively, our findings have uncovered the potential of WBP2 as a novel phospho-oncoprotein in ER+ and ER− breast cancer, It is conceivable that WBP2 and/or its tyrosine phosphorylated form could serve as a potential prognostic marker or therapeutic target for human breast cancer as well as other cancer types such as lung cancer.

Materials and Methods

Antibodies

Through NeoMPS, Inc, we generated in-house polyclonal antibodies against WBP2 based on a 17 amino acid (N'-NDMKNVPEAFKGTKKGT-C'; SEQ ID NO: 7) peptide sequence reported in another study (11), which were affinity purified and stringently validated via comparative immunoblotting with pre-immune serum, in the presence of WBP2- specific and control peptides, reciprocal immunoprecipitation of exogenously expressed tagged WBP2 protein and immunoblotting with anti-tag and anti-WBP2 antibodies (data not shown). Anti-WBP2 mouse monoclonal was purchased from Abnova Corp., Taipei, Taiwan; anti-PY20-HRP, anti-EGFR, anti-β-catenin and anti-Yes mouse monoclonal were obtained from BD-Biosciences, San Diego, Calif., USA; anti-Actin-HRP, anti-ERa, anti-phospho-ERα-S118, anti-Src, anti-cyclin B1, anti-c-Myc, anti-p21, anti-p16, anti-p27, anti-MMP2 and anti-ZO-2 rabbit polyclonal, anti-ERα and anti-cyclin D1 mouse monoclonal, anti-GADPH and anti-vimentin goat polyclonal were obtained from Santa Cruz Biotechnology Inc., Santa Cruz, Calif., USA; anti-phospho-Src-Y416, anti-EGFR, anti-YAP1, anti-Histone 2A, anti-E-cadherin, anti-Wnt3a, anti-GSKβ, anti-phospho-GSKβ-S9, anti-Bcl2, anti-Akt and anti-pERK1/2-Thr202/Tyr204 rabbit polyclonal, anti-pAkt-S473 and anti-ERK1/2 mouse monoclonal and were obtained from Cell Signaling Technology Inc., Danvers, Mass., USA; anti-V5 mouse monoclonal and anti-V5-HRP were obtained from Invitrogen Corp., Carlsbad, Calif., USA; anti-Yes rabbit polyclonal was obtained from Millipore corp., Billerica, Mass., USA; anti-phospho-FAK1-Y397 rabbit polyclonal was obtained from Abcam, Cambridge, UK; Anti-mouse, anti-rabbit and anti-goat horseradish peroxidase (HRP) conjugates were purchased from Sigma-Aldrich, St. Louis, Mo., USA.

Plasmids and Reporters cDNA for wild-type-WBP2 was from Origene (Rockville, Md.) and subcloned into pcDNA™ 6.2-Directional-TOPO® vector and pCEP4 (Invitrogen). All Y→F mutations were generated using the QuikChange II XL Site-Directed Mutagenesis Kit (Stratagene).

These were kind gifts—Src-wild-type (WT), constitutively-active (CA) and dominant-negative (DN)-pSGT from Sarah Courtneidge, EMBL; Yes-WT and CA (Y357F) from Marius Sudol, Danville, Pa., USA; 2XERETATA-Firefly Luc and 2×PRE-TATA-Firefly Luc from Dean P. Edwards, Houston, Tex., USA; TOPFlash reporter plasmid from Yoshiaki Ito, Singapore. pRL-TK was purchased from Promega.

cDNA for wild-type-WBP2 was from Origene, Rockville, Md., USA and subcloned into pcDNA™ 6.2-Directional-TOPO® vector and pCEP4 (Invitrogen). All mutations were generated using the QuikChange II XL Site-Directed Mutagenesis Kit (Stratagene, Agilent Technologies Inc., Santa Clara, Calif., USA). These were kind gifts—Src-wild-type (WT), constitutively-active (CA-Y529F) and dominant-negative (DNK295M)-pSGT from Sarah Courtneidge, EMBL, USA; Yes-WT and CA (Y537F) from Marius Sudol, Danville, Pa., USA; 2XERE-TATA-Firefly Luc and 2×PRE-TATA-Firefly Luc from Dean P. Edwards, Houston, Tex., USA; TOPFlash reporter plasmid from Yoshiaki Ito, Singapore. pRL-TK was purchased from Promega, corp., Madison, Wis., USA.

Cell Culture and Transfection

MCF7, MDA-MB231, T47D, HeLa and A431 were from American Type Culture Collection. MCF7, HeLa and MDA-MB231 were maintained in RPMI1640 (Sigma) containing 10% FBS (Hyclone) and 100 U Penicillin/Streptomycin (Invitrogen). T47D was maintained in RPMI1640 containing 10% FBS, 10 µg/ml Insulin (Sigma) and 100 U Penicillin/Streptomycin Pen/Strep. A431 were maintained in DMEM (Sigma) containing 10% FBS and 100 U Penicillin/Streptomycin. Cell lines were authenticated by short tandem repeat (STR) profiling carried out by the suppliers. The ERα status of MCF7 and T47D ER-positive breast cancer cell lines were authenticated by western blot to determine ERα expression, and all cells were tested to be *Mycoplasma*-free. All experiments were carried out between passages 1 and 10. Cells in 60 mm dish were transfected with 4 µg plasmids/100 nM siRNA using lipofectamine 2000 (Invitrogen) according to the manufacturer's instructions.

Ligands and Drug Treatment

For all experiments involving estrogen/progesterone (Sigma), MCF7 and T47D were cultured in Phenol-Red Free RPMI1640 (Sigma) containing 5% Charcoal-dextran Stripped FBS (Hyclone) for at least 2 days before stimulation. EGF was from Millipore, Wnt3a ligand was from R&D systems, Tamoxifen and FH535 were from Sigma while Iressa and AZD0530 were from AstraZeneca. Fresh hormone/drug was replenished every day for treatment that last for more than 1 day.

Cell lysis, SDS-PAGE and Immunoblotting
Cell Culture, Ligand/Drug Treatments and Lysis MCF7, MDA-MB231, T47D, HeLa and MCF10A were from American Type Culture Collection. MCF7, HeLa and MDA-MB231 were maintained in RPMI1640 (Sigma) containing 10% FBS (Hyclone) and 100 U Penicillin/Streptomycin (Invitrogen). T47D was maintained in RPMI1640 containing 10% FBS, 10 µg/ml Insulin (Sigma) and 100 U Penicillin/Streptomycin. MCF10A were maintained in DMEM/F12 (Sigma) containing 5% Horse serum with additives previously described (17). For all experiments involving estrogen/progesterone (Sigma), MCF7 and T47D were cultured in Phenol-Red Free RPMI1640 (Sigma) containing 5% Charcoal-dextran Stripped FBS (Thermo Scientific Hyclone, South Logan, Utah, USA) for at least 2 days before stimulation. EGF was from Millipore, Wnt3a ligand was from R&D systems Inc., Minneapolis, Minn., USA, tamoxifen, fulvestrant and FH535 were from Sigma while Iressa and AZD0530 were from AstraZeneca Singapore Pte Ltd, Singapore. Fresh hormone/drug was replenished every day for treatment that last for more than 1 day. Cell lysis was performed as per previous report (18).

Immunoprecipitation/Co-Immunoprecipitation

Immunoprecipitation and Immunoblotting were carried out as previously described (19). For co-immunoprecipitation, cells were lysed in ice-cold buffer (50 mM Tris, pH7.5; 150 mM NaCl; 1 mM EDTA; 10% glycerol; 0.5% Nonidet P40; 0.5% Triton X-100; 50 mM NaF; 1× protease inhibitor; 1 mM $Na_3VO_4$) and incubated on ice for 15 min for complete lysis. Prior to immunoprecipitation, 500-1000 µg of lysates were precleared by incubation with 50 µl of 50% slurry of anti-mouse/rabbit-IgG agarose (Sigma) for 1 hr at 4° C. Meanwhile, equivalent amount of anti-mouse/rabbit-IgG agarose was blocked with 5% BSA overnight, 4° C. Precleared lysates were then incubated with 1-2 µg antibodies overnight at 4° C. Immune complexes were then captured by incubation with preblocked anti-mouse/rabbit-IgG agarose for 2 hr at 4° C. Before western blotting, immunoprecipitates were washed extensively for 4×5 min each with buffer (50 mM Tris, p117.5; 150 mM NaCl; 1 mM EDTA; 10% glycerol; 0.5% NP40; 0.5% Triton X-100; 1 mM $Na_3VO_4$).

Transient and Stable Transfection

For transient transfection, cells were seeded at 70-80% confluency in 60-mm dish in antibiotic-free medium one day before transfection and transfected with 4 µg plasmid DNA or 50-100 nM siRNA and 12 µl lipofectamine 2000 (Invitrogen) according to the manufacturer's instructions. Cells were harvested 24-48 hr post-transfection. For reverse transfection, cells were transfected while they were still in suspension (i.e. after trypsinization and prior to plating). For stable transfection, MCF7 or MCF10A was transfected with pCEP4 vector, WBP2-WT, WBP2-Y192-231E, WBP2-Y192-231D and WBP2-Y192-231F/pCEP4. 48 hrs post-transfection, cells were exposed to Hygromycin (Invitrogen) [250 □g/ml for MCF7 and for 50 ng/ml MCF10 A1] for 3 weeks and screened for WBP2 protein expression. Selected clones were pooled and maintained with same selection pressure. WBP2 expression was checked periodically.

Stable Cell Line Establishment

For WBP2 gain-of-function overexpression studies, MCF7 was transfected with pCEP4 vector, WBP2-WT, WBP2-Y192-231E and WBP2-Y192-231F/pCEP4. 24 hr post-transfection, cells were exposed to 250 ug/ml of Hygromycin (Invitrogen) for 3 weeks and screened for WBP2 protein expression. Selected clones were pooled and maintained with same selection pressure. WBP2 expression was checked periodically.

Subcellular Fractionation

The subcellular fractionation was carried out according to a protocol by Dr. Richard Pattern, Tufts-New England Medical Centre, Boston, Mass., USA. Briefly, cells on plate were rinsed once with ice-cold PBS and scraped in ice-cold hypotonic lysis buffer (20mM Hepes, pH7.4; 10 mM KCl; 2 mM MgCl2; 1 mM EDTA; 1mM EGTA; 1 mM DTT; 1X Protease Inhibitor Cocktail; 50 mM NaF; 1 mM sodium orthovanadate) and incubated on ice for 1 hr. The lysate was passed through a 25G needle 15 times. The nuclear pellet was centrifuged out at 3000 rpm for 5 min and washed twice with hypotonic lysis buffer before resuspending and lysing in nuclear lysis buffer (NID Lysis Buffer with 10% glycerol and 1% SDS). The nuclear lysate was then sonicated briefly. The supernatant was centrifuged at 8000 rpm for 5 min. The resulting supernatant was the cytosolic and membrane fraction. This supernatant was further centrifuged at 40000 rpm for 1 hr. The resulting supernatant was collected as the cytosolic fraction.

Luciferase Reporter Assay

The Dual-Luciferase TM reporter assay system (Promega) was used for sequential measurement of Firefly and Renilla luciferase activities according to manufacturer's instructions. Quantification of luciferase activities were carried out using a luminometer (Sirius).

The Dual-Luciferase TM reporter assay system (Promega) was used for sequential measurement of Firefly and Renilla luciferase activities according to manufacturer's instructions. Quantification of luciferase activities were carried out using a luminometer (Sirius, Berthold-DS Inc, Germany). Briefly, transfected cells in 24-well plate were rinsed once with ice-cold PBS and lysed in 1x Passive Lysis Buffer (PLB) for 15 min at RT. The crude lysate was first incubated with Luciferase Assay Substrate (LAR II) to measure the firefly luciferase activity, followed by incubation with Stop and Glo Substrate to measure the Renilla luciferase activity.

Cell Based Assays

Cell Proliferation Assay was performed using the CellTiter 96® Aqueous One Solution Non-Radioactive (MTS) Assay Reagent (Promega). The anchorage-independent growth was assayed using CytoSelect 96-well Cell Transformation Colorimetric Assay Kit (Cell Biolabs). Chemotaxis and cell invasion assays were performed using CytoSelect 96-well Cell Migration Assay Kit, 8 μm (Cell Biolabs). All studies using kits were done according to manufacturer's instructions. For wound healing assay, a wound was incised in the confluent cell monolayer with a p200 pipet tip. The cells were washed once to remove cell debris and to smoothen the edge of the scratch and then replaced with fresh growth medium. The cells were incubated at 37° C. and their migration into the scratch area was monitored up to 24 hrs. Using a phase contrast microscope, the images of the scratch at the same field were captured at 0, 8, 16 and 24 hrs after scratch. The relative width of the scratch was measured quantitatively using Photoshop 5.5.

```
siRNA sequences
Yes1 siRNA
(5'-UUCUCCUACAAGAAUAUUAGCAGCC-3'; SEQ ID NO: 8), v-Src siRNA
(5'-GCCUCUCAGUGUCUGACUUCGACAA-3'; SEQ ID NO: 9), Luciferase-GL2 siRNA
(5'-CGUACGCGGAAUACUUCGA-3'; SEQ ID NO: 10), WBP2 siRNA
(5'-AGCAUCCGCUGUCCGAACUCAAUGG-3'; SEQ ID NO: 2)
and WBP2 UTR-siRNA
(5'-CAGGAACUAGCAUUGUGGGACAUUA-3'; SEQ ID NO: 11)
```

Immunofluorescence.

Cells were grown on coverslips in 6-well plate. Following various treatments, cells were fixed with 4% paraformaldehyde at room temperature and permeabilized with 0.5% Triton-X-100 in PBS. After blocking with 5% BSA for 1 hour, the cells were incubated with primary antibodies overnight [anti-ER □mouse monoclonal, 1:100, anti-E-cadherin rabbit polyclonal, 1:100, anti ZO-2 rabbit polyclonal, 1:100]. This was followed by secondary antibodies conjugated to Alex Fluor 488 (Molecular Probes, Invitrogen) at 1:1000 dilution for 1 hour. The nuclei of the cells were counterstained with 4,6-diamidino-2-phenylindole (DAPI) at 1:10000 dilution for 1 min. Coverslips containing the cells were then mounted onto glass slides with the addition of Prolong anti-fade reagent (Molecular Probes, Invitrogen) and sealed with Eukitt quick hardening mounting medium (Fluka, Sigma). Analyses were made using the Carl Zeiss Axioplan 2 fluorescence microscope (Carl Zeiss Imaging, Gottingen, Germany) with a 100x oil immersion objective. The Axiovision Rel4.6 software was used to capture and analyze the images.

In Vitro Cell-Based Assays

Cell proliferation was measured using the CellTiter 96® Aqueous One Solution Non-Radioactive (MTS) Cell Proliferation Assay Reagent (Promega). Briefly, 5000 cells per well were seeded in triplicate in 100 μl culture medium in a 96-well plate on day 0 and the cell growth was monitored daily until day 4. 20 μl of the MTS reagent was added to each well and mixed by swirling the plate. The absorbance was measured after an hour on a plate reader (Tecan Group Ltd, Mannedorf, Switzerland) at 490 nm. The anchorage-independent growth was assayed using CytoSelect 96-well Cell Transformation Colorimetric Assay Kit (Cell Biolabs Inc., San Diego, Calif., USA). Briefly, 50 μl of base agar matrix was added in the bottom of each well of a 96-well plate. When the base agar was solidified, 75 μl of cell suspension/soft agar matrix containing 5000 cells was layered on top, followed by 50 μl of culture medium. After 10 days of incubation at 37° C., the agar matrix was solubilized and cells were detected using MTT solution. Absorbance was measured at 570/630 nm. For scratch assay, cells were seeded onto 6-well plate and grown until a confluent monolayer. A wound was incised in the cell monolayer with a p200 pipet tip. The cells were washed once with growth medium to remove the cell debris and to smoothen the edge of the scratch and then replaced with fresh growth medium.

The cells were incubated at 37° C. and their migration into the scratch area was monitored up to 24 hrs. Using a phase-contrast microscope, the images of the scratch at the same field were captured at 0, 8, 16 and 24 hrs after scratch. The relative width of the scratch was measured quantitatively using Photoshop 5.5. The extent of gap closure was determined as the rate of cell migration. For chemotaxis assay, 2×105 overnight serum starved cells were seeded in serum-free medium on the top chamber of 96 trans-well plate with polycarbonate membrane chambers (8 µm pore size, Cell Biolabs) and medium containing 10% fetal bovine serum (FBS) were added to the bottom chambers as the chemoattractant. After 2 hr incubation, top non-migratory cells were removed, bottom migrated cells were first dissociated from the membrane, then lysed and quantified using CyQuant GR fluorescent dye at 480 nm/520 nm. For invasion assay, 2×105 cells serum starved overnight were seeded in serum-free medium on the top chambers of 96 trans-well plate with polycarbonate membrane chambers coated with a uniform layer of basement membrane matrix (8 µm pore size, Cell Biolabs) and medium containing 10% fetal bovine serum (FBS) were added to the bottom chambers. After 24 hr incubation, top non-invasive cells were removed, bottom invaded cells were first dissociated from the membrane, then lysed and quantified using CyQuant GR fluorescent dye at 480 nm/520 nm.

Tumor Xenograft in Nude Mice

Four- to 6-week old female nude mice were inoculated s.c. in the hind flanks with 5×106 MCF7 stables of pCEP4 or WBP2-WT or WBP2-Y192-231E or WBP2-Y192-231F cells suspended in 100 □l of Matrigel (BD). Tumor development was monitored and measured every 3-4 days until day 22.

Results

Figure 1:
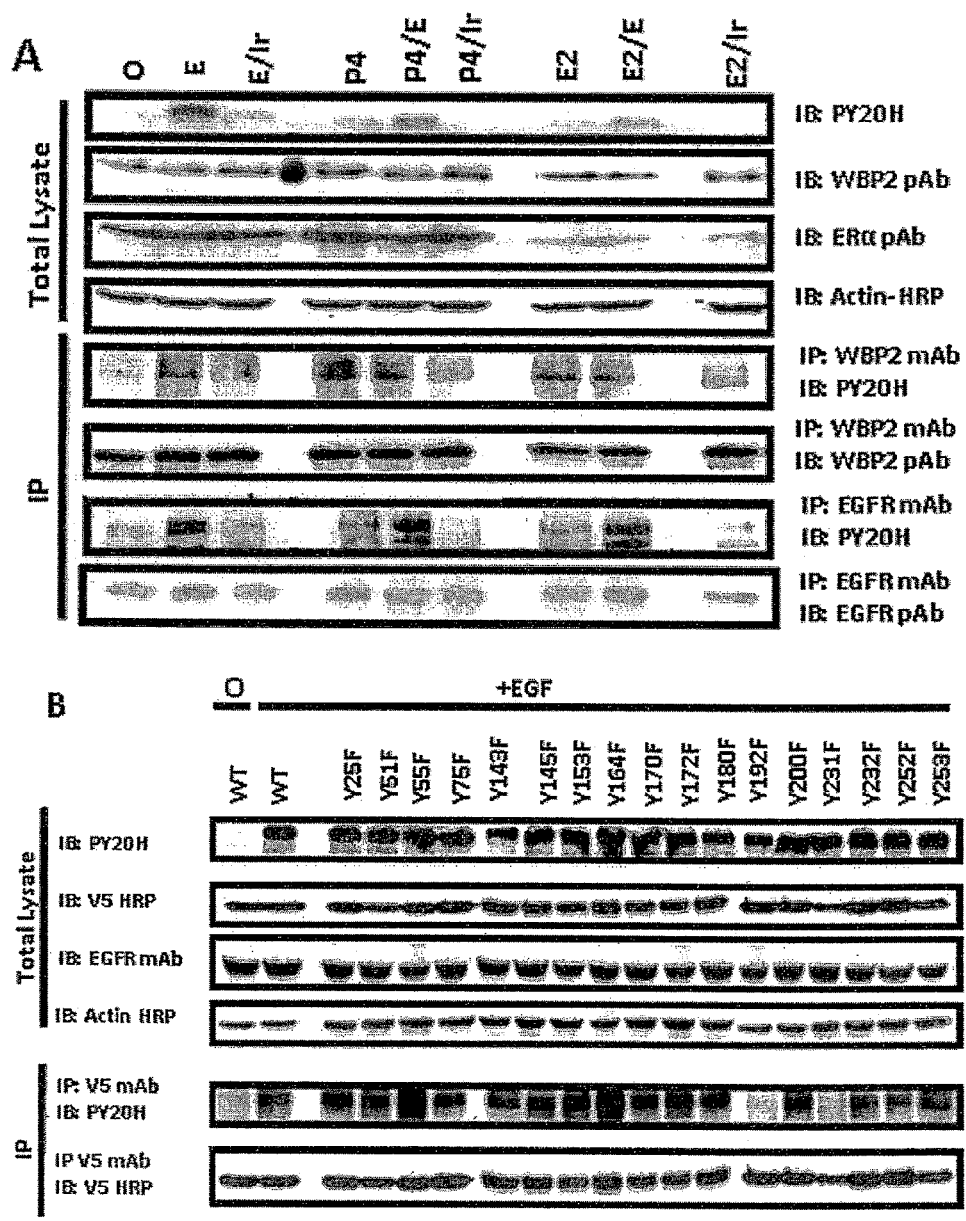
FIG. 1: Estrogen and Progesterone-induced Tyrosine Phosphorylation of WBP2 at Tyr192 and Tyr231 via EGFR Cross-Talk A: Serum-starved cells were stimulated with 50 ng/ml EGF (E) for 5 min or hormone-stripped cells were stimulated with 10 nM Estrogen (E2) or 100 nM Progesterone (P4) for 24 hr with/without 10 µM Iressa (Ir) pre-treatment for 1 hr. Whole cell lysates were used for IP/IB analysis with antibodies indicated. B: HeLa were co-transfected with EGFR and V5-tagged WT-WBP2 or individual Y→F mutants. C: HeLa were co-transfected with EGFR and V5-tagged wild type, individual single mutant (Y192F, Y231F, Y253F) or double mutant (Y192-231F) of WBP2. For experiments B and C, 24 hr post-transfection, cells were serum-starved overnight and stimulated with 50 ng/ml EGF for 5 min. Whole cell lysates were used for IP/IB analysis with antibodies indicated. D: Serum-starved MCF7 were stimulated with 50 ng/ml EGF (E) for 5 min or hormone-stripped cells were stimulated with 10 nM estrogen (E2) or 100 nM progesterone (P4) for 24 hr with/without 10 µM Iressa (Ir) pre-treatment for 1 hr. Whole cell lysates were used for IP/IB analysis with antibodies indicated. E: HeLa were co-transfected with EGFR and V5-tagged WT-WBP2 or individual Y→F mutants. F: HeLa were co-transfected with EGFR and V5-tagged WT-WBP2, individual single mutant (Y192F, Y231F, Y253F) or double mutant (Y192-231F) of WBP2. For experiments B and C, 24 hr post-transfection, cells were serum-starved overnight and stimulated with 50 ng/ml EGF for 5 min. Whole cell lysates were used for IP/IB analysis with antibodies indicated. G: MCF7 were transfected with V5-tagged WT-WBP2 or Y192-231F-WBP2 mutant. 24 hr post-transfection, serum-starved MCF7 were stimulated with 50 ng/ml EGF (E) for 5 min or hormone-stripped cells were stimulated with 10 nM Estrogen (E2) or 100 nM Progesterone (P4) for 24 hr. Whole cell lysates were used for IP/IB analysis with antibodies indicated. "O" denotes "untreated/vehicle-treated"
Figure 1:
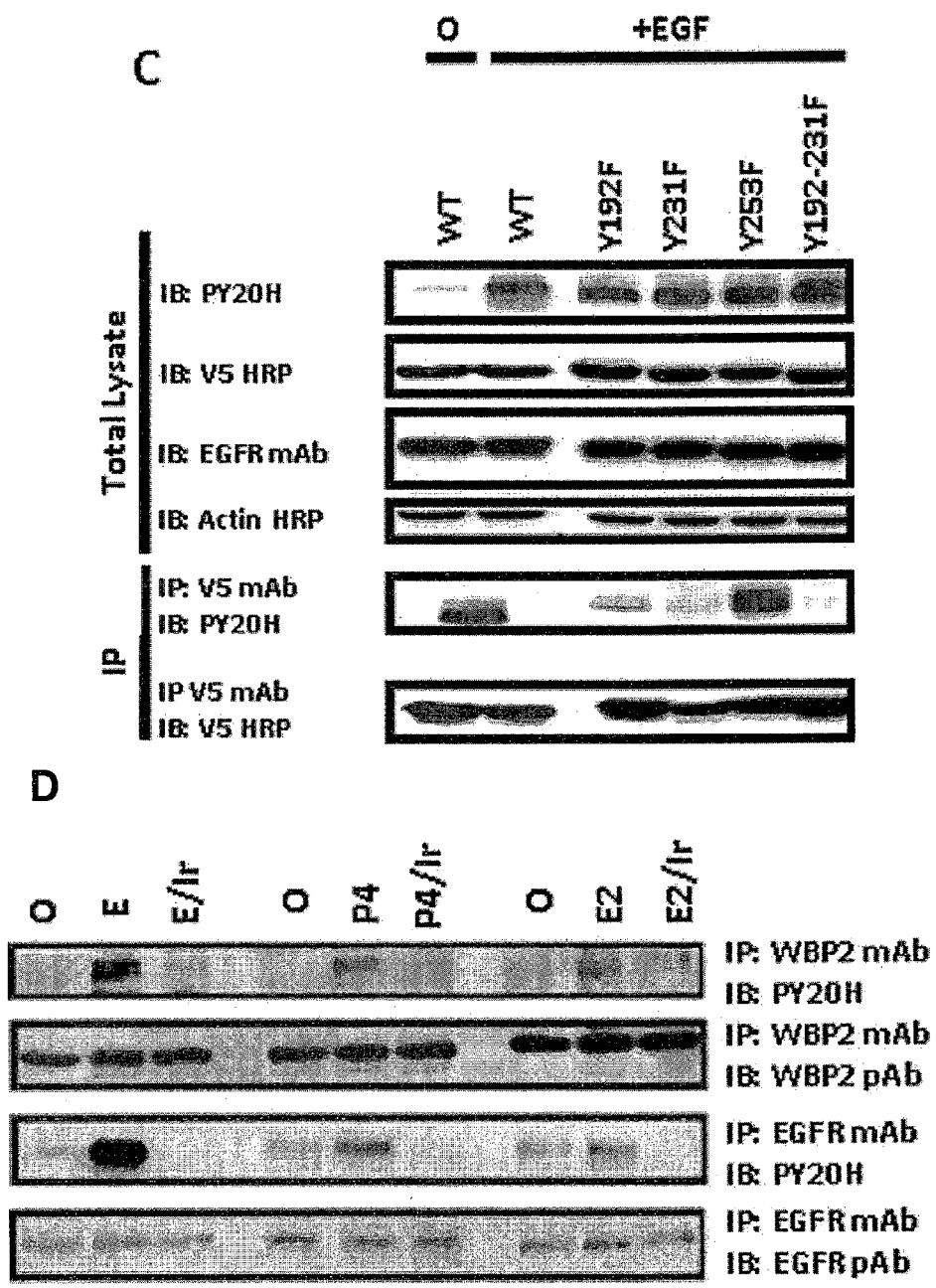
Figure 1:
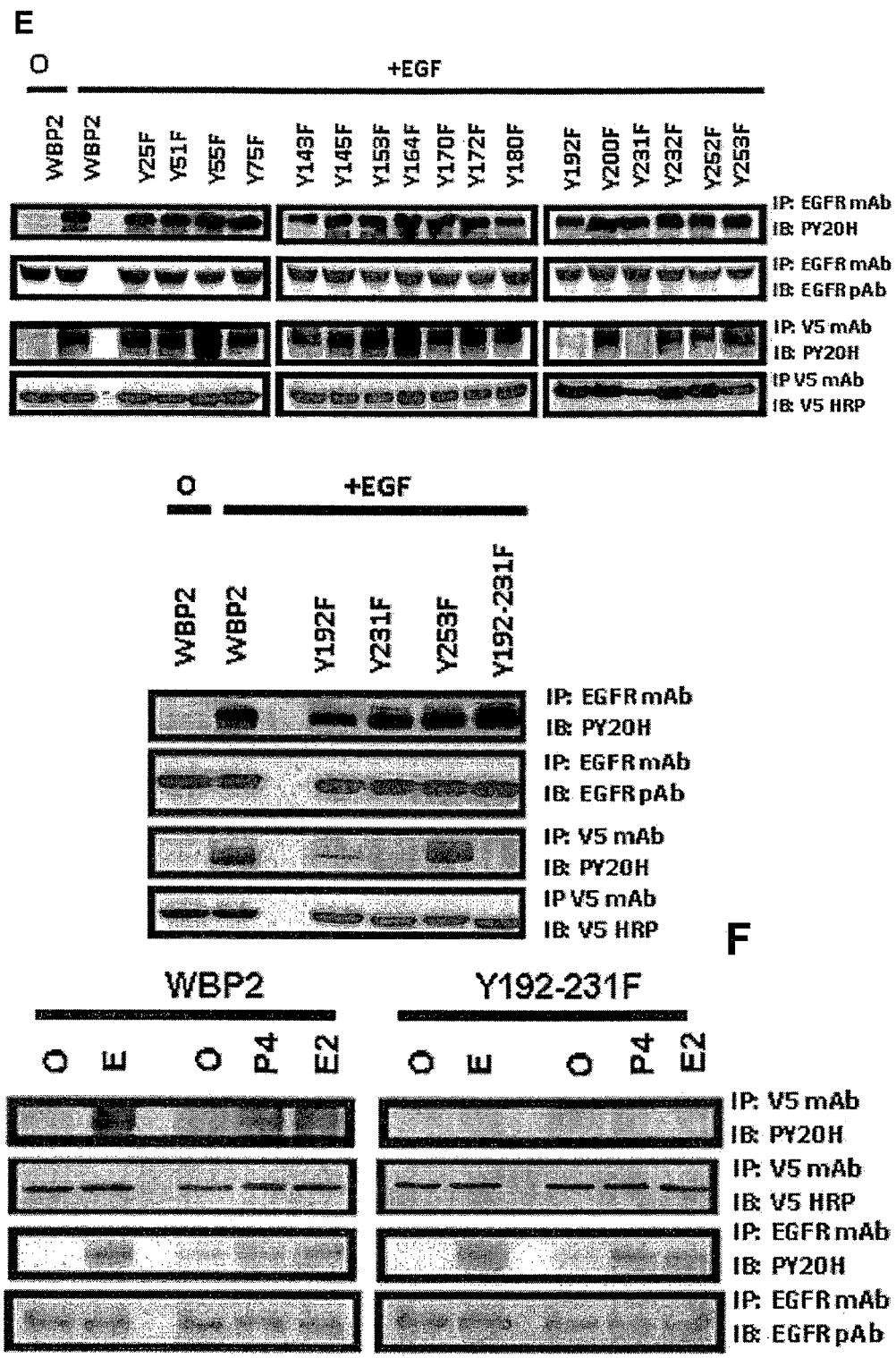

Estrogen and Progesterone Induced Tyrosine Phosphorylation of WBP2 at Tyr192 and Tyr231 Via EGFR Cross-Talk Cross-talk between estrogen/progesterone and EGFR signaling is well reported (20-22). Since WBP2 has been shown to be an EGFR target, we investigated whether estrogen/progesterone could induce WBP2 tyrosine phosphorylation through this crosstalk. As shown in FIG. 1A, WBP2 was tyrosine phosphorylated upon estrogen/progesterone stimulation in MCF7, albeit weaker compared to EGF stimulation. Significant abolishment of estrogen/progesterone-induced WBP2 phosphorylation by Iressa indicated that crosstalk with EGFR played a role in estrogen/progesterone-mediated WBP2 phosphorylation.

Next, we sought to map the EGF-dependent tyrosine phosphorylation site(s) on WBP2. 17 potential tyrosine phosphorylation sites predicted by various software (Netphos2.0 HPRD Phosphomotif Finder and NetphosK were individually mutated to phenylalanine. WT-WBP2 or Y→F mutant was cotransfected with EGFR into HeLa cells, which were then treated with EGF. All Y→F mutants, except Y192F and Y231F, were tyrosine phosphorylated to the same extent as WT WBP2 upon EGF stimulation (FIG. 1B). Near complete abolishment of WBP2 tyrosine phosphorylation was observed when both Y192 and Y231 were mutated (FIG. 1C).

We investigated whether E2/P4 could induce endogenous WBP2 tyrosine phosphorylation through this crosstalk. Cells were treated with E2 or P4 for 24 h since this was the time point used by the group which reported on the role of WBP2 as a coactivator for E2 and P4 receptors (11). Another reason was the fact that E2/P4 cross talk with EGF signaling has been attributed in part to upregulation of EGFR ligands and subsequent autocrine activation of EGFR (23). As shown in FIG. 1D, WBP2 was tyrosine phosphorylated upon E2 or P4 stimulation in MCF7, albeit weaker compared to EGF(E) stimulation. Significant abolishment of E2/P4-induced WBP2 phosphorylation by Iressa indicated that WBP2 or Y→F mutant was co-transfected with EGFR into HeLa cells, which were then treated with EGF. All Y→F mutants, except Y192F and Y231F, were tyrosine phosphorylated to the same extent as WT WBP2 upon EGF stimulation (FIG. 1E). Near complete abolishment of WBP2 tyrosine phosphorylation was observed when both Y192 and Y231 were mutated (FIG. 1F). To ascertain if the same two sites were tyrosine phosphorylated in response to estrogen/progesterone stimulation, MCF7 transfected with WBP2 or Y192/231F double mutant was treated with estrogen/progesterone and their tyrosine phosphorylation status compared. Mutation of both Y192 and Y231 almost completely abolished the estrogen/progesterone-induced tyrosine phosphorylation of WBP2 (FIG. 1G).

c-Src and c-Yes Regulate WBP2 Tyrosine Phosphorylation

Figure 2:
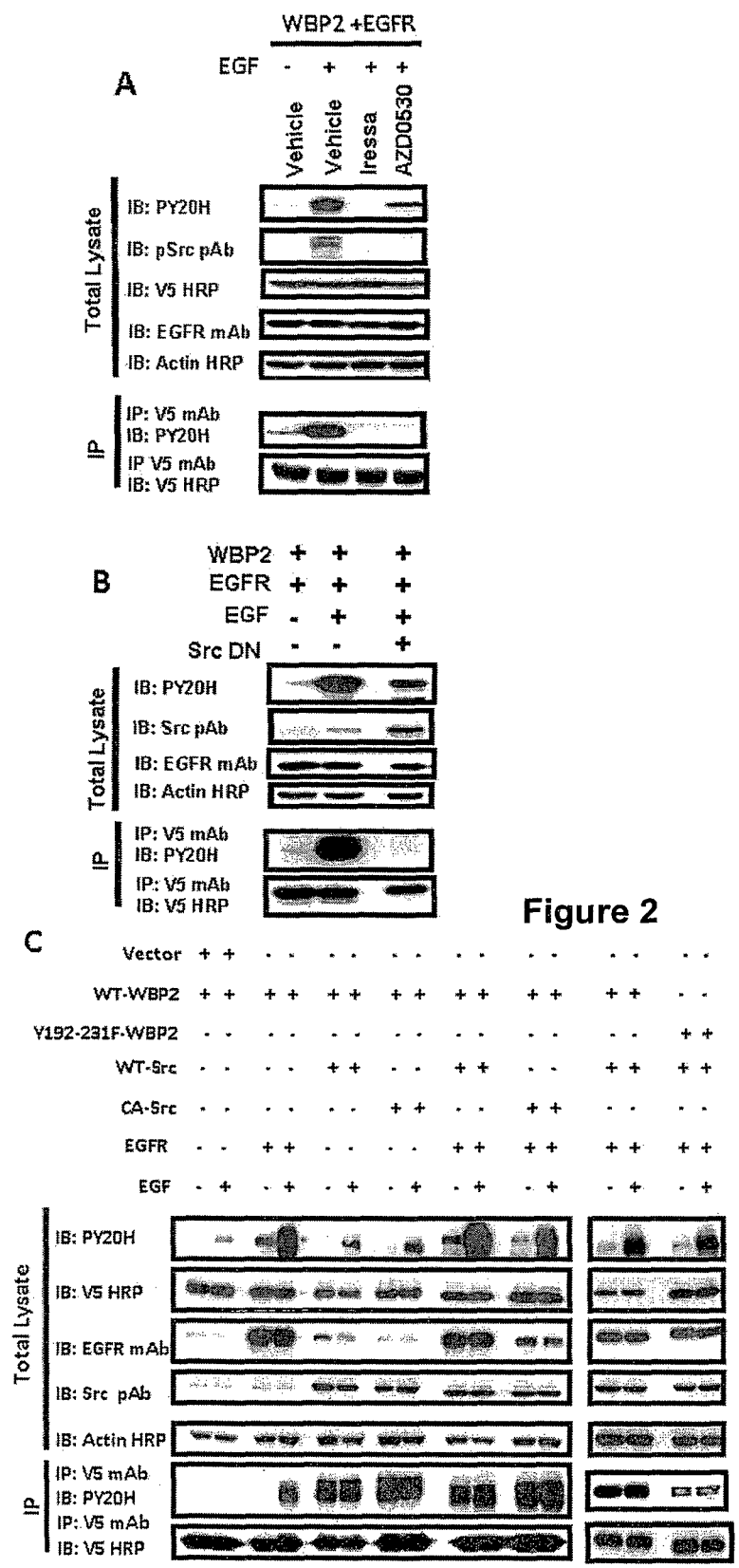
FIG. 2: Regulation of WBP2 Tyrosine Phosphorylation by c-Src
Figure 2:
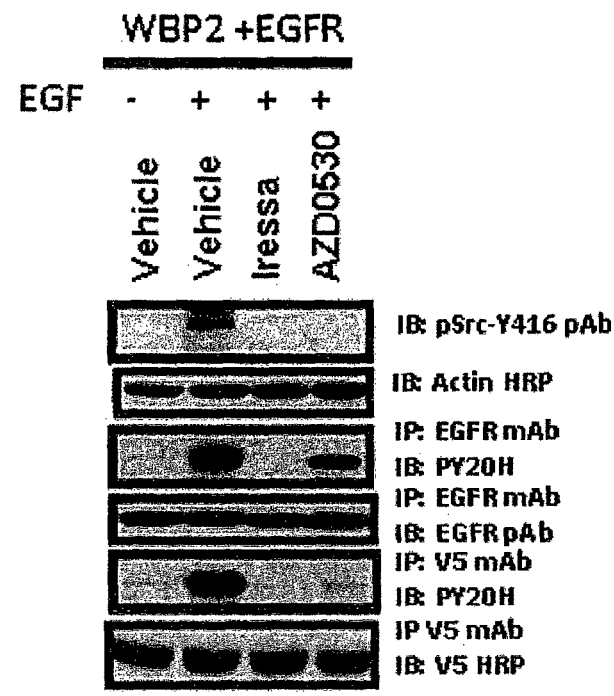
Figure 2:
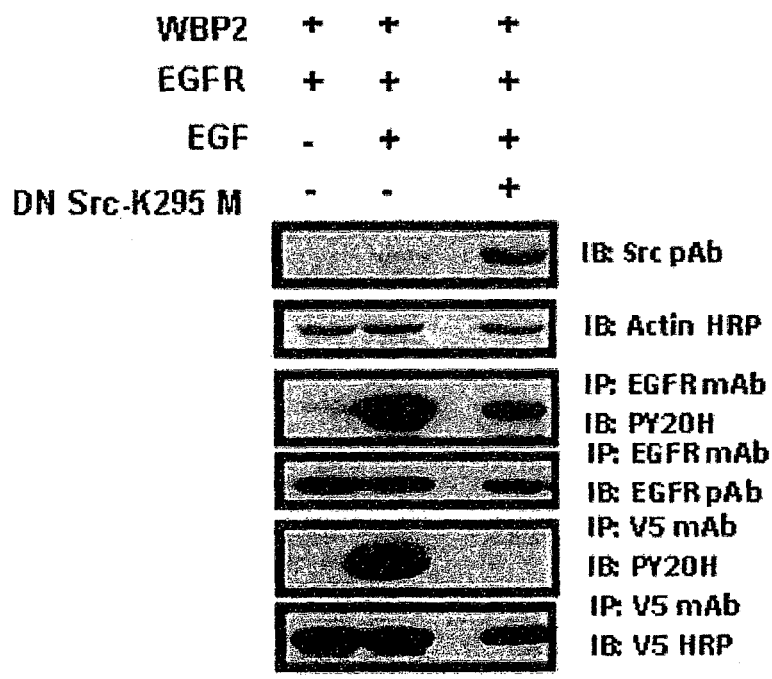
Figure 2:
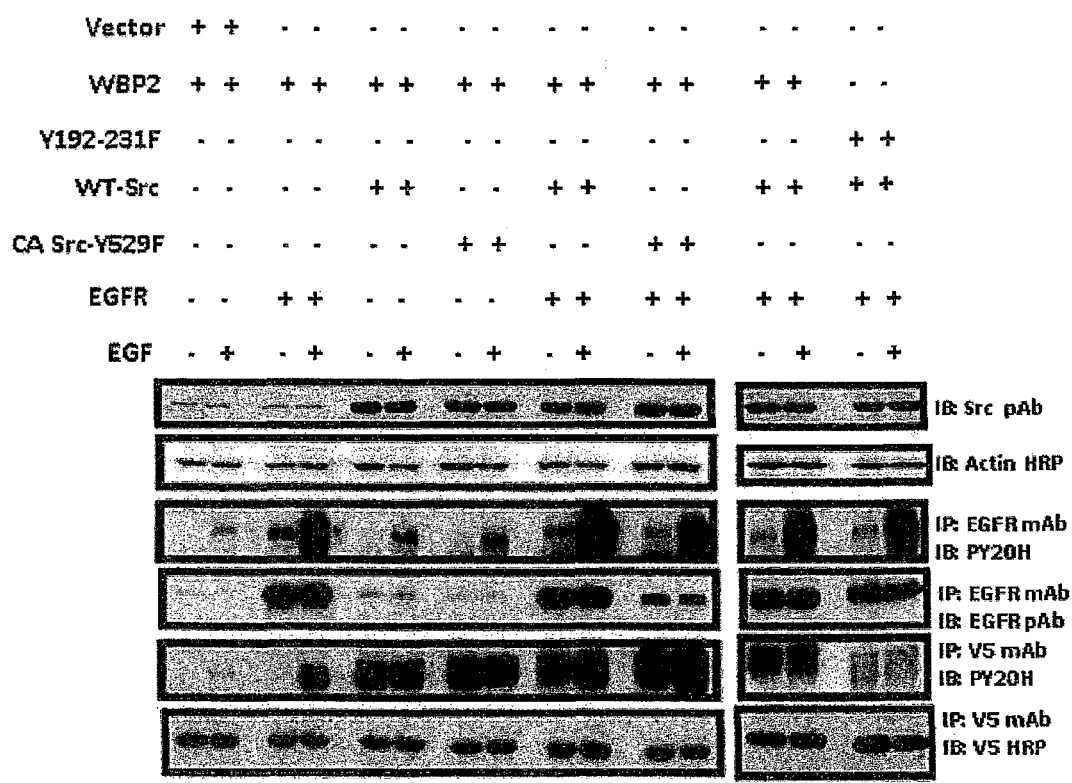
Figure 2:
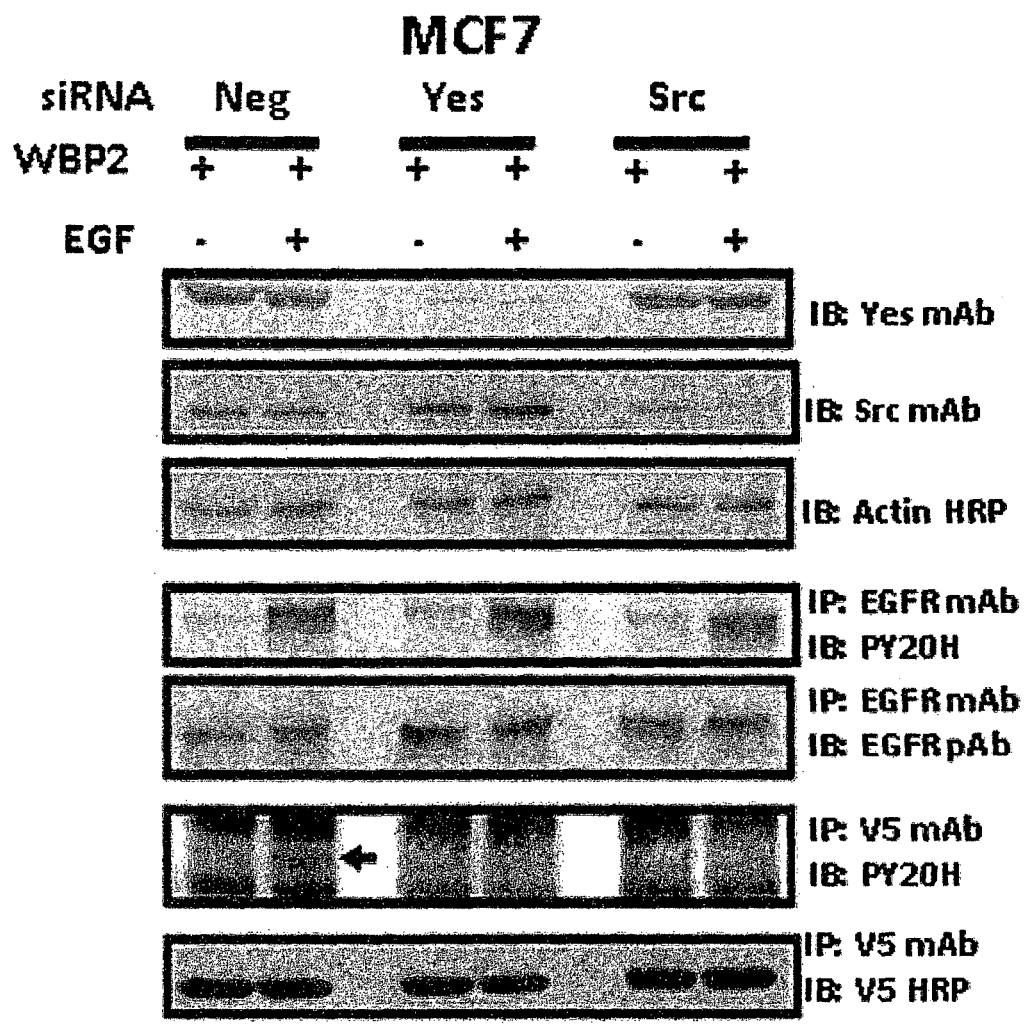

Src family kinases are key downstream kinases responsible for transducing EGFR-initiated signals. There are 9 members but only c-Src, c-Yes and Fyn are dominantly expressed in a wide variety of cell types whereas the other members are expressed primarily in hematopoietic cells (21). Disruption of c-Src activity by AZD0530 (FIG. 2A) and dominant negative c-Src (FIG. 2B) abolished EGF-induced tyrosine phosphorylation of WBP2. It is noted that c-Src inhibition also resulted in significant reduction of EGFR activation, suggesting that the negative effect of c-Src inhibition on WBP2 phosphorylation was mediated partly through its inhibitory effect on EGFR activation. This is not surprising since c-Src mediated phosphorylation of EGFR has been reported to increase EGFR activity (22). Therefore, c-Src could potentially act both upstream and downstream of EGFR during WBP2 tyrosine phosphorylation. Overexpression of wild-type (WT) or constitutively active (CA) c-Src resulted in tyrosine phosphorylation of WBP2, albeit in an EGF-independent manner (FIG. 2C). Co-expression with EGFR potentiated the WBP2 phosphorylation slightly. Additionally, c-Src-induced WBP2 phosphorylation was mediated largely through Tyr192 and Tyr231.

Next, the role of c-Yes in EGF-induced WBP2 phosphorylation was investigated since c-Yes interacts with YAP (23), which interacts with WBP2 (24, 25). Unlike c-Src, WT and CA c-Yes mediated WBP2 tyrosine phosphorylation was inducible by EGF, although the basal and EGF-induced WBP2 tyrosine phosphorylation was higher for CA compared to WT c-Yes (FIG. 3A). It is noted that c-Yes-mediated WBP2 phosphorylation was less remarkable as compared to that mediated by EGFR. Synergistic potentiation of WBP2 phosphorylation by coexpression of c-Yes with EGFR was also EGF inducible. Hence, the role of c-Yes in WBP2 phosphorylation was dependent on the availability of both EGFR and c-Yes. Similar to c-Src, c-Yes regulated phosphorylation of WBP2 at Tyr192 and Tyr231.

The roles of c-Yes and c-Src in WBP2 phosphorylation were further addressed by siRNA studies. EGF induced WBP2 tyrosine phosphorylation was almost completely abolished by c-Yes knockdown and to a lesser extent by c-Src knockdown (FIG. 3B). The partial reduction of EGF-induced WBP2 phosphorylation by c-Src could be due to the less efficient knockdown of c-Src or the functional redundancy from c-Yes. Collectively, c-Yes is more likely to act immediately upstream of WBP2 compared to c-Src, which may act indirectly via EGFR.

In addition, c-Yes had been reported to interact with YAP (26), which in turn had been demonstrated to interact with WBP2 (27, 28). We therefore ask whether c-Src and c-Yes play a role in EGF-induced WBP2 tyrosine phosphorylation. Disruption of c-Src activity by AZD0530, a highly selective, dual-specific Src/Abl kinase inhibitor (FIG. 2D) and dominant negative c-Src-K295M (FIG. 2E) abolished EGF-induced tyrosine phosphorylation of WBP2 in HeLa cells. It is noted from FIGS. 2D and 2E that c-Src inhibition also resulted in reduction of EGFR activation (EGFR autophosphorylation). Hence, it is possible that the negative effect of c-Src inhibition on WBP2 phosphorylation might be mediated partly through its inhibitory effect on EGFR activation. This is not surprising since c-Src mediated phosphorylation of EGFR had been reported to increase EGFR activity (29). Therefore, c-Src could potentially act both upstream and downstream of EGFR during WBP2 tyrosine phosphorylation. Overexpression of wild-type (WT) or constitutively active (CA) c-Src-Y529F resulted in tyrosine phosphorylation of WBP2, albeit in an EGF independent manner (FIG. 2F, left panel). c-Src-induced WBP2 phosphorylation was mediated largely through Tyr192 and Tyr231 (FIG. 2F, right panel). Unlike c-Src, WT and CA-Y357F-c-Yes-mediated WBP2 tyrosine phosphorylation was EGF-dependent, although the basal and EGF-induced WBP2 tyrosine phosphorylation was higher for CA compared to WT c-Yes (FIG. 3). It is noted that c-Yesmediated WBP2 phosphorylation was less remarkable as compared to that mediated by EGFR. Synergistic potentiation of WBP2 phosphorylation by coexpression of c-Yes with EGFR was also EGF inducible. Hence, the role of c-Yes in WBP2 phosphorylation was dependent on EGFR activation. As in the case of c-Src, c-Yes regulated phosphorylation of WBP2 at Tyr192 and Tyr231.

The roles of c-Yes and c-Src in WBP2 phosphorylation were further addressed by siRNA studies. EGF-induced WBP2 tyrosine phosphorylation was almost completely abolished by c-Yes or c-Src siRNA knockdown in HeLa (FIG. 3E) and MCF7 cells (FIG. 2G). The EGF-induced tyrosine phosphorylation signal of WBP2 in control siRNA transfected cells was not as strong as previous experiments because EGFR was not co-transfected with WBP2. Collectively, both c-Yes and c-Src play a role in EGF-induced tyrosine phosphorylation of WBP2 but based on their differential dependence on EGFR activation, c-Yes is more likely to act downstream of EGFR while c-Src may act indirectly via EGFR.

Tyrosine Phosphorylation of WBP2 Potentiates its Coactivation Function in ERα Activity Via Regulation of its Nuclear Entry and Interaction with ERα

A pertinent question is whether tyrosine phosphorylation of WBP2 modulates its coactivator function in ERα/PR transactivation. As shown in FIG. 4A, cells expressing WT- and Y192-231F-WBP2 displayed higher basal ERα reporter activity compared to vector control that could be enhanced following estrogen but not EGF treatment. Combination of EGF and estrogen further potentiated the ERα reporter activity. Compared to WT, Y192-231F mutant displayed ~50% loss of coactivator activity upon estrogen or estrogen/EGF stimulation. To eliminate the possible interference from endogenous WT, endogenous WBP2 expression was silenced using siRNA against 5' UTR sequences and ERα reporter assays repeated in Y192-231F expressing cells. No further decrease in ERα transactivation was observed (data not shown). This indicates that Y192-231F mutation does not exert a dominant negative effect and tyrosine phosphorylation of WBP2 is not absolutely required for its coactivation of ERα activity. The difference in the potential between WT and Y192-231F in ERα transactivation was subsequently confirmed by differential expression of an estrogen-responsive target gene, cyclin D1.

We also studied the effect of Y192-231F mutation on PR reporter activity in T47D. As shown in FIG. 4A, Y192-231 mutation significantly (~30%) but not completely impaired the coactivator function of WBP2 during progesterone or progesterone/EGF stimulation. No significant PR transactivation could be detected upon EGF stimulation alone. In all cases, estrogen/progesterone/EGF-induced coactivator activities of WT-WBP2 were abolished by Iressa, pointing to the role of EGFR-mediated tyrosine phosphorylation in modulating WBP2's coactivation function. While phosphorylation of Y192 and Y231 were important, they are not absolutely required for steroid hormone-dependent transcriptional control.

Owing to its transcription regulatory role, WBP2 should localize to the nucleus at some point in time to carry out its function. As shown in FIG. 4B, WBP2 was localized predominantly in cytoplasm at basal state while nuclear WBP2 could be observed upon estrogen stimulation. The latter was reduced when Iressa was applied. FIG. 4B further showed that only the nuclear localized WBP2 was tyrosinephosphorylated. Similar observations were made when T47D and MDA-MB-231 were stimulated with EGF. These pointed to a close association of WBP2 tyrosine phosphorylation and its nuclear translocation. Indeed, impaired tyrosine phosphorylation in Y192-231FWBP2 reduced its E2-dependent nuclear entry (FIG. 4C). This may account, at least in part, for the decrease in its potentiation of ERα/PR activities. While EGF-induced tyrosine phosphorylation also facilitated nuclear entry of WBP2, it was not sufficient to potentiate the ERα transactivation. Thus, the function of WBP2 in ER transactivation additionally requires other factors presented by estrogen treatment. Since WBP2 interacts with ERα in the estrogen-dependent manner, we studied the effect of WBP2 tyrosine phosphorylation on its interaction with ERα. As shown in FIG. 4D, Y192-231F mutation impaired estrogen-induced interaction between WBP2 and ERα.

As phosphorylation is well known to regulate the activity of transcriptional coactivators, we examined whether tyrosine phosphorylation of WBP2 modulates its reported coactivator function in ERα/PR transactivation. As shown in FIG. 4E upper panel, MCF7 cells stably expressing WBP2 and Y192-231F mutant displayed higher basal ERα reporter activity compared to vector control that could be enhanced following estrogen but not EGF treatment (FIG. 4I), suggesting that ERα transcriptional complex formation is induced predominantly by estrogen. The number of fold activation of ER reporter enhanced by the presence of WBP2 here (10 fold) is similar to that previously reported (12 fold) (11). Relative to vector and compared to WBP2, Y192-231F mutant displayed ~60% loss of coactivator activity upon estrogen stimulation. To eliminate the possible interference from endogenous WBP2, endogenous WBP2 expression was silenced using siRNA against 5' UTR sequences and ERα reporter assays repeated in Y192-231F expressing cells. No further decrease in ERα transactivation was observed (data not shown).

This indicates that Y192-231F mutation did not exert a dominant negative effect and tyrosine phosphorylation of WBP2 is not absolutely required for its coactivation of ERα activity. The difference in the potential between WT and Y192-231F in ERα transactivation was subsequently confirmed by differential expression of an estrogen-responsive target gene, cyclin D1 (FIG. 4J).

We also studied the effect of Y192-231F mutation on PR reporter activity in T47D, which is more responsive to progesterone stimulation than MCF7. As shown in FIG. 4E lower panel, Y192-231F mutation significantly (~50%, relative to vector and compared to WBP2) impaired the PR coactivator function of WBP2 during progesterone stimulation. In all cases, estrogen/progesterone-induced coactivator activities of WBP2 could be abolished by Iressa pointing to the role of EGFR-mediated tyrosine phosphorylation in regulating the ER □/PR-coactivating function of WBP2. While phosphorylation of Y192 and Y231 were important, they are not absolutely required for steroid hormone-dependent transcriptional control.

Owing to its transcription regulatory role, WBP2 should localize to the nucleus at some point in time to carry out its function. As shown in FIG. 4F, WBP2 was localized predominantly to the cytoplasm at basal state while increased nuclear WBP2 could be observed upon estrogen stimulation of T47D cells. Next, we wanted to know whether nuclear localization of WBP2 might be regulated by WBP2 phosphorylation. To this end, we took the cytosolic and nuclear fractions, conducted immunoprecipitation of WBP2 and examined its tyrosine phosphorylation status. As shown in FIG. 4F, only the nuclear-localized WBP2 was tyrosine-phosphorylated. Similar observations were made when T47D and MDA-MB-231 were stimulated with EGF (FIGS. 4K and L). These pointed to a close association of WBP2 tyrosine phosphorylation and its nuclear translocation. Indeed, impaired tyrosine phosphorylation in Y192-231F-WBP2 reduced its E2-dependent nuclear entry (FIG. 4G). This may account, at least in part, for the decrease in its potentiation of ER□/PR activities. While EGF induced tyrosine phosphorylation also facilitated nuclear entry of WBP2 (FIG. 4M), it was not sufficient to potentiate the ERα transactivation (FIG. 4J). This implies that the function of WBP2 in ER□transactivation additionally requires other factors presented by only estrogen but not EGF treatment.

Since WBP2 interacts with ER □in an estrogen-dependent manner, we studied the effect of WBP2 tyrosine phosphorylation on its interaction with ERα. To this end, WBP2 or Y192/231F phosphodefective mutant transfected MCF7 cells were untreated or treated with E2 and the lysates harvested. We consistently observed a diminished level of ERα in E2-stimulated cells. While the reason is not clear, it could be attributed to i) E2-induced high affinity binding of ERα insoluble chromatin complex that cannot be solubilized by the lysis buffer used and/or ii) E2-induced degradation of ERα (30). The lysates were then immunoprecipitated with anti-ERα antibodies or control antibodies and the immunoprecipitates probed with anti-V5 to detect for exogenous WBP2 or its mutant. As shown in FIG. 4H, Y192-231F mutation impaired estrogen-induced interaction between WBP2 and ER□. Despite decreased level of ERα in E2-treated cells, similar amounts of ERα in both untreated and treated cells were enriched. This could be due to the limiting amounts of primary and/or secondary antibodies (conjugated to agarose beads) used during immunoprecipitation.

Roles and Impact of WBP2 Phosphorylation in E2-Mediated Breast Cancer Biology

To investigate the function of WBP2 in breast cancer biology, MCF7 cells stably expressing the vector, WT, Y192-231E mutant and Y192-231F mutant of WBP2 were generated. Pooled clones were used to avoid clonal variations. Expression of WBP2 and its mutants was monitored (data not shown).

Overexpression of WBP2-WT and more drastically WBP2-Y192-231E mutant promoted the hormoneindependent cell proliferation of MCF7 when compared to the vector control (FIG. 5A). Estrogen further enhanced the growth of WBP2-WT-overexpressing MCF7, implicating WBP2 in the estrogen responsiveness of breast cancer cells. The increase in baseline and estrogen-induced growth were considerable but not completely abolished in cells expressing WBP2-Y192-231F. Consistent with the cell proliferation results, overexpression of WBP2-WT or WBP2-Y192-123E but not WBP2-Y192-231F promoted both basal and estrogen-induced anchorage-independent growth of MCF7 in soft agar assays.

In the wound healing assay, the motility of WBP2-Y192-231E mutant-expressing cells was dramatically enhanced even in the absence of estrogen (FIG. 5B). Compared to Y192-231-E mutant, WT-WBP2 expressing cells had much lesser motility whereas Y192-231F mutant-expressing cells displayed the least motility. In the chemotaxis assays, Y192-231E-expressing cells displayed the highest migratory potential. WT- and Y192-231F-expressing cells also showed increased cell motility relative to vector control but did not differ much from each other. The effect of estrogen was not analyzed due to the short assay duration. On the other hand, WT-WBP2 overexpression increased estrogen-induced invasion of MCF7 while WBP2-Y192-231E mutant drastically enhanced its basal invasive properties independently on estrogen. WBP2-mediated cell invasion were significantly abolished when Y192/Y231 phosphorylation was blocked.

WBP2's ability in regulating the migratory and invasive properties of cells prompted us to examine its role in epithelial-mesenchymal transition (EMT). Strikingly, overexpression of Y192-231E mutant induced MCF7 cells to change from an epithelial to a fibroblast-like appearance (FIG. 5C). In contrast, WBP2-Y192-231F-expressing MCF7 appeared as compact clusters of cells like those of control cells. WBP2-WTexpressing MCF7 retained the epithelial clustering characteristics but were less densely packed. Moreover, confocal immunofluorescence study carried out as previously described (26) showed that WT and Y192-231E, but not Y192-231F-expressing MCF7 displayed loss/decrease of E-cadherin and ZO-2 tight junction protein expression at the cell-cell junctions.

To investigate the effect of WBP2 expression and phosphorylation in ER-positive breast cancer biology, we generated stable transfectants of MCF7 cells expressing the vector, WBP2, Y192-231E phospho-mimic and Y192-231F phospho-defective mutants of WBP2. Pooled clones were used to avoid clonal variations. Expression of WBP2 and its mutants was monitored (FIG. 5D). Note that the WBP2 Y192-231E phospho-mimic mutant displayed a mobility gel shift. This is consistent with the observed gel shift caused by tyrosine phosphorylation of WBP2 induced by pervanadate and EGF treatment in our previous study (17). Overexpression of WBP2 and more drastically the Y192-231E mutant promoted the hormone-independent cell proliferation of MCF7 when compared to the vector control (FIG. 5E). Estrogen further enhanced the proliferation of WBP2-overexpressing MCF7, implicating WBP2 in the estrogen responsiveness of breast cancer cells. The increase in baseline and estrogen-induced growth were considerably but not completely abolished in cells expressing Y192-231F. Consistent with the cell proliferation results, overexpression of WBP2 or Y192-123E but not WBP2-Y192-231F promoted both basal and estrogen-induced anchorage-independent growth of MCF7 in soft agar assay (FIG. 5F).

In the wound healing assay, the motility of Y192-231E mutant-expressing cells was dramatically enhanced even in the absence of estrogen (FIG. 5G). Compared to Y192-231-E mutant, WBP2 expressing cells had much lesser motility whereas Y192-231F mutant-expressing cells displayed the least motility. In the chemotaxis assay (FIG. 5H), Y192-231E-expressing cells displayed the highest migratory potential. WBP2 and Y192-231F-expressing cells also showed increased cell motility relative to vector control but did not differ much from each other. The effect of estrogen was not analyzed due to the short assay duration. On the other hand, WBP2 overexpression increased estrogen-induced invasion of MCF7 while Y192-231E mutant drastically enhanced its basal invasive properties independently on estrogen (FIG. 5I). WBP2-mediated cell invasion were significantly abolished when Y192/Y231 phosphorylation was blocked. In a number of the above assays, phospho-defective mutant displayed a slightly stronger phenotype compared to vector control. This implies that other functional regions of WBP2, aside from Y192 and Y231, may contribute to WBP2 function and remains to be investigated.

WBP2's ability in regulating the migratory and invasive properties of cells prompted us to examine its role in epithelial-mesenchymal transition (EMT). Overexpression of Y192-231E mutant induced MCF7 cells to be more scattered in 2D culture compared to Y192-231F-expressing and control MCF7 cells which grow as islands of cells (FIG. 5J, top panel). WBP2-expressing MCF7 retained the epithelial clustering characteristics but were less densely packed. Immunofluorescence studies carried out as previously described (31) showed that WBP2 and Y192-231E, but not Y192-231F-expressing MCF7 displayed loss/decrease of E-cadherin (FIG. 5J, middle panel) and ZO-2 (FIG. 5J, bottom panel) tight junction protein expression at the cell-cell junctions. Vimentin expression on the other hand was upregulated in WT and Y192-231E-expressing MCF7 (FIG. 6E).

To obtain a more physiological assessment of the role of WBP2 expression and phoshorylation on tumor growth, we injected Balb/c nude mice with stable transfectants of MCF7 expressing WBP2 and its mutants. The result shows that vector control MCF7 cells were weakly tumorigenic while cells expressing WBP2 and Y192-231E phospho-mimic mutant formed about 3-4 times bigger tumors than control cells ($p<0.05$). Cells expressing phospho-defective WBP2 mutant produced only marginally larger tumors than control cells (FIG. 5K).

Recently, a paper reported that WBP2 alone was not sufficient to promote anchorage independent growth of MCF10A normal mammary epithelial cells. Instead, interaction of TAZ with WBP2 was required (32). This prompted us to ask the question as to whether tyrosine phosphorylation of WBP2 could confer anchorage independent growth to MCF10A cells. To this end, we performed soft agar colony formation assay on MCF10A cells stably transfected with vector, WBP2 and Y192-231D phospho-mimic mutant (for some unknown reasons, we did not manage to obtain stable transfectant of Y 192-231E mutant in MCF10A cells). Consistent with the report by Chan et al., WBP2 did not confer anchorage independent growth to normal mammary epithelial cells. In contrast, WBP2 phospho-mimic mutant expressing MCF10A cells grew 5 fold more than vector control in soft agar (FIG. 5L). In conclusion, the ability of WBP2 phosphorylation in promoting/enhancing growth in soft agar colony assay can be demonstrated in cancer and normal mammary epithelial cells.

Figure 18:
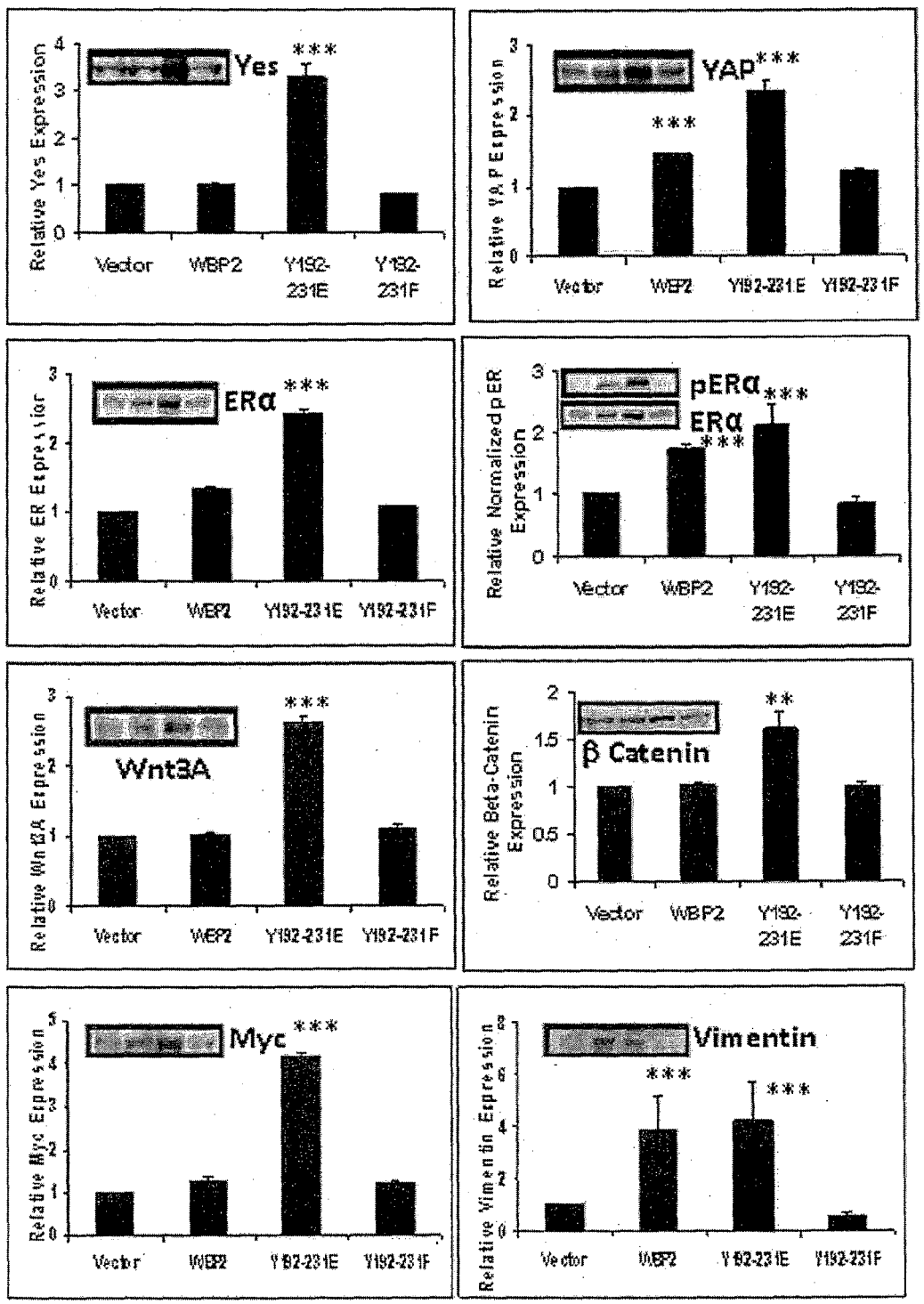
Figure 18:
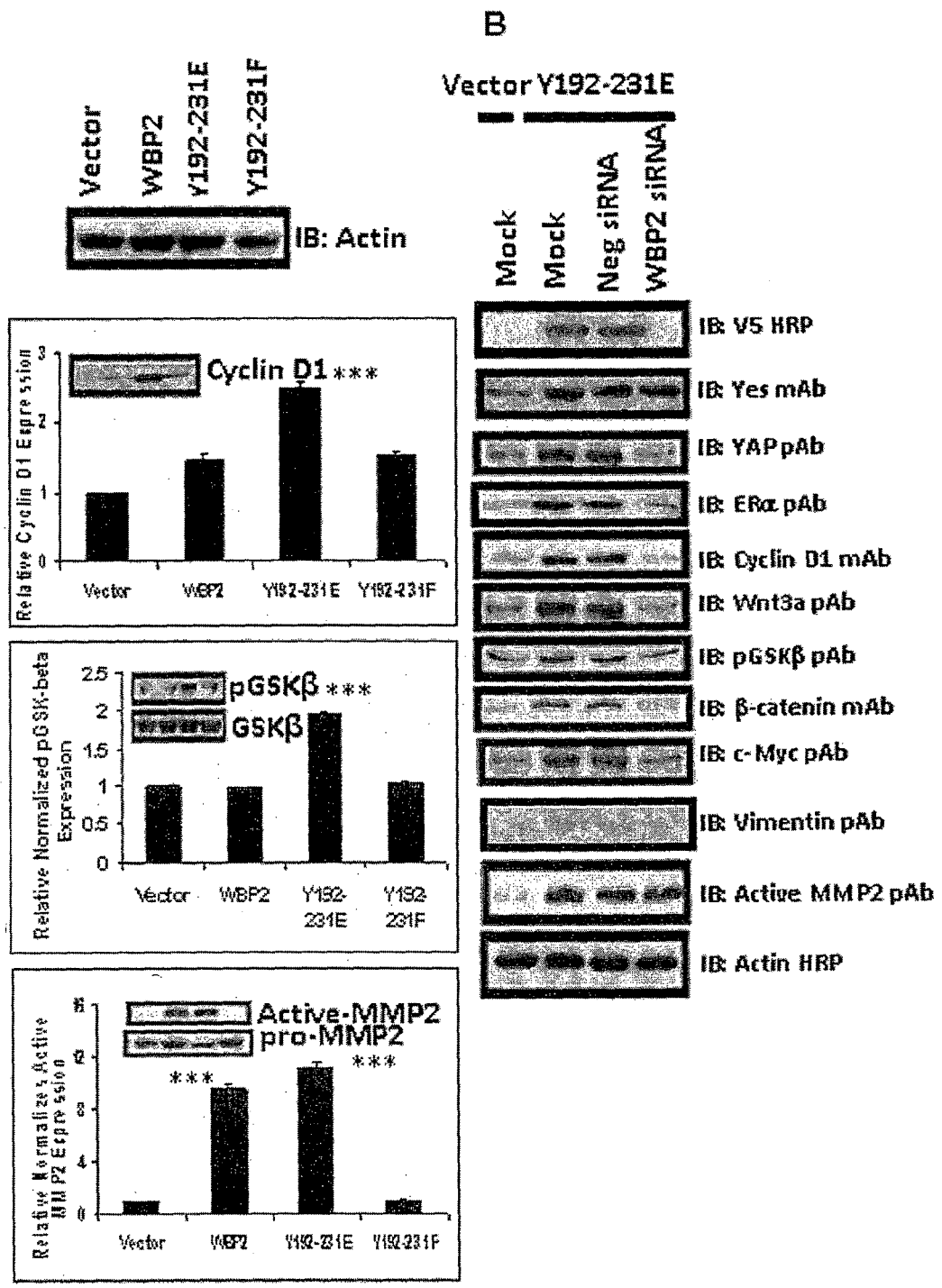
Figure 18:
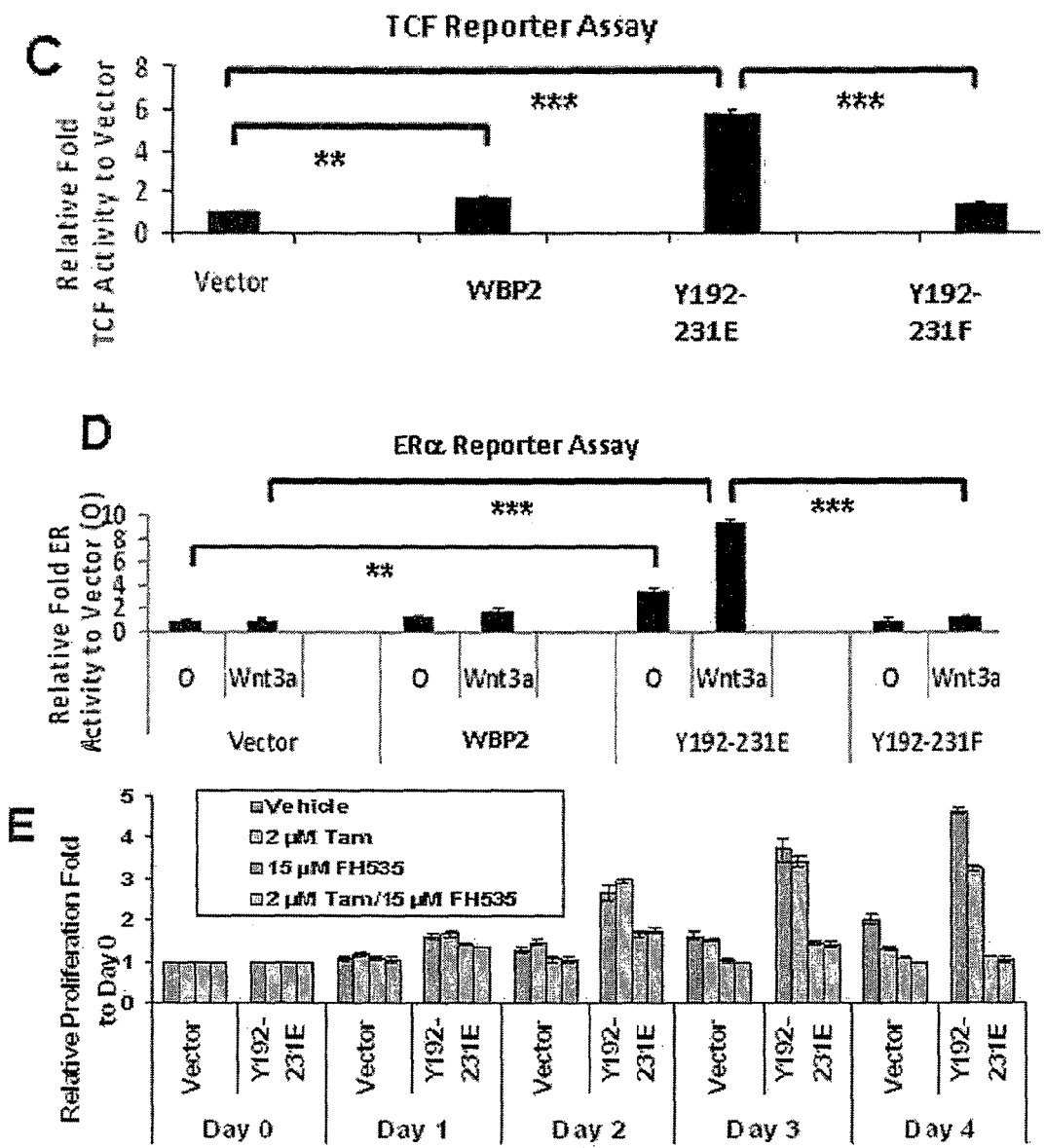
Figure 18:
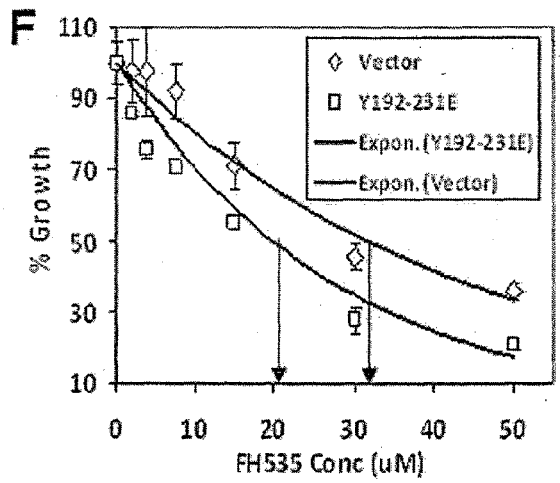
Figure 18:
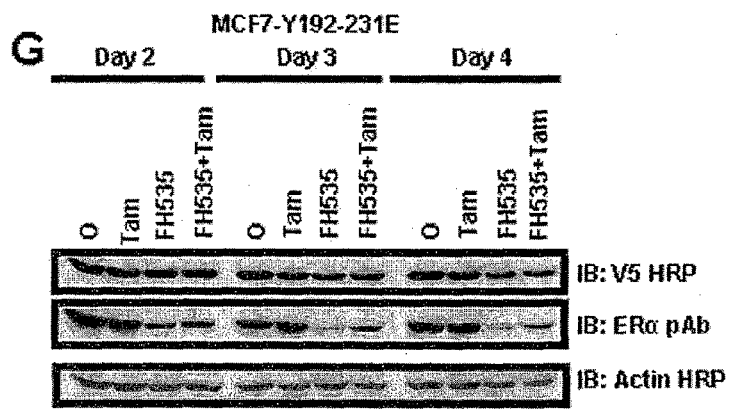
Figure 18:
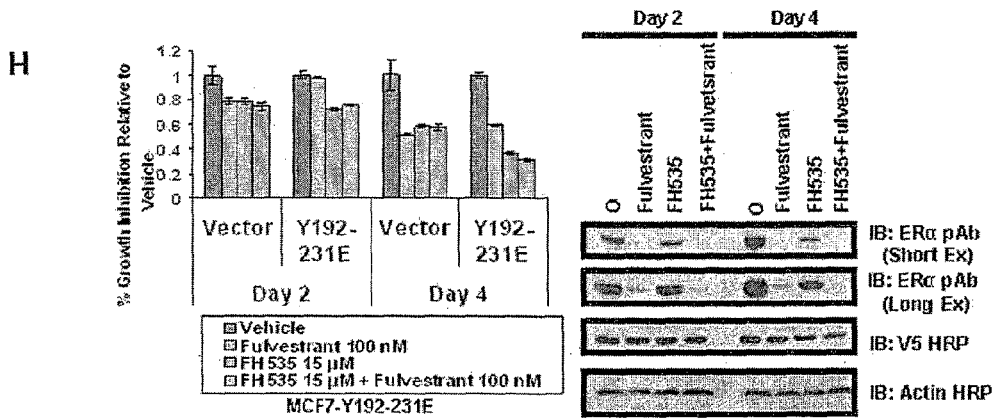
Figure 19:
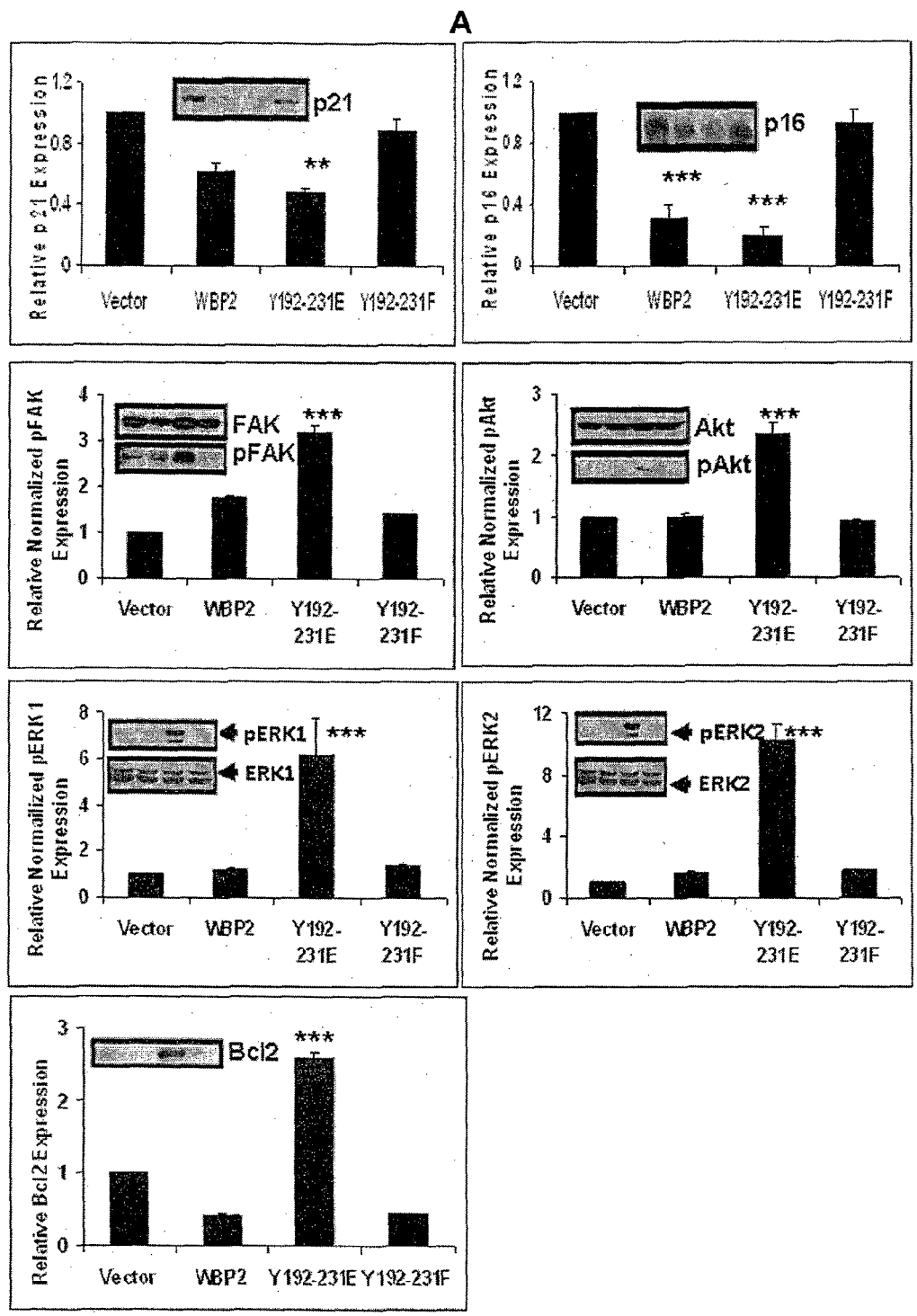
Figure 19:
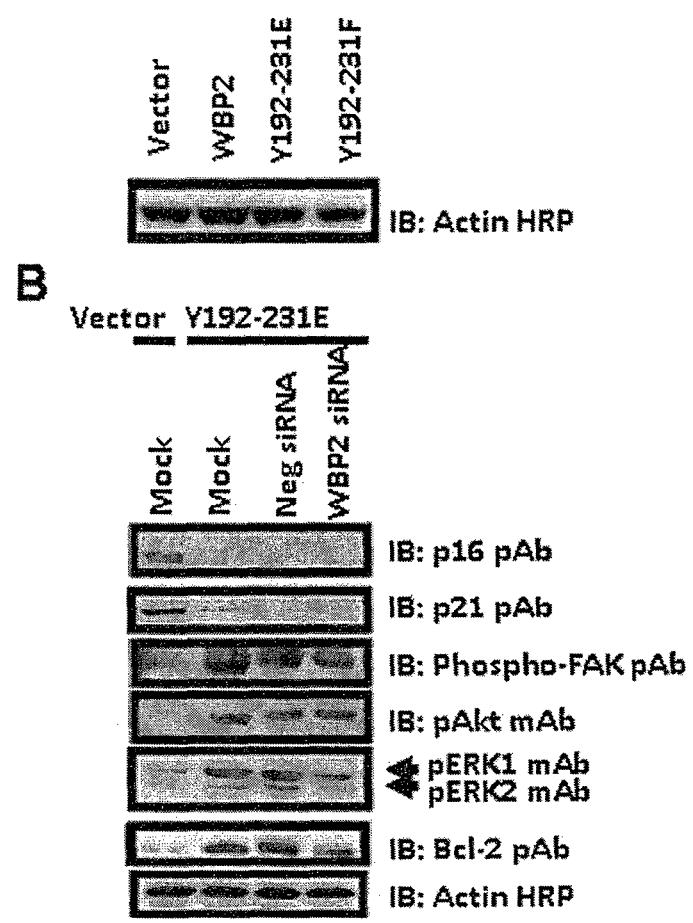

Mechanisms of WBP2-Mediated Breast Cancer Oncogenesis-Critical Role of Wnt-ERα Crosstalk WBP2 overexpression and its tyrosine phosphorylation conferred growth factor independence. We asked if these estrogen-independent phenotypes remain dependent on ERα pathway or entails other oncogenic signaling pathways. The basal expression level and in some cases, activation of c-Yes, YAP, ERα and cyclin D1 were up-regulated in the WBP2-Y192-231E—but not Y192-231F-expressing MCF7 (FIG. 18A). Consistent with the immunoblotting data, immunofluorescence data revealed stronger and more prominent nuclear ERα signal in WT and Y192-231E expressing cells compared to Y192-231F and control transfected cells. These data suggests that the ERα pathway may account for some of the WBP2-mediated effects.

Wnt signaling has been well implicated in breast cancer (27, 28). Members of the nuclear receptor (NR) superfamily, including ERα, had been demonstrated to be modulated by components of Wnt signaling pathway (29). As shown in FIG. 18A, increase in Wnt3A expression in WBP2-WT and Y192-231E expressing MCF7 was concomitant with an increase in phosphorylation-mediated inhibition of the GSK3β, stabilization of β-catenin and increased expression of Wnt pathway target genes such as c-Mycand cyclin D1. Other changes observed include i) down-regulation of the expression of cell-cycle checkpoint proteins, CDK inhibitors-p21 and p16, ii) up-regulation of Bcl-2 anti-apoptotic molecule expression and elevation of the activity of MMP2 invasion promoting protein in WT and Y192-231E expressing cells compared to Y192-231F and control transfected cells. Interestingly, the expressions of YAP, ERα, cyclin D1, Wnt3a, pGSKβ, β-catenin, c-Myc and to a lesser extent for Bcl-2 were suppressed when WBP2 expression was silenced in WBP2 Y192-231E stable transfectant using WBP2 siRNA (FIG. 18A). The expression of c-Yes, p16, p21 and active MMP2 remained unchanged. Therefore, a combination of genomic changes and active regulation of various signaling pathways contributed to the phenotypes observed in WT- and Y192-231E-expressing MCF7.

Up-regulation of Wnt signaling components by WBP2 is interesting. As a follow up, we analyzed the activity of TCF reporter in various MCF7 stable transfectants. Y192-231E-expressing MCF7 exhibited much higher basal TCF activity when compared to the vector and WT/Y192-231F-expressing counterparts implying that phosphorylated WBP2 plays a role in Wnt-TCF transcriptional regulation (FIG. 18B). Wnt activation, together with TCF1 has been shown to promote ERα transactivation (30). We further showed that Wnt-induced TCF reporter activity was greatly enhanced in Y192-231E expressing cells (FIG. 18B).

Next, we examined the relative contributions of ERα and Wnt pathway to WBP2-mediated cellular proliferation. No significant growth inhibition could be observed when Y192-231E-expressing MCF7 were treated with Tamoxifen (FIG. 18C). Even at higher doses of up to 2000 nM, retardation of proliferation by Tamoxifen of Y192-231E-expressing cells remains unremarkable. FH535 is a recently identified small-molecule inhibitor of TCF/β-catenin signaling (31). Our preliminary study shows that FH535 inhibits the recruitment of β-catenin and TCF activity was reduced by 50% 24-hr post-treatment with 15 μM FH535 in Y192-231E-expressing MCF7 (data not shown). In contrast to Tamoxifen, FH535 treatment alone significantly reduced the growth rate of Y192-231E15 expressing MCF7 to that close to the vector-expressing MCF7 at day 3. No synergistic effect could be observed when Tamoxifen and FH535 were administered in combination. Inhibition of Wnt pathway is more effective than inhibition of ERα in abrogating WBP2-mediated cell proliferation.

We also compared the sensitivity of vector- and Y192-231E stable transfectants to FH535. While dose dependent growth inhibition was observed for FH5353 in both transfectants, Y192-231E-expressing MCF7 were more sensitive to FH535-mediated growth inhibition than vector-expressing MCF7 (FIG. 18C). It hints that Wnt inhibition may specifically select against breast cancers with high expression of tyrosine-phosphorylated WBP2.

Given the central role of ERα in ER-positive breast cancer and the knowledge that Wnt pathway regulates ERα activity, we asked whether FH535-mediated growth inhibition of Y192-231E-expressing MCF7 could involve the disruption of ERα expression or activation in a fashion that is different from Tamoxifen. As shown in FIG. 18D, FH535 treatment alone but not Tamoxifen significantly reduced ERα expression without affecting the WBP2 expression, implying that phosphorylation of WBP2 could upregulate ERα expression via Wnt pathway activation.

Given the central role of ERα in ER-positive breast cancer and the knowledge that Wnt pathway regulates ERα activity, we asked whether FH535-mediated growth inhibition of Y192-231E-expressing MCF7 could involve the disruption of ERα expression or activation in a fashion that is different from tamoxifen. Interestingly, FH535 treatment alone but not tamoxifen significantly reduced ERα, expression (much like the Selective Estrogen Receptor Down-Regulator, fulvestrant) without affecting the WBP2 expression (FIG. 18G). This suggests that phosphorylation of WBP2 could up-regulate ERα expression via Wnt pathway activation. Since FH535 appears to act like fulvestrant in reducing ERα levels, we compared the effect of both drugs on WBP2-mediated breast cancer growth and proliferation. First, we exposed WBP2 phospho-mimic expressing MCF7 cells to serial concentrations of fulvestrant (0.1 nM, 1 nM, 10 nM, 100 nM and 1 µM) and probed for ERα expression to determine the effective working concentration. One hundred nM fulvestrant almost completely abolished ERα expression (data not shown). Next, we compared the growth and proliferation of WBP2 phospho-mimic mutant expressing MCF7 in the presence of 100 nM fulvestrant or 15 µM FH535. The results show that fulvestrant inhibited growth of MCF7 cells expressing vector and Y192-231E mutant by about 50% and 40%, respectively at day 4 (FIG. 6H). In contrast, FH535 reduced proliferation of MCF7 cells expressing vector and Y192-231E mutant by about 30% and 65%, respectively at day 4. Little synergy was observed between fulvestrant and FH535. Hence, inhibition by FH535 produced a more marked difference in the interference of cell proliferation between the vector control and WBP2 phospho-mimic mutant. A more pronounced inhibition by FH535 is not surprising since Wnt may not only regulate expression of ERα (FIG. 18G) but also possibly other oncogenes. The results suggest that while ERα expression is important, WBP2 phospho-mimic-driven MCF7 cells are more dependent on Wnt than the ERα pathway.

Discussions

Stimulation of ER-positive breast cancer cells with estrogen leads to tyrosine phosphorylation of WBP2 at Tyr192 and Tyr231 via EGFR crosstalk. WBP2 phosphorylation is regulated by c-Src (upstream/downstream of EGFR) and c-Yes (probably downstream of EGFR) tyrosine kinases. Tyrosine phosphorylation enhances WBP2's entry into nucleus where it potentially forms a transcriptional complex with ERα and leads to an overall increase in target gene transcription in an estrogen-dependent manner. Heightened WBP2 expression and phosphorylation not only potentiate ERα signaling pathway but also activate multiple oncogenes such as Wnt and promote their crosstalk with ERα leading to further enhancement of ERα signaling independent of estrogen—all of which contributing to the aggressive traits of breast cancer.

While the role of WBP2 in ERα and PR transactivation has been reported (11), our data further revealed that WBP2's coactivation function is regulated by tyrosine phosphorylation. Other steroid hormone receptor coactivators also exploit phosphorylation to regulate their function. For example, AIB1 was found to be tyrosine phosphorylated by c-Abl at Tyr1357 upon IGF1, EGF and estrogen treatment (4). Tyrosine phosphorylation of AIB1 altered its interaction with ERα, histone acetyltransferase (CBP/p300) and methyltransferase (CARM1) (4). On the other hand, serine phosphorylation of NRIF3 enhanced its nuclear localization, interaction with ERα and subsequently increased ERα transactivation (5). Tyr192 and Tyr231 are embedded within the polyproline-rich domain of WBP2 that consists of three highly conserved PY motifs. PY motif mediates protein-protein interaction and is present in many transcription factors and coactivators, including c-Jun (32), AP-2 (33), C/EBPα (34) and PEBPs (35). It is conceivable that phosphorylation of Tyr192 and Tyr231 regulates the transcriptional coactivator role of WBP2 by controlling the PY motif-mediated interactions with other partners in the transcriptional and/or epigenetics machinery. Protein interactions studies are underway to test this hypothesis. However, the coactivator activity of WBP2 was not absolutely regulated by the tyrosine phosphorylation at Tyr192 and 231, implying that other regions of WBP2 are also critical for its function. For example, the reported binding of Nedd4 E3 ligase to the proline-rich region of WBP2 suggests that regulation of protein stability (e.g. of transcriptional components) may be another mode through which WBP2 regulates transcription (36, 37).

Emerging evidences have demonstrated the importance of transcription coactivator in oncogenesis. Overexpression of TAZ in normal breast epithelial cells-MCF10A induced morphological changes characteristic of cell transformation and enhanced cell migration/invasion (3). Overexpression of NRIF3 and its S28E phosphorylation-mimic mutant in MCF7 increased cell proliferation and anchorageindependent growth (5). Similarly, overexpression of AIB1 and its Y1357E phosphorylation-mimic mutant in MEF induces focus formation (4). Phospho-Y1357 level of AIB1 was also found to be increased in mammary tumors developed in the MMTV-driven HER2/neu transgenic mouse model (4). Our findings that WBP2 overexpression and its tyrosine phosphorylation play critical roles in cell proliferation, anchorage-independent growth, migration and invasion, paved the way for future studies into cancer therapeutics exploiting WBP2 as a drug target for treatment of ERα/PR-positive breast cancer to complement hormonal therapy or even other subtypes such as the triple-negative breast cancer of which there is no standard treatment regime. Our preliminary screening showed that WBP2 expression was low or undetectable in normal breast epithelial cells but overexpressed in 12/16 human breast cancer cell lines of diverse molecular subtypes including the ER-negative breast cancer cells (unpublished data). Although WBP2 enhanced E2/ERα signaling, the overexpression of WBP2 in ER negative breast cancer cell lines suggests that the function of WBP2 is not strictly dependent on nor restricted to ERα. This is consistent with the observations that overexpression of WBP2 and its phospho-mimic form alone could drive many biochemical and cellular processes in the absence of E2/ERα signaling. It is conceivable that WBP2 could exert its transcriptional coactivator function on other transcription factors, e.g. AIB1 is a transcriptional coactivator for multiple other nuclear receptors beside ERα, including E2F-1 (38), NF-KB (6) and STAT6 (39).

WBP2 and its tyrosine phosphorylation contribute to the hallmarks of cancer via regulation of gene expression. A number of signaling perturbations associated with EMT (e.g. down-regulation of ECadherin and ZO-2 tight junction proteins) and resistance to apoptosis (e.g. up regulation of BCL2) have been detected in our study. Up-regulation of genes associated with ERα (YAP, ERα, Cyclin D1) and Wnt (Wnt3a, phospho-GSKβ, β-catenin, Cyclin D1, c-Myc) could have conferred growth independence phenotype (e.g. higher cell proliferative, transforming, migratory and invasive potential in the absence of estrogen) to breast cancer cells observed in this study. A more comprehensive gene expression profiling would be interesting to map the global classes of transcriptional targets of WBP2.

Cross-regulation of Wnt pathway components with nuclear receptor family members has become important in endocrine biology (29). β-catenin associates with ERα and their interaction is enhanced in the presence of estrogen (40), thereby promoting ERα transactivation. However, the regulation of ERα/β-catenin interaction in promoting estrogen signaling and tumorigenesis remains unclear. β-catenin has been demonstrated to recruit coactivators, such as p300/CBP complex (41) and components of SWI/SNF and RSC chromatin remodeling complexes (42), that might explain part of the regulatory mechanism. Contributing to this complicated process, we identified WBP2 as a novel mediator in the putative estrogen→EGFR→WBP2→Wnt→ER pathway (simplistically put). Our data showed that WBP2 up-regulated signaling components in estrogen and Wnt pathway but it is unclear how these were achieved. Did WBP2 work directly by cooperating with relevant transcription factors to drive gene expression or did it work indirectly through the transcription co-regulators (e.g. β-catenin) that it upregulated? Did WBP2 also engage chromatin remodeling complexes or facilitate the formation of higher order complexes such as long range chromatin interactions? These are questions that will be addressed.

Our data provide new insights into how Wnt signaling may modulate estrogen signaling. The increase in ERα expression in MCF7 expressing phospho-mimic WBP2 coupled to the observed down-regulation of ERα expression following Wnt inhibition suggest that ERα gene itself could be a target of LEF1/TCFinediated transcription. This is not without precedence—AR mRNA was highly up-regulated by the activation of Wnt-signaling in prostate cancer cells (43).

Although transforming activity in normal mammary epithelial cells has not yet been assessed, WBP2 behaves like an oncogene. Tyrosine phosphorylation of WBP2 serves as a molecular on/off switch that controls the crosstalk between Estrogen, EGF and Wnt/other oncogenic signaling pathways leading to amplification of ER receptor activity, dysregulation of multiple oncogenes and tumor suppressors. All these may act cooperatively to promote uncontrolled breast cancer growth. Our study has added WBP2 to the increasing list of nuclear receptor coactivators (AIB1, NRIF3, YAP, TAZ, etc) that are implicated in breast cancer.

Figure 10:
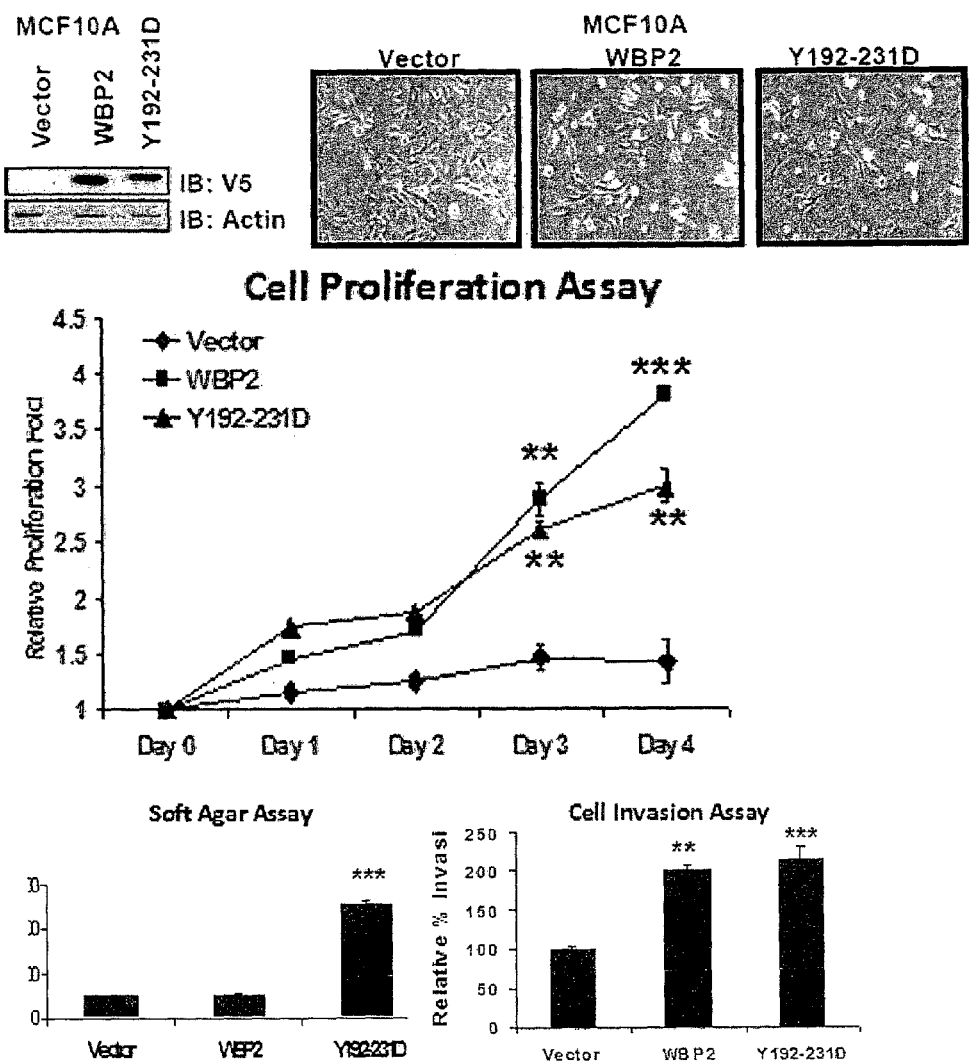

Overexpression of Wild Type and Phosphomimic Mutant-WBP2 in MCF7 Promotes Tumor Formation In Vivo To assess the in vivo significance of WBP2 and its phosphorylation in promoting in vitro cellular transformation, we have conducted xenografts studies with the MCF7 stable transfectants expressing vector, WBP2, phosphomimic and phosphodefective mutant. The result shows that vector control MCF7 cells were weakly tumorigenic while cells expressing WBP2 and Y192-231E phosphomimic mutant formed about 3-4 times bigger tumors than control cells. Cells expressing phosphodefective WBP2 mutant produced only marginally larger tumors than control cells, as shown in FIG. 10.

Figure 9:
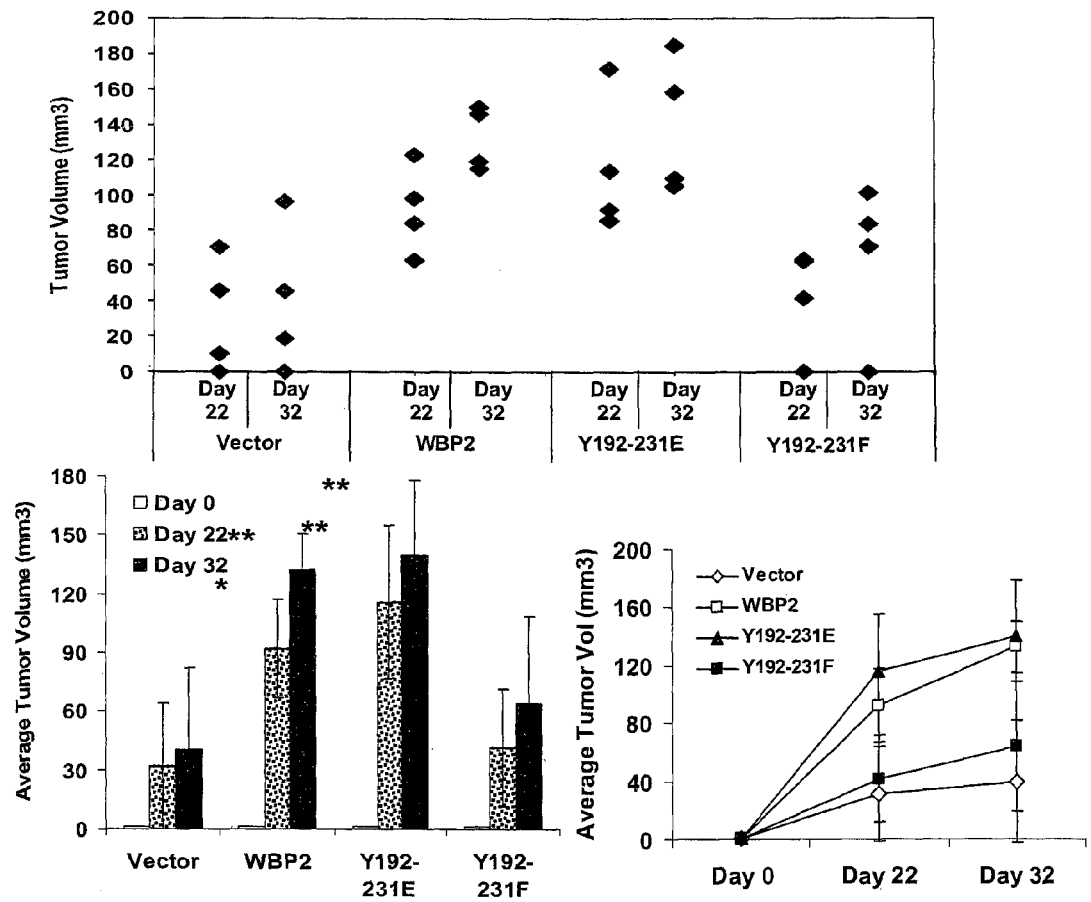

Overexpression of WBP2 and Y192-231D Phosphomimic Mutant in MCF10a Play a Role in Breast Tumorigenesis in MCF10A To study WBP2 as a potential oncogene in breast cancer, we generated a stable pool of vector, WBP2-WT and Y192-231D overexpression transfectants in the normal breast epithelial cell-MCF10A. Morphological examination in 2D culture revealed that there was a morphological change to a less compact, more fibroblastic phenotype upon WBP2 overexpression. This WBP2 stable transfectants were subject to various in vitro cell growth assays, including cell proliferation, soft agar colony formation and cell invasion assays, as shown in FIG. 9. Overexpression of both WBP2-WT and its phosphomimic mutant promoted cell proliferation and invasive potential. However, WBP2-WT did not confer anchorage-independent growth to normal mammary epithelial cells. In contrast, WBP2 phosphomimic mutant expressing MCF10A cells grew 5 fold better in soft agar.

Figure 11:
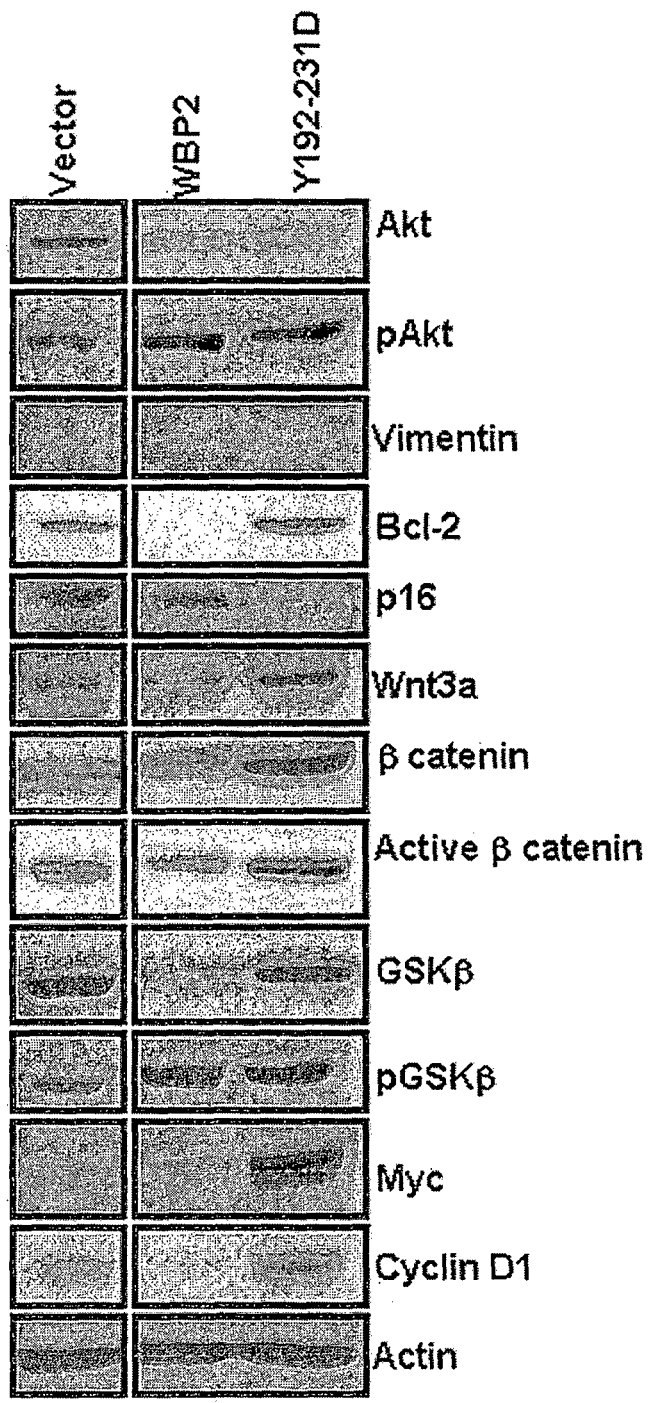

More Protein Expression/Activity Changes Associated with WT- and Y192-231E-WBP2 Overexpression Changes in protein expression and/or activity were detected to be associated with WT- and Y192-231D-WBP2 overexpression in MCF10A, as shown in FIG. 11. Increased Wnt pathway activation (Wnt3a, β-catenin, GSK, Myc, cyclin D1) was observed. Other changes include increased Akt activity, upregulated expression of vimentin (EMT marker) and anti-apoptotic protein Bcl-2 as well as down-regulation of cell cycle inhibitor p16.

WBP2 Expression Correlates with Differentiation Status

Figure 12:
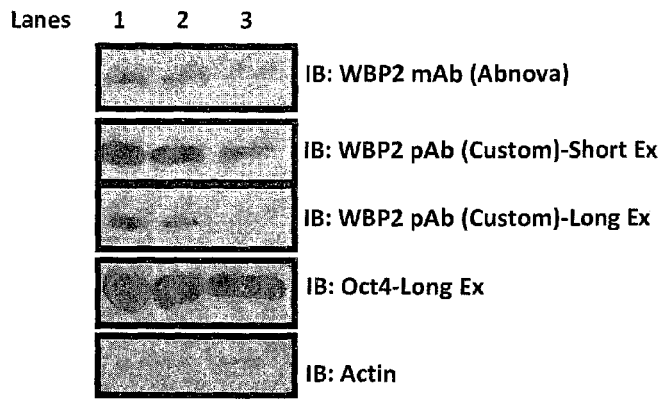

A correlation study was carried out to see if WBP2 plays a role in stem cell signaling. Expression of WBP2 was examined in HM-1 cells, which are deficient in hypoxanthine phosphoribosyl transferase (HPRT), were derived from HPRT-deficient strain 129 mice and characterized as highly pluripotent. Interestingly, WBP2 expression was downregulated upon induction of differentiation of HM-1 cells (FIG. 12).

Tyrosine Phosphorylation of WBP2 Regulates its Interaction with TAZ

Figure 13:
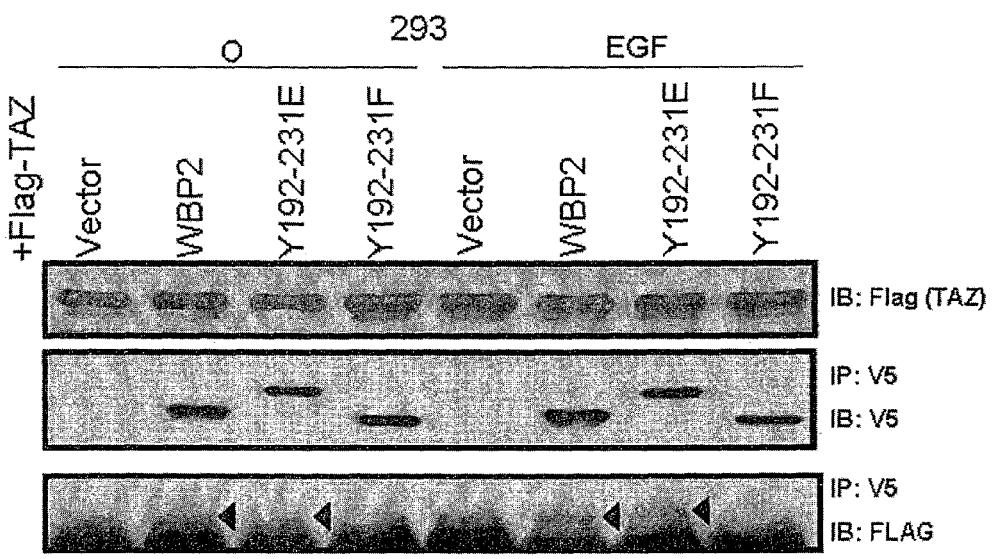
Figure 14:
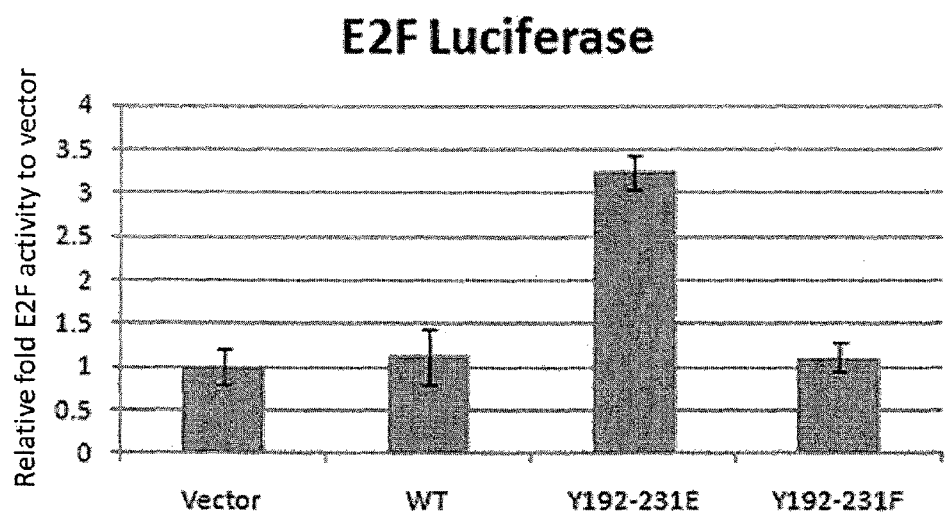
Figure 15:
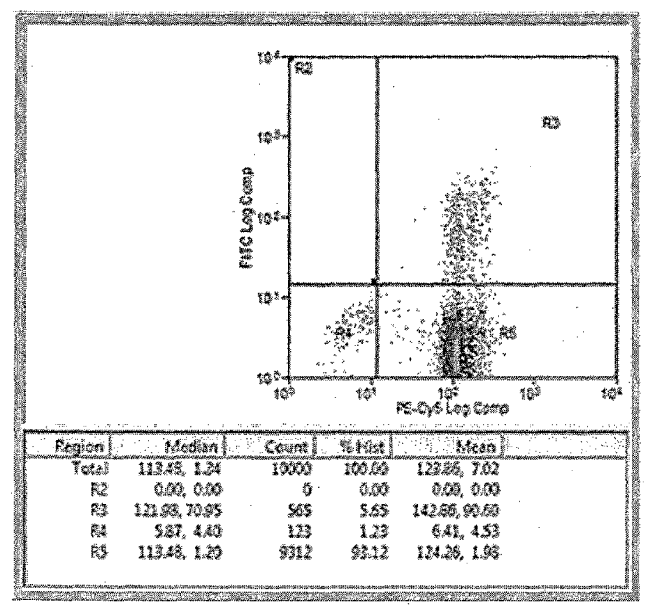
Figure 15:
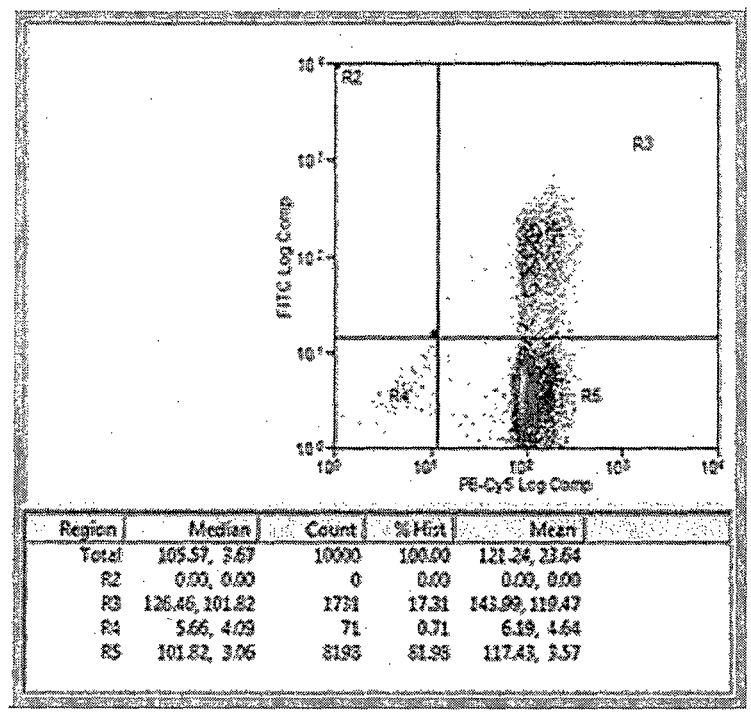
Figure 15:
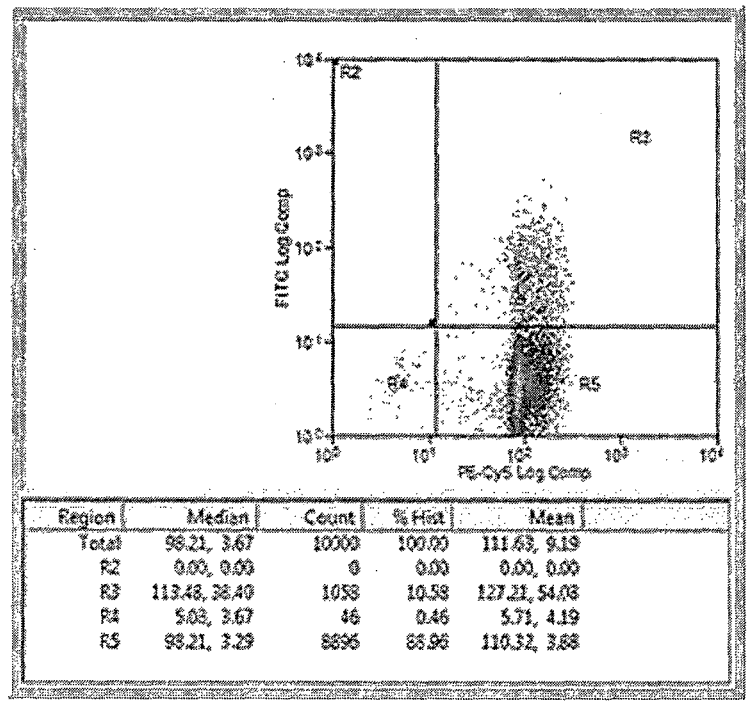
Figure 15:
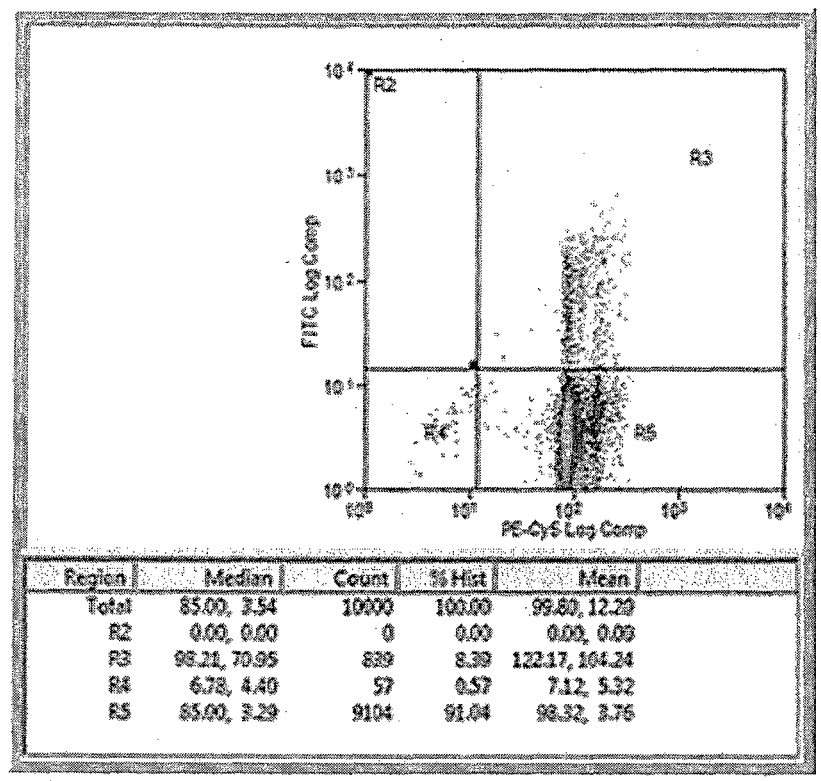
Figure 15:
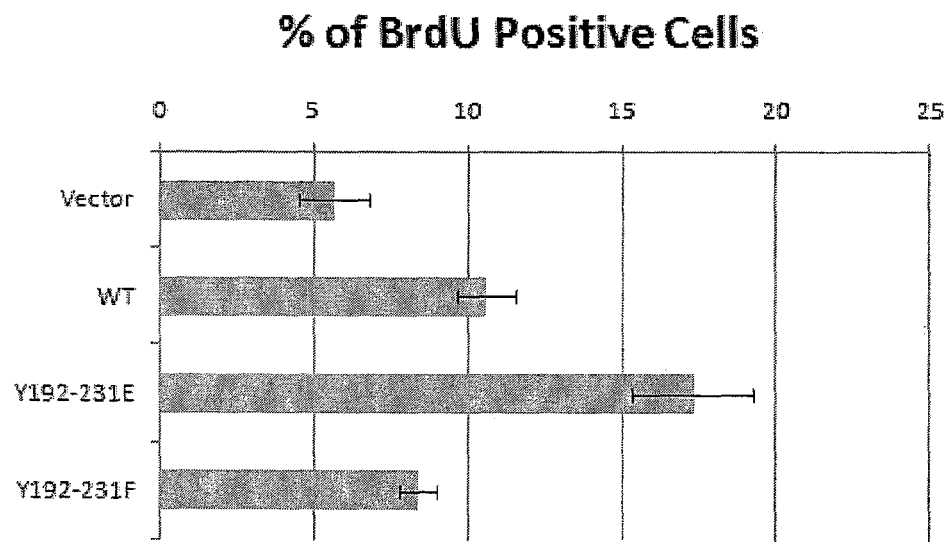
Figure 17:
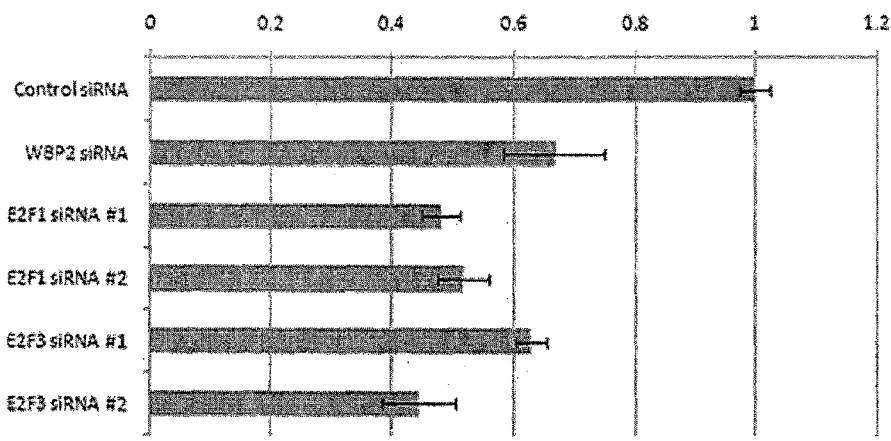
Figure 17:
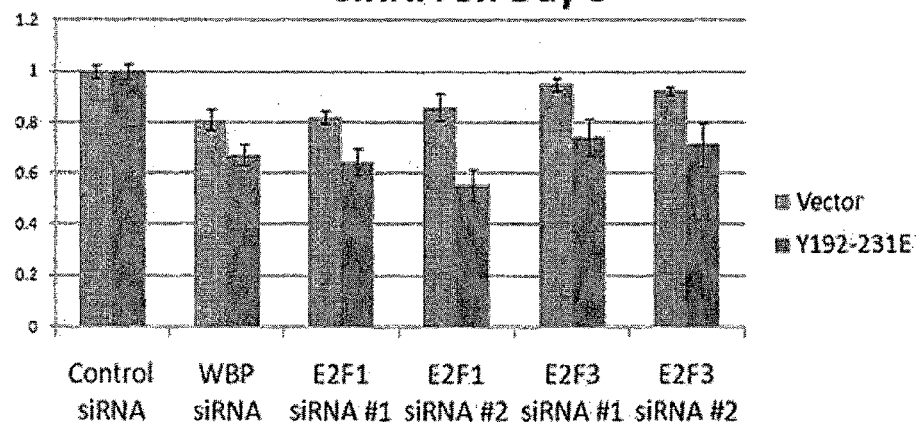

It was recently shown that WBP2 is required for TAZ-mediated oncogenic transformation via WBP2-TAZ interaction. We therefore examine if tyrosine phosphorylation of WBP2 regulates its interaction with TAZ. As shown in FIG. 13, tyrosine phosphorylation of WBP2 upon EGF stimulation potentiated the WBP2-TAZ interaction, which was disrupted when the tyrosine phosphorylation was abolished.

E2F Reporter Activity was Enhanced in MCF Cells Overexpressing WBP2-Y192-231E

WBP2 has been previously identified to be a transcriptional co-activator. It is likely that WBP2 exerts its effects by impacting multiple signaling pathways. To identify potential pathways that could account for WBP2 effects, we screened a number of pathway reporters. We found that E2F reporter activity is increased in cells overexpressing WBP2-Y192-

231E. This may indicate that phosphorylation of WBP2 activates the E2F pathway. This is the 3$^{rd}$ oncogenic pathway that we have identified to be activated by WBP2—the other being Wnt and ER pathways.

Increased Cell Cycle Progression was Observed in MCF7 Cells Overexpressing WBP2-Y192-231E Increased E2F activity is most commonly associated with cell cycle progression. The BrdU incorporation assay allows detection of cells that have progressed through the S-phase. The results below indicate that MCF7 cells expressing WBP2-Y192-231E progressed faster through the cell cycle.

E2F Protein Levels were Increased in Cells Overexpressing WBP2-Y192-231E

The E2F pathway comprise of several transcription factors categorized as activators or repressors. Increase in E2F activity may be attributed to increased levels of E2F transcription activators. Therefore we probed for expression of E2F1, E2F2 and E2F3. Detectable increases in protein levels were seen in cells expressing WBP2-Y192-231E.

Knockdown of E2F1 and E2F3 Reduced E2F Activity, Cell Cycle Progression and Cell Proliferation in MCF7 Cells Expressing WBP2-Y192-231E E2F1 and E2F3 have both been linked to cell proliferation and cell cycle progression. To investigate whether increases in the levels of E2F1 and E2F3 could account for the observed phenotypes, the MCF7 cells overexpressing WBP2-Y192-231E were transfected with siRNA targeting E2F1 and E2F3. siRNAs against E2F1 and E2F3 both result in reduced luciferase activity, reduced cell cycle progression and reduced cell proliferation. The E2F pathway may be important for mediating the effect of phospho-mimic WBP2.

Stimulation of ER☐-positive breast cancer cells with estrogen led to tyrosine phosphorylation of WBP2 at Tyr192 and Tyr231 via EGFR crosstalk. WBP2 phosphorylation was regulated by c-Src (upstream/downstream of EGFR) and c-Yes (probably downstream of EGFR) tyrosine kinases. Tyrosine phosphorylation enhanced WBP2's entry into nucleus where it potentially forms a transcriptional complex with ERα and led to an overall increase in target gene transcription in an estrogen-dependent manner. Heightened WBP2 expression and phosphorylation not only potentiated ERα signaling pathway but also activated multiple oncogenes such as Wnt and promoted crosstalk with ERα leading to further enhancement of ERα signaling independent of estrogen—all of which contributing to the aggressive traits of breast cancer. While the role of WBP2 in ERα and PR transactivation has been reported (11), our data further revealed that WBP2's coactivation function is regulated by tyrosine phosphorylation. Other steroid hormone receptor coactivators also exploit phosphorylation to regulate their function. For example, AIB1 was found to be tyrosine phosphorylated by c-Abl at Tyr1357 upon IGF1, EGF and estrogen treatment (4). Tyrosine phosphorylation of AIB1 altered its interaction with ERα, histone acetyltransferase (CBP/p300) and methyltransferase (CARM1) (4). On the other hand, serine phosphorylation of NRIF3 enhanced its nuclear localization, interaction with ERα and subsequently increased ERα transactivation (5). Tyr192 and Tyr231 are embedded within the polyproline-rich domain of WBP2 that consists of three highly conserved PY motifs. PY motif mediates protein-protein interaction and is present in many transcription factors and coactivators, including c-Jun (38), AP-2 (39), C/EBPα (40) and PEBPs (41). It is conceivable that phosphorylation of Tyr192 and Tyr231 regulates the transcriptional coactivator role of WBP2 by controlling the PY motif-mediated interactions with other partners in the transcriptional and/or epigenetics machinery. Very recently, the interaction of TAZ via its ww domain with the PY motif of WBP2 has been reported to be required for the oncogenic property of TAZ (32). It is conceivable that tyrosine phosphorylation of WBP2 regulates its interaction of TAZ and thereby promoting their transcriptional coactivator activity thereby driving oncogenesis. Studies are underway to test this hypothesis. However, the coactivator activity of WBP2 was not absolutely regulated by the tyrosine phosphorylation at Tyr192 and 231, implying that other regions of WBP2 are also critical for its function. For example, the reported binding of Nedd4 E3 ligase to the proline-rich region of WBP2 suggests that regulation of protein stability (e.g. of transcriptional components) may be another mode through which WBP2 regulates transcription (42, 43).

Emerging evidences have demonstrated the importance of transcriptional coactivator in oncogenesis. Overexpression of TAZ in normal breast epithelial cells-MCF10A induced morphological changes characteristic of cell transformation and enhanced cell migration/invasion (3). Overexpression of NRIF3 and its S28E phosphorylation-mimic mutant in MCF7 increased cell proliferation and anchorage-independent growth (5). Similarly, overexpression of AIB1 and its Y1357E phosphorylationmimic mutant in MEF induces focus formation (4). Phospho-Y1357 level of AIB1 was also found to be increased in mammary tumors developed in the MMTV-driven HER2/neu transgenic mouse model (4). Our findings that WBP2 overexpression and its tyrosine phosphorylation play critical roles in cell proliferation, anchorage-independent growth, migration and invasion, paved the way for future studies into cancer therapeutics exploiting WBP2 as a drug target for treatment of ERα/PR-positive breast cancer to complement hormonal therapy or even other subtypes such as the triple-negative breast cancer of which there is no standard treatment regime. Our preliminary screening showed that WBP2 expression was also overexpressed in ER-negative breast cancer cells (unpublished data). Although WBP2 enhanced E2/ERα, signaling, the overexpression of WBP2 in ER-negative breast cancer cell lines suggests that the function of WBP2 is not strictly dependent on nor restricted to ERα. This is consistent with the observations that overexpression of WBP2 and its phospho-mimic form alone could drive many biochemical and cellular processes in the absence of E2/ERα signaling. It is conceivable that WBP2 could exert its transcriptional coactivator function on other transcription factors, e.g. AIB 1 is a transcription coactivator for multiple other nuclear receptors besides ERα, including E2F-1 (44), NF-KB (6) and STAT6 (45).

WBP2 and its tyrosine phosphorylation contribute to the hallmarks of cancer via regulation of gene expression. A number of signaling perturbations associated with EMT (e.g. down-regulation of E Cadherin and ZO-2 tight junction proteins as well as upregulation of vimentin) and resistance to apoptosis (e.g. up regulation of BCL2) have been detected in our study. Up-regulation of genes associated with ERα (YAP, ERα, Cyclin D1) and Wnt (Wnt3a, phospho-GSKβ, β-catenin, Cyclin D1, c-Myc) could have conferred hormone independence phenotype (e.g. higher cell proliferative, transforming, migratory and invasive potential in the absence of estrogen) to breast cancer cells observed in this study. Of particular interest is the upregulation of ER and Wnt pathway by WBP2. Cross-regulation of Wnt pathway components with nuclear receptor family members has become increasingly important in endocrine biology (35). β-catenin associates with ERα. and their interactions are enhanced in the presence of estrogen (46), thereby promoting ERα transactivation. However, the regulation of ERα/

β-catenin interaction in promoting estrogen signaling and tumorigenesis remains unclear. β-catenin has been demonstrated to recruit coactivators, such as p300/CBP complex (47) and components of SWI/SNF and RSC chromatin remodeling complexes (48), that might explain part of the regulatory mechanism. Using pharmacological inhibitors, we showed that interference of WBP2-induced Wnt pathway reduced ERα expression and that WBP2-mediated breast cancer is more dependent on Wnt than on ERα pathway. All the data put together, we have identified WBP2 as a novel mediator in the putative estrogen→EGFR→WBP2→Wnt→ERα pathway (simplistically put). Our data showed that WBP2 upregulated signaling components in estrogen and Wnt pathway. However, it remains to be investigated how these were achieved. Did WBP2 work directly by cooperating with relevant transcription factors to drive gene expression or did it work indirectly through the transcriptional co-regulators (e.g. β-catenin, YAP) that it up-regulated? Did WBP2 also engage chromatin remodeling complexes or facilitate the formation of higher order complexes such as long range chromatin interactions? These questions are currently being addressed in our laboratory. Our data provide new insights into how Wnt signaling may modulate estrogen signaling. The increase in ERα expression in MCF7 expressing phospho-mimic WBP2 coupled to the observed down-regulation of ERα, expression following Wnt inhibition suggest that ERα gene itself could be a target of LEF1/TCF-mediated transcription. This is not without precedence -AR mRNA was highly up-regulated by the activation of Wnt-signaling in prostate cancer cells (49).

Consistent with a recent report (32), we showed that WBP2 expression alone was not sufficient to drive cellular transformation in normal mammary epithelial cells. Instead, the phospho-mimic mutant of WBP2 behaves like an oncogene that conferred anchorage independent growth of MCF10A normal mammary epithelial cells in soft agar and endowed aggressive traits to breast cancer cells. It is conceivable that phosphorylation primes WBP2 that would otherwise require factors (interactions with protein partners, other modifications) for cooperative function. Tyrosine phosphorylation of WBP2 may serve as a molecular on/off switch that controls the crosstalk between estrogen, EGF and Wnt/other oncogenic signaling pathways leading to amplification of ER ☐ receptor activity, dysregulation of multiple oncogenes and tumor suppressors. Our study adds WBP2 to the list of nuclear receptor coactivators (AIB1, NRIF3, YAP, TAZ, etc) that are increasingly implicated in breast cancer.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of and "consists essentially of have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

REFERENCES

1. Lee, J. W., Lee, Y. C., Na, S. Y., Jung, D. J., and Lee, S. K. (2001) Transcriptional coregulators of the nuclear receptor superfamily: coactivators and corepressors. Cell Mol Life Sci 58, 289-297
2. McKenna, N. J., and O'Malley, B. W. (2002) Combinatorial control of gene expression by nuclear receptors and coregulators. Cell 108, 465-474
3. Chan, S. W., Lim, C. J., Guo, K., Ng, C. P., Lee, I., Hunziker, W., Zeng, Q., and Hong, W. (2008) A role for TAZ in migration, invasion, and tumorigenesis of breast cancer cells. Cancer Res 68, 2592-2598
4. Oh, A. S., Lahusen, J. T., Chien, C. D., Fereshteh, M. P., Zhang, X., Dakshanamurthy, S., Xu, J., Kagan, B. L., Wellstein, A., and Riegel, A. T. (2008) Tyrosine phosphorylation of the nuclear receptor coactivator AIB1/SRC-3 is enhanced by Abl kinase and is required for its activity in cancer cells. Mol Cell Biol 28, 6580-6593
5. Talukder, A. H., Li, D. Q., Manavathi, B., and Kumar, R. (2008) Serine 28 phosphorylation of NRIF3 confers its co-activator function for estrogen receptor-alpha transactivation. Oncogene 27, 5233-5242
6. Wu, R. C., Qin, J., Hashimoto, Y., Wong, J., Xu, J., Tsai, S. Y., Tsai, M. J., and O'Malley, B. W. (2002) Regulation of SRC-3 (pCIP/ACTR/AIB-1/RAC-3/TRAM-1) Coactivator activity by I kappa B kinase. Mol Cell Biol 22, 3549-3561
7. Lazaro, J. B., Bailey, P. J., and Lassar, A. B. (2002) Cyclin D-cdk4 activity modulates the subnuclear localization and interaction of MEF2 with SRC-family coactivators during skeletal muscle differentiation. Genes Dev 16, 1792-1805
8. Rowan, B. G., Garrison, N., Weigel, N. L., and O'Malley, B. W. (2000) 8-Bromo-cyclic AMP induces phosphorylation of two sites in SRC-1 that facilitate ligand-independent activation of the chicken progesterone receptor and are critical for functional cooperation between SRC-1 and CREB binding protein. Mol Cell Biol 20, 8720-8730
9. Pierce, K. L., Luttrell, L. M., and Lefkowitz, R. J. (2001) New mechanisms in heptahelical receptor signaling to mitogen activated protein kinase cascades. Oncogene 20, 1532-1539
10. Lahusen, T., Henke, R. T., Kagan, B. L., Wellstein, A., and Riegel, A. T. (2009) The role and regulation of the nuclear receptor co-activator AIB1 in breast cancer. Breast Cancer Res Treat 116, 225-237
11. Dhananjayan, S. C., Ramamoorthy, S., Khan, O. Y., Ismail, A., Sun, J., Slingerland, J., O'Malley, B. W., and Nawaz, Z. (2006) WW domain binding protein-2, an E6-associated protein interacting protein, acts as a coactivator of estrogen and progesterone receptors. Mol Endocrinol 20, 2343-2354
12. Overholtzer, M., Zhang, J., Smolen, G. A., Muir, B., Li, W., Sgroi, D. C., Deng, C. X., Brugge, J. S., and Haber, D. A. (2006) Transforming properties of YAP, a candidate oncogene on the chromosome 11q22 amplicon. Proc Natl Acad Sci USA 103, 12405-12410
13. Strano, S., Munarriz, E., Rossi, M., Castagnoli, L., Shaul, Y., Sacchi, A., Oren, M., Sudol, M., Cesareni, G., and Blandino, G. (2001) Physical interaction with Yes-associated protein enhances p73 transcriptional activity. J Biol Chem 276, 15164-15173
14. Zaidi, S. K., Sullivan, A. J., Medina, R., Ito, Y., van Wijnen, A. J., Stein, J. L., Lian, J. B., and Stein, G. S. (2004) Tyrosine phosphorylation controls Runx2-mediated subnuclear targeting of YAP to repress transcription. EMBO J 23, 790-799
15. Vassilev, A., Kaneko, K. J., Shu, H., Zhao, Y., and DePamphilis, M. L. (2001) TEAD/TEF transcription factors utilize the activation domain of YAP65, a Src/Yes-associated protein localized in the cytoplasm. Genes Dev 15, 1229-1241
16. Komuro, A., Nagai, M., Navin, N. E., and Sudol, M. (2003) WW domain-containing protein YAP associates with ErbB-4 and acts as a co-transcriptional activator for the carboxyl-terminal fragment of ErbB-4 that translocates to the nucleus. J Biol Chem 278, 33334-33341
17. Chen, Y., Choong, L. Y., Lin, Q., Philp, R., Wong, C. H., Ang, B. K., Tan, Y. L., Loh, M. C., Hew, C. L., Shah, N., Druker, B. J., Chong, P. K., and Lim, Y. P. (2007) Differential Expression of Novel Tyrosine Kinase Substrates during Breast Cancer Development. Mol Cell Proteomics 6, 2072-2087
18. Lim, Y. P., Diong, L. S., Qi, R., Druker, B. J., and Epstein, R. J. (2003) Phosphoproteomic fingerprinting of epidermal growth factor signaling and anticancer drug action in human tumor cells. Mol Cancer Ther 2, 1369-1377
19. Toy, W., Lim, S. K., Loh, M. C., and Lim, Y. P. (2010) EGF-induced tyrosine phosphorylation of Endofin is dependent on PI3K activity and proper localization to endosomes. Cell Signal 22, 437-446
20. Fox, E. M., Andrade, J., and Shupnik, M. A. (2009) Novel actions of estrogen to promote proliferation: integration of cytoplasmic and nuclear pathways. Steroids 74, 622-627
21. Migliaccio, A., Castoria, G., Di Domenico, M., Ciociola, A., Lombardi, M., De Falco, A., Nanayakkara, M., Bottero, D., De Stasio, R., Varricchio, L., and Auricchio, F. (2006) Crosstalk between EGFR and extranuclear steroid receptors. Ann N Y Acad Sci 1089, 194-200
22. Lange, C. A. (2004) Making sense of cross-talk between steroid hormone receptors and intracellular signaling pathways: who will have the last word? Mol Endocrinol 18, 269-278
23. Kariagina, A., Xie, J., Leipprandt, J. R., and Haslam, S. Z. Amphiregulin Mediates Estrogen, Progesterone, and EGFR Signaling in the Normal Rat Mammary Gland and in Hormone-Dependent Rat Mammary Cancers. Horm Cancer 1, 229-244
24. Biscardi, J. S., Ishizawar, R. C., Silva, C. M., and Parsons, S. J. (2000) Tyrosine kinase signalling in breast cancer: epidermal growth factor receptor and c-Src interactions in breast cancer. Breast Cancer Res 2, 203-210
25. Brown, M. T., and Cooper, J. A. (1996) Regulation, substrates and functions of src. Biochim Biophys Acta 1287, 121-149
26. Sudol, M. (1994) Yes-associated protein (YAP65) is a proline-rich phosphoprotein that binds to the SH3 domain of the Yes proto-oncogene product. Oncogene 9, 2145-2152
27. Chen, H. I., Einbond, A., Kwak, S. J., Linn, H., Koepf, E., Peterson, S., Kelly, J. W., and Sudol, M. (1997) Characterization of the WW domain of human yes-associated protein and its polyprolinecontaining ligands. J Biol Chem 272, 17070-17077
28. Chen, H. I., and Sudol, M. (1995) The WW domain of Yes-associated protein binds a proline-rich ligand that differs from the consensus established for Src homology 3-binding modules. Proc Natl Acad Sci USA 92, 7819-7823
29. Biscardi, J. S., Maa, M. C., Tice, D. A., Cox, M. E., Leu, T. H., and Parsons, S. J. (1999) c-Src mediated phosphorylation of the epidermal growth factor receptor on Tyr845 and Tyr1101 is associated with modulation of receptor function. J Biol Chem 274, 8335-8343
30. Callige, M., and Richard-Foy, H. (2006) Ligand-induced estrogen receptor alpha degradation by the proteasome: new actors? Nucl Recept Signal 4, e004
31. Toy, W., Lim, S. K., Loh, M. C., and Lim, Y. P. EGF-induced tyrosine phosphorylation of Endofin is dependent on PI3K activity and proper localization to endosomes. Cell Signal 22, 437-446
32. Chan, S. W., Lim, C. J., Huang, C., Chong, Y. F., Gunaratne, H. J., Hogue, K. A., Blackstock, W. P., Harvey, K. F., and Hong, W. (2011) WW domain-mediated interaction with Wbp2 is important for the oncogenic property of TAZ. Oncogene 30, 600-610
33. Clevers, H. (2006) Wnt/beta-catenin signaling in development and disease. Cell 127, 469-480
34. Mohinta, S., Wu, H., Chaurasia, P., and Watabe, K. (2007) Wnt pathway and breast cancer. Front Biosci 12, 4020-4033
35. Mulholland, D. J., Dedhar, S., Coetzee, G. A., and Nelson, C. C. (2005) Interaction of nuclear receptors with the Wnt/beta-catenin/Tcf signaling axis: Wnt you like to know? Endocr Rev 26, 898-915
36. El-Tanani, M., Fernig, D. G., Barraclough, R., Green, C., and Rudland, P. (2001) Differential modulation of transcriptional activity of estrogen receptors by direct protein-protein interactions with the T cell factor family of transcription factors. J Biol Chem 276, 41675-41682

37. Handeli, S., and Simon, J. A. (2008) A small-molecule inhibitor of Tcf/beta-catenin signaling down-regulates PPARgamma and PPARdelta activities. Mol Cancer Ther 7, 521-529
38. Baichwal, V. R., and Tjian, R. (1990) Control of c-Jun activity by interaction of a cell-specific inhibitor with regulatory domain delta: differences between v- and c-Jun. Cell 63, 815-825
39. Williams, T., and Tjian, R. (1991) Analysis of the DNA-binding and activation properties of the human transcription factor AP-2. Genes Dev 5, 670-682
40. Nerlov, C., and Ziff, E. B. (1994) Three levels of functional interaction determine the activity of CCAAT/enhancer binding protein-alpha on the serum albumin promoter. Genes Dev 8, 350-362
41. Yagi, R., Chen, L. F., Shigesada, K., Murakami, Y., and Ito, Y. (1999) A WW domain-containing yesassociated protein (YAP) is a novel transcriptional co-activator. EMBO J 18, 2551-2562
42. Jolliffe, C. N., Harvey, K. F., Haines, B. P., Parasivam, G., and Kumar, S. (2000) Identification of multiple proteins expressed in murine embryos as binding partners for the WW domains of the ubiquitin-protein ligase Nedd4. Biochem J 351 Pt 3, 557-565
43. Pirozzi, G., McConnell, S. J., Uveges, A. J., Carter, J. M., Sparks, A. B., Kay, B. K., and Fowlkes, D. M. (1997) Identification of novel human WW domain-containing proteins by cloning of ligand targets. J Biol Chem 272, 14611-14616
44. Louie, M. C., Zou, J. X., Rabinovich, A., and Chen, H. W. (2004) ACTR/AIB 1 functions as an E2F1 coactivator to promote breast cancer cell proliferation and antiestrogen resistance. Mol Cell Biol 24, 5157-5171
45. Arimura, A., vn Peer, M., Schroder, A. J., and Rothman, P. B. (2004) The transcriptional coactivator p/CIP (NCoA-3) is up-regulated by STAT6 and serves as a positive regulator of transcriptional activation by STAT6. J Biol Chem 279, 31105-31112
46. Kouzmenko, A. P., Takeyama, K., Ito, S., Furutani, T., Sawatsubashi, S., Maki, A., Suzuki, E., Kawasaki, Y., Akiyama, T., Tabata, T., and Kato, S. (2004) Wnt/beta-catenin and estrogen signaling converge in vivo. J Biol Chem 279, 40255-40258
47. Hecht, A., Vleminckx, K., Stemmler, M. P., van Roy, F., and Kemler, R. (2000) The p300/CBP acetyltransferases function as transcriptional coactivators of beta-catenin in vertebrates. EMBO J 19, 1839-1850
48. Barker, N., Hurlstone, A., Musisi, H., Miles, A., Bienz, M., and Clevers, H. (2001) The chromatin remodelling factor Brg-1 interacts with beta-catenin to promote target gene activation. EMBO J 20, 4935-4943
49. Yang, X., Chen, M. W., Terry, S., Vacherot, F., Bemis, D. L., Capodice, J., Kitajewski, J., de la Taille, A., Benson, M. C., Guo, Y., and Buttyan, R. (2006) Complex regulation of human androgen receptor expression by Wnt signaling in prostate cancer cells. Oncogene 25, 3436-3444

The invention claimed is:

1. A method for detecting a phosphorylated WW-domain Binding Protein 2 comprising detecting an amount of a polypeptide of SEQ ID NO: 1 having a phosphorylated tyrosine at Y192 in a sample isolated from a human, wherein the polypeptide is detected using a phosphorylation site-specific antibody that specifically binds to the polypeptide when the polypeptide is phosphorylated at Y192.

2. The method of claim 1, further comprising detecting an amount of a polypeptide of SEQ ID NO: 1 having a phosphorylated tyrosine at Y231 in the sample, wherein the polypeptide is detected using a phosphorylation site-specific antibody that specifically binds to the polypeptide when the polypeptide is phosphorylated at Y231.

3. The method of claim 1, wherein the sample is tissue sample or cell sample.

4. The method of claim 3, wherein the sample is isolated from a nuclear fraction of a cell.

5. The method of claim 1, wherein the phosphorylation site-specific antibody binds to a peptide set forth in SEQ ID NO: 5 or SEQ ID NO: 6.

* * * * *

SEQUENCE LISTING

```
<160> NUMBER OF SEQ ID NOS: 11

<210> SEQ ID NO 1
<211> LENGTH: 261
<212> TYPE: PRT
<213> ORGANISM: Homo sapiens
<220> FEATURE:
<221> NAME/KEY: MISC_FEATURE
<222> LOCATION: (168)..(170)
<223> OTHER INFORMATION: polyproline-tyrosine motif
<220> FEATURE:
<221> NAME/KEY: MOD_RES
<222> LOCATION: (192)..(192)
<223> OTHER INFORMATION: PHOSPHORYLATION
<220> FEATURE:
<221> NAME/KEY: MISC_FEATURE
<222> LOCATION: (197)..(200)
<223> OTHER INFORMATION: polyproline-tyrosine motif
<220> FEATURE:
<221> NAME/KEY: MOD_RES
<222> LOCATION: (231)..(231)
<223> OTHER INFORMATION: PHOSPHORYLATION
<220> FEATURE:
<221> NAME/KEY: MISC_FEATURE
<222> LOCATION: (250)..(253)
<223> OTHER INFORMATION: polyproline-tyrosine motif

<400> SEQUENCE: 1

Met Ala Leu Asn Lys Asn His Ser Glu Gly Gly Val Ile Val Asn
1               5                   10                  15

Asn Thr Glu Ser Ile Leu Met Ser Tyr Asp His Val Glu Leu Thr Phe
                20                  25                  30

Asn Asp Met Lys Asn Val Pro Glu Ala Phe Lys Gly Thr Lys Lys Gly
            35                  40                  45

Thr Val Tyr Leu Thr Pro Tyr Arg Val Ile Phe Leu Ser Lys Gly Lys
        50                  55                  60
```

-continued

```
Asp Ala Met Gln Ser Phe Met Met Pro Phe Tyr Leu Met Lys Asp Cys
 65                  70                  75                  80

Glu Ile Lys Gln Pro Val Phe Gly Ala Asn Tyr Ile Lys Gly Thr Val
                 85                  90                  95

Lys Ala Glu Ala Gly Gly Gly Trp Glu Gly Ser Ala Ser Tyr Lys Leu
            100                 105                 110

Thr Phe Thr Ala Gly Gly Ala Ile Glu Phe Gly Gln Arg Met Leu Gln
        115                 120                 125

Val Ala Ser Gln Ala Ser Arg Gly Glu Val Pro Ser Gly Ala Tyr Gly
    130                 135                 140

Tyr Ser Tyr Met Pro Ser Gly Ala Tyr Val Tyr Pro Pro Pro Val Ala
145                 150                 155                 160

Asn Gly Met Tyr Pro Cys Pro Pro Gly Tyr Pro Tyr Pro Pro Pro Pro
                165                 170                 175

Pro Glu Phe Tyr Pro Gly Pro Pro Met Met Asp Gly Ala Met Gly Tyr
            180                 185                 190

Val Gln Pro Pro Pro Pro Tyr Pro Gly Pro Met Glu Pro Pro Pro Val
        195                 200                 205

Ser Gly Pro Asp Val Pro Ser Thr Pro Ala Ala Glu Ala Lys Ala Ala
    210                 215                 220

Glu Ala Ala Ala Ser Ala Tyr Tyr Asn Pro Gly Asn Pro His Asn Val
225                 230                 235                 240

Tyr Met Pro Thr Ser Gln Pro Pro Pro Pro Tyr Tyr Pro Pro Pro Glu
                245                 250                 255

Asp Lys Lys Thr Gln
            260

<210> SEQ ID NO 2
<211> LENGTH: 25
<212> TYPE: RNA
<213> ORGANISM: Artificial Sequence
<220> FEATURE:
<223> OTHER INFORMATION: siRNA

<400> SEQUENCE: 2
agcauccgcu guccgaacuc aaugg                                         25

<210> SEQ ID NO 3
<211> LENGTH: 12
<212> TYPE: PRT
<213> ORGANISM: Artificial Sequence
<220> FEATURE:
<223> OTHER INFORMATION: peptide derived from human WBP2 protein

<400> SEQUENCE: 3

Pro Pro Gly Tyr Pro Pro Pro Tyr Pro Pro Pro Tyr
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: peptide derived from human WBP2 protein

<400> SEQUENCE: 4

Pro Pro Gly Tyr Pro Pro Pro Tyr Pro Pro Pro Tyr
 1               5                  10

<210> SEQ ID NO 5
```

```
<211> LENGTH: 40
<212> TYPE: PRT
<213> ORGANISM: Artificial Sequence
<220> FEATURE:
<223> OTHER INFORMATION: peptide derived from human WBP2 protein

<400> SEQUENCE: 5

Tyr Val Gln Pro Pro Pro Pro Tyr Pro Gly Pro Met Glu Pro Pro
1               5                   10                  15

Val Ser Gly Pro Asp Val Pro Ser Thr Pro Ala Ala Glu Ala Lys Ala
            20                  25                  30

Ala Glu Ala Ala Ala Ser Ala Tyr
        35                  40

<210> SEQ ID NO 6
<211> LENGTH: 40
<212> TYPE: PRT
<213> ORGANISM: Artificial Sequence
<220> FEATURE:
<223> OTHER INFORMATION: peptide derived from human WBP2 protein

<400> SEQUENCE: 6

Tyr Val Gln Pro Pro Pro Pro Tyr Pro Gly Pro Met Glu Pro Pro
1               5                   10                  15

Val Ser Gly Pro Asp Val Pro Ser Thr Pro Ala Ala Glu Ala Lys Ala
            20                  25                  30

Ala Glu Ala Ala Ala Ser Ala Tyr
        35                  40

<210> SEQ ID NO 7
<211> LENGTH: 17
<212> TYPE: PRT
<213> ORGANISM: Artificial Sequence
<220> FEATURE:
<223> OTHER INFORMATION: antigen from a section of the human WBP2
      protein sequence No. 1 used for antibody production

<400> SEQUENCE: 7

Asn Asp Met Lys Asn Val Pro Glu Ala Phe Lys Gly Thr Lys Lys Gly
1               5                   10                  15

Thr

<210> SEQ ID NO 8
<211> LENGTH: 25
<212> TYPE: RNA
<213> ORGANISM: Artificial Sequence
<220> FEATURE:
<223> OTHER INFORMATION: siRNA sequence from Invitrogen

<400> SEQUENCE: 8
uucuccuaca agaauauuag cagcc                                              25

<210> SEQ ID NO 9
<211> LENGTH: 25
<212> TYPE: RNA
<213> ORGANISM: Artificial Sequence
<220> FEATURE:
<223> OTHER INFORMATION: siRNA sequence from Invitrogen

<400> SEQUENCE: 9
gccucucagu gucugacuuc gacaa                                              25

<210> SEQ ID NO 10
<211> LENGTH: 19
```

```
<212> TYPE: RNA
<213> ORGANISM: Artificial Sequence
<220> FEATURE:
<223> OTHER INFORMATION: siRNA sequence from Invitrogen

<400> SEQUENCE: 10
cguacgcgga auacuucga                                                  19

<210> SEQ ID NO 11
<211> LENGTH: 25
<212> TYPE: RNA
<213> ORGANISM: Artificial Sequence
<220> FEATURE:
<223> OTHER INFORMATION: siRNA sequence from Invitrogen

<400> SEQUENCE: 11
caggaacuag cauuguggga cauua                                           25
```